(12) United States Patent
O'Riordan et al.

(10) Patent No.: US 11,603,529 B2
(45) Date of Patent: Mar. 14, 2023

(54) VARIANT RNAI

(71) Applicant: Genzyme Corporation, Cambridge, MA (US)

(72) Inventors: Catherine R. O'Riordan, Bridgewater, NJ (US); Adam Palermo, Cambridge, MA (US); Brenda Richards, Bridgewater, NJ (US); Lisa M. Stanek, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 389 days.

(21) Appl. No.: 16/649,042

(22) PCT Filed: Sep. 21, 2018

(86) PCT No.: PCT/US2018/052221
§ 371 (c)(1),
(2) Date: Mar. 19, 2020

(87) PCT Pub. No.: WO2019/060726
PCT Pub. Date: Mar. 28, 2019

(65) Prior Publication Data
US 2020/0216848 A1  Jul. 9, 2020

Related U.S. Application Data

(60) Provisional application No. 62/561,843, filed on Sep. 22, 2017.

(51) Int. Cl.
| | | |
|---|---|---|
| *C12N 15/113* | (2010.01) | |
| *A61P 25/28* | (2006.01) | |
| *A61K 35/761* | (2015.01) | |
| *C12N 7/00* | (2006.01) | |
| *C12N 15/86* | (2006.01) | |
| *A61K 48/00* | (2006.01) | |

(52) U.S. Cl.
CPC .......... *C12N 15/113* (2013.01); *A61K 35/761* (2013.01); *A61P 25/28* (2018.01); *C12N 7/00* (2013.01); *C12N 15/86* (2013.01); *A61K 48/00* (2013.01); *C12N 2310/14* (2013.01); *C12N 2310/531* (2013.01); *C12N 2710/10023* (2013.01); *C12N 2710/10043* (2013.01)

(58) Field of Classification Search
CPC ....... A61K 48/00; A61P 25/28; C12N 15/113; C12N 15/907; C12N 2310/20; C12N 2750/14143
USPC ..................... 435/6.1, 91.1, 91.31, 455, 458; 514/44 A; 536/23.1, 24.5
See application file for complete search history.

(56) References Cited

U.S. PATENT DOCUMENTS

| | | |
|---|---|---|
| 6,566,118 B1 | 5/2003 | Atkinson |
| 6,596,535 B1 | 7/2003 | Carter |
| 6,723,551 B2 | 4/2004 | Kotin |
| 6,989,264 B2 | 1/2006 | Atkinson |
| 6,995,006 B2 | 2/2006 | Atkinson |
| 7,125,717 B2 | 10/2006 | Carter |
| 7,465,583 B2 | 12/2008 | Samulski |
| 7,785,888 B2 | 8/2010 | Carter |
| 7,790,154 B2 | 9/2010 | Samulski |
| 7,846,729 B2 | 12/2010 | Carter |
| 8,093,054 B2 | 1/2012 | Carter |
| 8,283,151 B2 | 10/2012 | Schmidt |
| 8,361,457 B2 | 1/2013 | Samulski |
| 8,481,701 B2 * | 7/2013 | Jarrige-Le Prado . C12Q 1/6883 536/23.1 |
| 10,265,377 B2 * | 4/2019 | Miller ..................... A61P 43/00 |
| 2009/0130751 A1 | 5/2009 | Davidson |
| 2012/0066783 A1 | 3/2012 | Kay |
| 2012/0164106 A1 | 6/2012 | Schaffer |
| 2013/0323226 A1 | 12/2013 | Wilson |
| 2014/0163214 A1 | 6/2014 | Davidson |
| 2014/0335054 A1 | 11/2014 | Gao |
| 2015/0099793 A1 | 4/2015 | Wang |
| 2018/0023082 A1 | 1/2018 | Stanek |
| 2022/0054657 A1 * | 2/2022 | O'Riordan ......... A61K 31/7105 |

FOREIGN PATENT DOCUMENTS

| | | |
|---|---|---|
| JP | 2004101787 A1 | 7/2006 |
| JP | 2010500025 A | 1/2010 |
| JP | 2011517339 A | 6/2011 |
| WO | 199810088 A1 | 3/1998 |
| WO | 2003042397 A2 | 5/2003 |
| WO | 2003042397 A3 | 2/2004 |
| WO | 2004029212 A2 | 4/2004 |
| WO | 2008021136 A2 | 2/2008 |

(Continued)

OTHER PUBLICATIONS

Ahi, Y. et al. (Aug. 2011). "Adenoviral Vector Immunity: Its Implications and Circumvention Strategies," Curr. Gene Ther. 11(4):307-320.

Alba, R. et al. (Oct. 2005) "Gutless Adenovirus: Last-Generation Adenovirus for Gene Therapy," Gene Ther. 12 (Suppl 1):S18-27.

Ambros, V. (Sep. 16, 2004). "The Functions of Animal MicroRNAs," Nature 431(7006):350-355.

Andersen, J.K. et al. (1993) "Herpesvirus-Mediated Gene Delivery into the Rat Brain: Specificity and Efficiency of the Neuron-Specific Enolase Promoter," Cell. Mol. Neurobiol. 13:503-515.

(Continued)

Primary Examiner — Jane J Zara
(74) Attorney, Agent, or Firm — Morrison & Foerster LLP

(57) ABSTRACT

Provided herein are RNAi molecules for treating Huntington's disease. Further provided herein are expression cassettes, vectors (e.g., rAAV, recombinant adenoviral, recombinant lentiviral, and recombinant HSV vectors), cells, viral particles, and pharmaceutical compositions containing the RNAi. Yet further provided herein are methods and kits related to the use of the RNAi, for example, to treat Huntington's disease.

43 Claims, 14 Drawing Sheets

Specification includes a Sequence Listing.

(56) References Cited

FOREIGN PATENT DOCUMENTS

| | | |
|---|---|---|
| WO | 2008021136 A3 | 7/2008 |
| WO | 2008150897 A2 | 12/2008 |
| WO | 2009098196 A2 | 8/2009 |
| WO | 2009100502 A1 | 8/2009 |
| WO | 2009098196 A3 | 11/2009 |
| WO | 2011034811 A1 | 3/2011 |
| WO | 2015168666 A2 | 11/2015 |
| WO | 2016102664 A1 | 6/2016 |
| WO | 2016130589 A2 | 8/2016 |
| WO | 2019060726 A1 | 3/2019 |

OTHER PUBLICATIONS

Arrasate, M. et al. (2004). "Inclusion Body Formation Reduces Levels of Mutant Huntingtin and the Risk of Neuronal Death," Nature 431(7010):805-810.

Augood, S.J. et al. (Aug. 1997). "Dopamine D1 and D2 Receptor Gene Expression in the Striatum in Huntington's Disease", Ann. Neural. 42(2):215-221.

Bates, G. (May 10, 2003). "Huntingtin Aggregation and Toxicity in Huntington's Disease", Lancet 361 (9369):1642-1644.

Benn, C.L. et al. (2008). "Huntingtin Modulates Transcription, Occupies Gene Promoters In Vivo, and Binds Directly to DNA in a Polyglutamine-Dependent Manner," J. Neurosci. 28(42):10720-10733.

Bhide, P.G. et al. (Sep. 1, 1996). "Expression of Normal and Mutant Huntingtin in the Developing Brain," J. Neurosci 16(17):5523-5535.

Boison, D. (Sep. 2010). "Inhibitory RNA in epilepsy: Research Tool and Therapeutic Perspectives," Epilepsia 51(9):1659-1668.

Boshart, M. et al. (Jun. 1985). "A Very Strong Enhancer is Located Upstream of an Immediate Early Gene of Human Cytomegalovirus," Cell 41(2):521-530.

Bossis, I. et al. (Jun. 2003). "Cloning of an Avian Adeno-Associated Virus (AAAV) and Generation of Recombinant AAAV Particles," J. Virol. 77(12):6799-6810.

Boudreau, R.L. et al. (Dec. 2011, e-pub. Sep. 27, 2021). "Rational Design of Therapeutic SiRNAs: Minimizing Off-targeting Potential to Improve the Safety of RNAi Therapy for Huntington's Disease," Molecular Therapy 19(12):2169-2177.

Boudreau, R.L. et al. (Jan. 2013, e-pub. Aug. 31, 2012). "siSPOTR: A Tool for Designing Highly Specific and Potent Simas for Human and Mouse," Nucleic Acids Res. 41(1):e9, 12 pages.

Boudreau, R.L. et al. (Jun. 2009, e-pub. Feb. 24, 2009). "Nonallele-Specific Silencing of Mutant and Wild-Type Huntingtin Demonstrates Therapeutic Efficacy in Huntington's Disease Mice", Mol. Ther. 17(6):1053-1063.

Castanotto, D. et al. (Jan. 22, 2009). "The Promises and Pitfalls of RNA-Interference-Based Therapeutics," Nature 457(7228):426-433.

Cattaneo, E. et al. (Dec. 2005). "Normal Huntingtin Function: An Alternative Approach to Huntington's Disease," Nat. Rev. Neurosci. 6(12):919-930.

Cha, J.H. (Sep. 2000). "Transcriptional Dysregulation in Huntington's Disease," Trends Neurosci. 23(9):387-392.

Chiu Y-L et al: "RNAi in Human Cells: Basic Structural and Functional Features of Small Interfering RNA", Molecular Cell, Cell Press, Cambridge, MA, US,vol. 10, Sep. 1, 2002 (Sep. 1, 2002), pp. 549-561.

Clark, K.R. et al. (Apr. 10, 1999). "Highly Purified Recombinant Adeno-Associated Virus Vectors are Biologically Active and Free of Detectable Helper and Wild-Type Viruses," Hum. Gene Ther. 10(6):1031-1039.

Clark, P. R. et al: "Knockdown of TNFR1 by,the sense strand of an ICAM-1 siRNA: dissection of an off-target effect", Nucleic Acids Research,vol. 36, No. 4, Jan. 1, 2007 (Jan. 1, 2007), pp. 1081-1097.

Conway, J.E. et al. (Nov. 1997). "Recombinant Adeno-Associated Virus Type 2 Replication and Packaging is Entirely Supported by a Herpes Simplex Virus Type 1 Amplicon Expressing Rep and Cap," J. Virology 71 (11):8780-8789.

Cronin, J. et al. (Aug. 2005). "Altering the Tropism of Lentiviral Vectors Through Pseudotyping," Curr. Gene Ther. 5(4):387-398.

Cryan, J.F. et al. (Feb. 2, 2002). "Noradrenergic Lesions Differentially Alter the Antidepressant-Like Effects of Reboxetine in a Modified Forced Swim Test," Eur. J. Pharmacol. 436(2002):197-205.

Dryan, J.F. et al. (May 2002) "Assessing Antidepressant Activity in Rodents: Recent Developments and Future Needs," Trends Pharmacol. Sci. 23(5):238-245.

Danthinne, X et al. (2000). "Production of First Generation Adenovirus Vectors: A Review," Viral Transfer Technology 7:1707-1714.

Davidson, B.L. et al. (Aug. 31, 2012). "Singles Engage the RNA Interference Pathway", Cell 150:873-875.

Davidson, B.L. et al. (Mar. 28, 2000). "Recombinant Adeno-Associated Virus Type 2,4, and 5 Vectors: Transduction of Variant Cell Types and Regions in the Mammalian Central Nervous System," PNAS 97(7):3428-3432.

Desplats, P.A. et al. (2006). "Selective deficits in the expression of striatal-enriched mRNAs in Huntington's disease", J. Neurochem 96:743-757.

Difiglia, M. et al. (Oct. 23, 2007). "Therapeutic Silencing of Mutant Huntingtin with siRNA Attenuates Striatal and Cortical Neuropathology and Behavioral Deficits," Proc. Natl. Acad. Sci. USA 104(43):17204-17209.

Difiglia, M. et al. (Sep. 26, 1997). "Aggregation of Huntingtin in Neuronal Intranuclear Inclusions and Dystrophic Neurites in Brain," Science 277(5334):1990-1993.

Drouet, V. et al. (Mar. 2009). "Sustained Effects of Nonallele-Specific Huntingtin Silencing", Ann. Neurol. 65(3):276-285.

Dull, T. et al. (Nov. 1998) "A Third-Generation Lentivirus Vector with a Conditional Packaging System," J. Viral. 72:8463-8471.

Durand, S. et al. (2011). "The Inside Out of Lentiviral Vectors," Viruses 3:132-59.

Fisher, K.J. et al. (Jan. 1996). "Transduction with Recombinant Adeno-Associated Virus for Gene Therapy Is Limited by Leading-Strand Synthesis" J. Virol. 70:520-532.

Fukuda, A.M. et al. (Sep. 5, 2013). "siRNA Treatment: "A Sword-in-the-Stone" for Acute Brain Injuries," Genes 4:435-456.

Gantier, M. et al. (Apr. 1, 2020). "Rational design of immunostimulatory siRNAs", Mol Ther. 18(4):785-795.

Gao, G. et al. (Jun. 2004). "Clades of Adeno-Associated Viruses are Widely Disseminated in Human Tissues," J. Virol. 78(12):6381-6388.

Gao, G. et al. (May 13, 2003). "Adeno-Associated Viruses Undergo Substantial Evolution in Primates During Natural Infections," PNAS 100(10):6081-6086.

Gao, G. et al. (Sep. 3, 2002). "Novel Adeno-Associated Viruses from Rhesus Monkeys as Vectors for Human Gene Therapy," PNAS 99(18):11854-11856.

GenBank Gene ID 396526.

Goins, W.F. et al. (2014). "Engineering HSV-1 Vectors for Gene Therapy," Chapter 5 in Herpes Simplex Virus Methods in Molecular Biology, Springer Science+Business Media, New York, 1144:63-79.

Gossen, M. et al. (Jun. 15, 1992). "Tight Control of Gene Expression in Mammalian Cells by Tetracycline-Responsive Promoters," Proc Natl Acad Sci USA. 89(12):5547-5551.

Gossen, M. et al. (Jun. 23, 1995). "Transcriptional Activation by Tetracyclines in Mammalian Cells," Science 268:1766-1769.

Grondin, R. et al. (Apr. 2012, e-pub. Jan. 16, 20012). "Six-Month Partial Suppression of Huntingtin is Well Tolerated in the Adult Rhesus Striatum," Brain 135(4):1197-1209.

Gu, S. et al. (Nov. 9, 2012). "The Loop Position of shRNAs and Pre-miRNAs Is Critical for the Accuracy of Dicer Processing In Vivo", Cell 151(4):900-911.

Guo, Z.S. et al. (Sep. 1996). "Evaluation of Promoter Strength for Hepatic Gene Expression in Vivo Following Adenovirus-Mediated Gene Transfer," Gene Ther. 3(9):802-810.

(56) References Cited

OTHER PUBLICATIONS

Gutekunst, C.A. et al. (Apr. 1, 1999). "Nuclear and Neuropil Aggregates in Huntington's Disease: Relationship to Neuropathology," J. Neurosci. 19(7):2522-2534.

Harper, S.Q. et al. (Apr. 19, 2005). "RNA Interference Improves Motor and Neuropathological Abnormalities in a Huntington's Disease Mouse Model," Proc. Natl. Acad. Sci. USA 102(16):5820-5825.

Harvey, D.M. et al. (1998). "Inducible Control of Gene Expression: Prospects for Gene Therapy," Curr. Opin. Chem. Biol. 2:512-518.

Huntington Study Group. (1996). "Unified Huntington's Disease Rating Scale: Reliability and Consistency," Movement Disorders 11:136-142.

International Preliminary Report on Patentability dated Mar. 24, 2020, for PCT Application No. PCT/US2018/052221, filed on Sep. 21, 2018, six pages.

International Preliminary Report on Patentability dated Aug. 15, 2017, for PCT Application No. PCT/US2016/017207, filed on Feb. 9, 2018, twelve pages.

International Search Report dated Aug. 8, 2016, for PCT Application No. PCT/US2016/017207, filed on Feb. 9, 2016, 8 pages.

International Search Report dated Jan. 7, 2019, for PCT Application No. PCT/US2018/052221, filed on Sep. 21, 2018, seven pages.

Jackson, A.L. et al. (Jan. 2010). "Recognizing and Avoiding siRNA Off-Target Effects for Target Identification and Therapeutic Application," Nature Rev. Drug Disc. 9(1):57-67.

Kay, M. et al. (Jan. 2001). "Viral Vectors for Gene Therapy: The Art of Turning Infectious Agents into Vehicles of Therapeutics," Nat. Med. 7(1):33-40.

Kim, D.W. et al. (1990). "Use of the Human Elongation Factor 1α Promoter as a Versatile and Efficient Expression System," Gene 91(2):217-223.

Kordasiewicz, H.B. et al. (Jun. 21, 2012). "Sustained Therapeutic Reversal of Huntington's Disease by Transient Repression of Huntingtin Synthesis," Neuron 74(6):1031-1044.

Kotin, R. (Jul. 1994). "Prospects for the Use of Adeno-Associated Virus as a Vector for Human Gene Therapy," Hum. Gene Ther. 5(7):793-801.

Krol, J. et al. (Sep. 2010, e-pub. Jul. 7, 2010). "The Widespread Regulation of MicroRNA Biogenesis, Function and Decay," Nat. Rev. Genet. 11:597-610.

Lagos-Quintana, M. et al. (Apr. 30, 2002). "Identification of tissue-specific MicroRNAs from Mouse," Curr. Biol. 12:735-739.

Lansbury, P.T. et al. (Oct. 19, 2006). "A Century-Old Debate on Protein Aggregation and Neurodegeneration Enters the Clinic," Nature 443:774-779.

Machida, Y. et al. (Apr. 28, 2006, e-pub Mar. 6, 2006). "rAAV-Mediated shRNA Ameliorated Neuropathology in Huntington Disease Model Mouse," Biochem. Bio phys. Res. Commun. 343(1):190-197.

Magari, S.R. et al. (1997). "Pharmacologic Control of a Humanized Gene Therapy System Implanted into Nude Mice," J Clin. Invest. 100:2865-2872.

Manservigi, R. et al. (2010). "HSV Recombinant Vectors for Gene Therapy," Open Virol. J. 4:123-156.

Martin, J. et al. (Aug. 2013, e-pub. Aug. 9, 2013). "Generation and Characterization of Adeno-Associated Virus Producer Cell Lines for Research and Preclinical Vector Production," Human Gene Therapy Methods 24(4):253-269.

Matsui, M. et al. (May 2012). "Allele-selective inhibition of trinucleotide repeat genes," Drug Discov. Today 17(9-10):443-450.

McBride, J.L. et al. (Apr. 15, 2008). "Ailincial miRNAs mitigate shRNA-mediated toxicity in the brain: Implications for the therapeutic development of RNAi," Proc. Natl. Acad. Sci. USA 105(15):5868-5873.

McBride, J.L. et al. (Dec. 2011). "Preclinical Safety of RNAi-Mediated HTT Suppression in the Rhesus Macaque as a Potential Therapy for Huntington's Disease," Mol. Ther. 19(12):2152-2162.

McLaughlin, S.K. et al. (Jun. 1988). "Adeno-Associated Virus General Transduction Vectors: Analysis of Proviral Structures," J. Virol. 62(6):1963-1973.

Meignier, B. et al. (May 1987). "Immunization of Experimental Animals with Reconstituted Glycoprotein Mixtures of Herpes Simplex Virus 1 and 2: Protection Against Challenge with Virulent Virus," J. Infect. Dis. 155(5):921-930.

Miniarikova, J. et al. (Aug. 3, 2017). "AAV5-miHTT Gene Therapy Demonstrates Suppression of Mutant Huntingtin Aggregation and Neuronal Dysfunction in a Rat Model of Huntington's Disease," Gene Therapy 24(10):330-639.

Miniarikova, J. et al. (Jan. 1, 2016). "Design, Characterization, and Lead Selection of Therapeutic miRNAs Targeting Huntingtin for Development of Gene Therapy for Huntington's Disease," Molecular Therapy-Nucleic Acids 5:e297, 16 pages.

Mittoux, V. et al. (Jun. 1, 2002). "Corticostriatopallidal Neuroprotection by Adenovirus-Mediated Ciliary Neurotrophic Factor Gene Transfer in a Rat Model of Progressive Striatal Degeneration", J. Neurosci. 22:4478-4486.

Miyagishi, M. et al. (Jul. 2004). "Optimization of an siRNA-expression systems with an improved hairpin and its significant suppressive effects in mammalian cells", Journal of Gene Medicine 6:715-723.

Miyazaki, J. et al. (Jul. 15, 1989). "Expression Vector System Based on the Chicken Beta-Actin Promoter Directs Efficient Production of Interleukin-5," Gene 79(2):269-277.

Niwa, H. et al. (Dec. 15, 1991). "Efficient Selection for High-Expression Transfectants with a Novel Eukaryotic Vector," Gene 108(2):193-200.

No, D. et al. (Apr. 1996). "Ecdysone-Inducible Gene Expression in Mammalian Cells and Transgenic Mice," Proc. Natl. Acad. Sci. USA 93:3346-3351.

Passini, M.A. et al. (Dec. 2001). "Widespread Gene Delivery and Structure-Specific Patterns of Expression in the Brain after Intraventricular Injections of Neonatal Mice with an Adeno-Associated Virus Vector," J. Viral. 75(24):12382-12392.

Passini, M.A. et al. (Jun. 2003). "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice," J. Virol. 77(12):7034-7040.

Pechan, P. et al. (Jan. 2009, e-pub. Jul. 17, 2008). "Novel Anti-VEGF Chimeric Molecules Delivered by AAV Vectors for Inhibition of Retinal Neovascularization," Gene Ther. 16(1):10-16.

Pfister, E. L. et al. (2017). "Safe and Efficient Silencing With a Pol II, But Not a Pol III, Promoter Expressing an Artificial Mirna Targeting Human Huntingtin," Molecular Therapy-Nucleic Acids 6(7):324-334.

Piccioli, P. et al. (1991). "Neuroantibodies: Molecular Cloning of a Monoclonal Antibody Against Substance P for Expression in the Central Nervous System," Proc. Natl. Acad. Sci. IDSA 88:5611-5615.

Piccioli, P. et al. (Aug. 1995). "Neuroantibodies: Ectopic Expression of a Recombinant Anti-Substance P Antibody in the Central Nervous System of Transgenic Mice," Neuron 15:373-384.

Porsolt, R.D. et al. (Oct. 1977). "Behavioral Despair in Mice: A Primary Screening test for Antidepressants," Arch. Int. Pharmacodyn. Ther. 229(2):327-336.

Pouladi, M. et al. (May 15, 2012, e-pub. Feb. 9, 2012). "Marked Differences in Neurochemistry and Aggregates Despite Similar Behavioural and Neuropathological Features of Huntington Disease in the Full-Length BACHD and YAC128 Mice," Hum. Mol.Genet. 21(10):2219-2232.

Pouladi, M.A. et al. (2009). "Prevention of Depressive Behaviour in the YAC128 Mouse Model of Huntington Disease by Mutation at Residue 586 of Huntingtin," Brain 132:919-932.

Ramaswamy, S. et al. (2007). "Animal Models of Huntington's Disease," Ilar J. 48(4):356-373.

Reiner, A. et al. (Dec. 2003). "Wild-Type Huntingtin Plays a Role in Brain Development and Neuronal Survival", Mol. Neurobiol. 28(3):259-276.

(56) References Cited

OTHER PUBLICATIONS

Richfield, E.K. et al. (Mar. 1995). "Reduced expression of Preproenkephalin in Striatal Neurons from Huntington's Disease Patients", Ann. Neural. 37:335-343.
Rodriguez-Lebron, E. et al. (Oct. 2005). "Intrastriatal rAAV-Mediated Delivery of Anti-huntingtin shRNAs Induces Partial Reversal of Disease Progression in R6/1 Huntington's Disease Transgenic Mice", Mol. Ther. 12(4):618-633.
Rosano, G.L. et al. (Apr. 2014, e-pub. Apr. 17, 2014). "Recombinant Protein Expression in *Escherichia coli*: Advances and Challenges," Frontiers in Microbiology 5(Article 172):1-17.
Rosas, H.D. et al. (2002). "Regional and Progressive Thinning of the Cortical Ribbon in Huntington's Disease", Neurology 58(5):695-701.
Sah, D.W.Y. et al. (Feb. 1, 2011). "Oligonucleotide Therapeutic Approaches for Huntington Disease", J. Clin. Invest. 121(2):500-507.
Samaniego, L.A. et al. (Apr. 1998). "Persistence and Expression of the Herpes Simplex Virus Genome in the Absence of Immediate-Early Proteins", J. Virol. 72(4):3307-3320.
Saudou, F. et al. (Oct. 2, 1998). "Huntingtin Acts in the Nucleus to Induce Apoptosis But Death Does Not Correlate with the Formation of Intranuclear Inclusions", Cell 95(1):55-66.
Schaffar, G. et al. (Jul. 2, 2004). "Cellular Toxicity of Polyglutamine Expansion Proteins: Mechanism of Transcription Factor Deactivation", Mol. Cell. 15(1):95-105.
Scherzinger, E. et al. (Aug. 8, 1997). "Huntingtin-Encoded Polyglutamine Expansions form Amyloid-Like Protein Aggregates in vitro and in vivo", Cell 90(3):549-558.
Segura, M.M. et al. (Jul. 2013, e-pub. E-pub. Apr. 16, 2013). "New Developments in Lentiviral Vector Design, Production and Purification," Expert Opin Biol Ther. 13(7):987-1011.
Slow, E. et al. (Jul. 1, 2003). "Selective Striatal Neuronal Loss in a YAC128 Mouse Model of Huntington Disease," Hum. Mol. Genet. 12(13):1555-1567.
Stanek L. et al. (May 2014). "Silencing Mutant Huntingtin by Adeno Associated Virus-Mediated RNA Interference Ameliorates Disease Manifestations in the YAC128 Mouse Model of Huntington's Disease," Hum Gene Ther. 25:461-474.
Sugars, K.L. et al. (Feb. 6, 2004, e-pub Nov. 18, 2003). "Decreased cAMP Response Element-Mediated Transcription: An Early Event in Exon 1 and Full-Length Cell Models of Huntington's Disease that Contributes to Polyglutamine Pathogenesis", J. Biol. Chem. 279(6):4988-4999.
Tatsis, N. et al. (Oct. 2004, e-pub Aug. 14, 2004). "Adenoviruses as Vaccine Vectors", Mol. Ther. 10 (4):616-629.
Terasawa, K. et al. (2011, e-pub Jul. 12, 2011). "Synthetic Pre-miRNA-Based shRNA as Potent RNAi Triggers", Journal of Nucleic Acids 2011:131579, 6 pages.
Treleaven, C.M. et al. (Sep. 4, 2012, e-pub Jun. 26, 2012). "Gene Transfer to the CNS Is Efficacious in Immune-primed Mice Harboring Physiologically Relevant Titers of Anti-AAV Antibodies", Mol. Ther. 20(9):1713-1723.
Van Raamsdonk, J.M. et al. (2005, e-pub Nov. 2005). "Selective Degeneration and Nuclear Localization of Mutant Huntingtin in the YAC128 Mouse Model of Huntington Disease", Hum. Mal. Genet. 14(24):3823-3835.
Van Raamsdonk, J.M. et al. (Apr. 2007, e-pub Dec. 29, 2006). "Phenotypic Abnormalities in the YAC128 Mouse Model of Huntington Disease are Penetrant on Multiple Genetic Backgrounds and Modulated by Strain", Neurobiol Dis. 26(1):189-200.
Veldwijk, M.R. et al. (Aug. 2002). "Development and Optimization of a Real-Time Quantitative PCR-Based Method for the Titration of AAV-2 Vector Stocks", Mol. Ther. 6(2):272-278.
Von Horsten, S. et al. (Mar. 15, 2003). "Transgenic Rat Model of Huntington's Disease," Hum. Mol. Genet. 12(6):617-624.
Vonsattel, J.P. et al. (Nov. 1985). "Neuropathological Classification of Huntington's Disease", J. Neuropathol. Exp. Neural. 44(6):559-577.
Wang, Y. et al. (Mar. 1997). "Ligand-Inducible and Liver-Specific Target Gene Expression in Transgenic Mice", Nat. Biotech. 15(3):239-243.
Wang, Y. et al. (May 1997). "Positive and Negative Regulation of Gene Expression in Eukaryotic Cells with an Inducible Transcriptional Regulator", Gene Ther. 4(5):432-441.
Wang, Z. et al. (Dec. 2003). "Rapid and Highly Efficient Transduction by Double-Stranded Adeno-Associated Mirus Vectors In Vitro and In Vivo," Gene Ther 10(26):2105-2111.
Written Opinion of the International Searching Authority dated Aug. 8, 2016, for PCT Application No. PCT/US2016/017207, filed on Feb. 9, 2016, 11 pages.
Written Opinion of the International Searching Authority dated Jan. 7, 2019, for PCT Application No. PCT/US2018/052221, filed on Sep. 21, 2018, five pages.
Wyatt, J. R. et al. (Oct. 1989). "RNA Folding: Pseudoknots, Loops and Bulges," Bioessays 11(4):100-106.
Xia, L. et al. (Jan. 1, 2008). "miR-15b And miR-16 Modulate Multidrug Resistance by Targeting BCL2 in Human Gastric Cancer Cells", International Journal of Cancer 123(2):372-379.
Xiao, X. et al. (Mar. 1997). "Gene Transfer by Adeno-Associated Virus Vectors into the Central Nervous System", Exp. Neurobiol. 144(1):113-124.
Xiao, X. et al. (Mar. 1998). "Production of High-Titer Recombinant Adeno-Associated Virus Vectors in the Absence of Helper Adenovirus," J Virol. 72(3):2224-2232.
Yamamoto, A. et al. (Mar. 21, 2000). "Reversal of Neuropathology and Motor Dysfunction in a Conditional Model of Huntington's Disease", Cell 101(1):57-66.
Yang, J.S. et al. (Aug. 10, 2010). "Conserved Vertebrate miR451 Provides a Platform for Dicer-independent, Ago2-mediated MicroRNA Biogenesis," Proceedings of the National Academy of Sciences 107(34):15163-15168.
Yang, S.H. et al. (Jun. 12, 2008, e-pub. May 18, 2008). "Towards a Transgenic Model of Huntington's Disease in a Non-Human Primate," Nature 453(7197):921-924.
Yoda, M. et al. (Nov. 1, 2013). "Poly(A)-Specilic Ribonuclease Mediates 3'-End Trimming of Argonaute2-Cleaved Precursor MicroRNAs," Cell Reports 5(3):715-726.
Yu, D. et al. (Aug. 31, 2012). "Single-Stranded RNAs Use RNAi to Potently and Allele-Selectively Inhibit Mutant Huntingtin Expression", Cell 150(5):895-908.
Zhong, L. et al. (Jun. 3, 2008, e-pub. May 29, 2008). "Next Generation of Adeno-Associated Virus 2 Vectors: Point Mutations in Tyrosines Lead to High-Efficiency Transduction at Lower Doses," Proc Natl Acad Sci USA 105 (22):7827-7832.
Zuccato, C. et al. (Sep. 2003, Jul. 27, 2003). "Huntingtin Interacts with REST/NRSF to Modulate the Transcription of NRSE-Controlled Neuronal Genes", Nat. Genet. 35(1):76-83.

\* cited by examiner

Fig. 1C

| Fig. 1C-1 |
| Fig. 1C-2 |
| Fig. 1C-3 |
| Fig. 1C-4 |

Fig. 1C-1 pssAAV-CBA-202AT

```
                   SmaI        SmaI
                   XmaI        XmaI
                   AvaI        AvaI
  1 TTGGCCACTC CCTCTCTGCG CGCTCGCTCG CTCACTGAGG CCGCCCGGGC AAAGCCCGGG CGTCGGGCGA CCTTTGGTCG CCCGGCCTCA GTGAGCGAGC
    AACCGGTGAG GGAGAGACGC GCGAGCGAGC GAGTGACTCC GGCGGGCCCG TTTCGGGCCC GCAGCCCGCT GGAAACCAGC GGGCCGGAGT CACTCGCTCG
                                                                                       BamHI
101 GAGCGGCGCAG AGAGGGAGTG GCCAACTCCA TCACTAGGGG TTCCTCTATA TTACCCTGCT AGGCAATTGG ATCCCGGACC GTCGACATTG ATTATTGACT
    CTCGCCGCGTC TCTCCCTCAC CGGTTGAGGT AGTGATCCCC AAGGAGATAT AATGGGACGA TCCGTTAACC TAGGGCCTGG CAGCTGTAAC TAATAACTGA
201 AGTTATTAAT AGTAATCAAT TACGGGGTCA TTAGTTCATA GCCCATATAT GGAGTTCCGC GTTACATAAC TTGACGTAAA TGGCCCGCCT GGCTGACCGC
    TCAATAATTA TCATTAGTTA ATGCCCCAGT AATCAAGTAT CGGGTATATA CCTCAAGGCG CAATGTATTG AACTGCAGTT ACCGGGCGGA CCGACTGGCG
301 CCAACGACCC CCGCCCATTG ACGTCAATAA TGACGTATGT TCCCATAGTA ACGCCAATAG GGACTTTCCA TTGACGTCAA TGGGTGGAGT ATTTACGGTA
    GGTTGCTGGG GGCGGGTAAC TGCAGTTATT ACTGCATACA AGGGTATCAT TGCGGTTATC CCTGAAAGGT AACTGCAGTT ACCCACCTCA TAAATGCCAT
401 AACTGCCCAC TTGGCAGTAC ATCAAGTGTA TCATATGCCA AGTACGCCCC CTATTGACGT CAATGACGGT AAATGGCCCG CCTGGCATTA TGCCCAGTAC
    TTGACGGGTG AACCGTCATG TAGTTCACAT AGTATACGGT TCATGCGGGG GATAACTGCA GTTACTGCCA TTTACCGGGC GGACCGTAAT ACGGGTCATG
```

```
                                                                     NcoI
                                                                     ~~~~~~~~
 501  ATGACCTTAT GGGACTTTCC TACTTGGCAG TACATCTTACG TATTAGTCAT CGCTATTACC ATGGTCGAGG TGAGCCCCAC GTTCTGCTTC ACTCTCCCCA
      TACTGGAATA CCCTGAAAGG ATGAACCGTC ATGTAGATGC ATAATCAGTA GCGATAATGG TACCAGCTCC ACTCGGGGTG CAAGACGAAG TGAGAGGGGT

601  TCTCCCCACCC CTCCCCACCC CCAATTTTGT TTTTTAATTA AAAATTAATA TTTTGTGCAG CGATGGGGGC GGGGGGGGGG CGCCAGGCGG
      AGAGGGGGGG GAGGGGTGGG GGTTAAAACA AAAATTAATT TTTTATTTAT AAACACGTC GCTACCCCCC CCCCCGCCC GCGGTCCGCC

701  GCGGGGGCGG GCGGAGGGGC GAGGGGGAGA GGTGCGGAGC CAGGCCAATCA GAGCGGCGCG CTTCGAAAGT TTCCTTTTAT GGCGAGGCGG
      CGCCCCGCCC CGCTCCCCG CTCCCGCTCT CCACGCCGCC GTCGGTTAGT CTCGCCGCGC GAAGCTTTCA AAGGAAAATA CCGCTCCGCC

801  CGGGGGCGGGC GCCCCTATAA AAAGGCGAAGC GCGCGGCGGG TGCCGGCCTGC CGCCCCCCCG TGCCCCGCTC CGCCGCCGCC
      GCCCCCCG CGGGGATATT TTTCGCTTCG CGCGCCGCC ACGCGCCGAG GAAGCGGGGC ACGGGCGAG AGCGGCGGG

901  CGCCCCGGCT CTGACTGACC CGGTTACTCC CACAGGTGAG CGGGCGGGAC GGCCCTTCTC CTCCGGGCTG TAATTAGCGC TTGGTTTAAT GACGGCTTGT
      GCGGGGCCGA GACTGACTGG CGCAATGACC GTGTCCACTC GCCCGCCCTG CCGGGAAGAG GAGGCCCGAC ATTAATCGCG AACCAAATTA CTGCCGAACA
                                                                                              AvaI
                                                                                              ~~~~~~~~
1001  TTCTTTTTCTG TGGCTGCGTG AAAGCCTTGA GGGGCTCCGG CCGAGTTGCT GAGCACGGCC CGGCTTGCGG GTGGCGCGGG GCTCGCCGTG
      AAGAAAAAGAC ACCGACGCAC TTTCGGAACT CCCCGAGGCC GGCTCAACGA CTCGTGCCGG GCCGAAGCCC ACGCCCCCG CGAGCGGCAC

1101  AGCGGCGGTCGT GCGGCTCCGC GCTGTGAGC GCTGTGAGC CGGGGCCGCC TCGGGCCCGG CTTTTGCGC GAAACACGCG AGCCGCGCGG
      TCGCGGCCA CGCGGGCCG CGACACTCG CGACACTCG GCCCGGCGG GCGCCCCGC GAAACACGCG AGGCGTCACA CGGCTCCC TCGCCGCGC

1201  GGGGCGGTGC CCCGGGTGGC CGGGGGGGGA CAAAGGCTGC GTGCCGGGTG TGTGCGTGGG GGGGTGAGCA GGGGGTGTGG GCGGTCGGT
      CCCCGCCACG GGCGCCACG GGCCCCCGA CGCTCCCCTT GTTCCGACG CACGCGACC CCCCACTCGT CCCCACACC CGGCAGCCA

1301  CGGCTGCAA CCCCCCCTGC ACCCCCCCC CCGAGTTGCT GAGCACGGCC CGGCTTCGG CGTACGGGG TGGCGCGGG GCTCGCCGTG
      GCCCGACGTT GGGGGGGGACG TGGGGGGAGG GGCTCAACGA CTCGTGCCGG GCCGAAGCCC ACGCCCCCG CACCGGGCAC CGAGCGGGCAC
                                      AvaI
                                      ~~~~~~~~
1401  CCGGGCGGGG GGTGGCGGCA GGTGGGGGCG CGGGGCCGCC CCGGGGCCGCC TCGGGCCCGG GAGGGGGCCG CCTCCCCGG CGGAGGGCCC
      GGCCCGCCCC CCACCGCCGT CCACCCCCAC GCCCCGGCGG GGCCCGGCGG AGCCCGGAGCC CTCCCCGGC GCGCCCGGG GCCTCGCGGC

1501  CGGGCTGTCG AGCCGCGCG AGCCGCTTT ATGGTAATCG TGCGAGAGGG CGCAGGGACT TCCTTTGTCC CAAATCGTG CGGAGCCGAA
      CGCCGACAGC TCCGGCGCGC TCGGCGTCGG TAACCATTAGC ACGCTCTCCC GCGTTCCCTGA AGGAAACAGG GTTTAGACAC GCCTCGGCTT
```

Fig. 1C-2

```
1601  ATCTGGGAGG CGCCGCCGCA CCCCCTCTAG CGGGCGCGGG GCGAAGCGGT GCGGCGCCCG CAGGAAGGAA ATGGGCGGGG AGGGCCTTCG TGCCGTCGCCG
      TAGACCCTCC GCGGCGGCGT GGGGGAGATC GCCCGCGCCC CGCTTCGCCA CGCCGCGGCC GTCCTTCCTT TACCCGCCCC TCCCGGAAGC ACGCAGCGGC
                                              AvaI

1701  CGGCGCCGTC CCCTTCTCCC TCTCCAGCCT CGGGGCCTGTC CGGCTGCCTT CGGGGGGGGA CGGCTGCCTT CGGGGGGGGA GGGCAAGGC GGGGTTCGG TTCTGGCGTG
      GCCGCGGCAG GGGAAGAGGG AGAGGTCGGA GCCCGACACAG GCCCGACGGA GCCCCGACGGA GCCCCGACGGA CCCGTTCCG CCCAAGCCG AAGACCCGAC

1801  TGACCCGGCGG CTCTAGAGCC TCTGCTAACC ATGTTCATGC CTTCTTCTTT TCCTACACGC TCCTGGGCAA CGTGCTGGTT ATTGTGCTGT CTCATCATTT
      ACTGGCCGCC GAGATCTCGG AGACGATTGG TACAAGTACG AAGAAGAAA AGGATGTGCG AGGACCCGTT GCACGACCAA TAACACGACA GAGTAGTAAA
              EcoRI
                                                                                          start of 207 Guide Strand
1901  TGGCAAAGAA TTCTTCGAAA GATCTGCTAG CCTGGAGGCT TGCTGAAGGC TGTATGCTGA GTCGGTGTGG TTGACAAGCA GTTTTGGCCA CTGACTGACT
      ACCGTTTCTT AAGAAGCTTT CTAGACGATC GGACCTCCGA ACGACTTCCG ACATACGACT CAGCCACACC AACTGTTCGT CAAACCGGT GACTGACTGA 2001  GCTTGATCCCA CACCGACTCA GGACACAAGG CCTGTTACTA GCACTCACAT GGAACAAATG GCCATGCATC TAGAGGGCCC TATTCTATAG AAGGTGCCAC
      CGAACAGGGT GTGGCTGAGT CCTGTGTTCC GGACAATGAT CGTGAGTGTA CCTTGTTTAC CGGTACGTAG ATCTCCCGGG ATAAGATATC TTCCACGGTG 2101  ATGCTAGAGC TCGGCTGATCA GCCTCGACTG TGCCTTCTAG TTGCCAGCCA TCTGTGTTT AGACAACAAA CGGGAGGGG GCACGAAGG TTGACCCTGG CAGCAAGGGG
      TACGATCTCG AGCCGACTAGT CGGAGCTGAC ACGGAAGATC AACGGTCGGT AGACAACAAA CGGGAGGGG GCACGAAGG AACTGGACC TTCCACGGTG GTCGTTCCCC 2201  TCCCACTGTC CTTTTCCTAAT AAAATGAGGA AATTGCATCG CATTGTCTGA GTAGGTGTCA TTCTATTCTG GGGGGTGGGG TGGGGCAGGA CAGCAAGGGG
      AGGGTGACAG GAAAGGATTA TTTTACTCCT TTAACGTAGC GTAACAGACT CATCCACAGT AAGATAAGAC CCCCACCCC ACCCCGTTCT GTCGTTCCCC 2301  GAGGATTGGG AAGACAATAG CAGGCATGCT GGGGAGCTAG AGTCGACCGG ACCGGTGGAA GTCCTCTTCC TGGTGTCCT TGACTTCAAA GGGTCTCTCC
      CTCCTAACCC TTCTGTTATC GTCCGTACGA CCCCTCGATC TCAGCTGGCC TGGCCACCTT CAGGAGAAGG AGCCACAGGA ACTGAAGTTT CCCAGGAGG 2401  CATTTGCCTG GAGAGAGGGG AAGGTGGGCA TCACCAGGGG TTTGGAAGAG TGTAGCAGAA TAAGAAACCA TGAGTCCCCT CCCTGAGAAG GGGACTCTTC
      GTAAACGGAC CTCTCTCCCC TTCCACCCGT AGTGGTCCCC ACTCACTTCC AAACCTTCTC ACATCGTCTT ATTCTTTGGT ACTTCAGGGGA CCCAGAGAG GGGACTCTTC 2501  CCCTGAGCCC CCTTGACGAC ACACATCCCT CGAGGCTCAG CTTCATCATC TGTAAAAGGT ACCATCCAAG GCTGAAACTG CTGCCGAAAA AGATTGTGTG
      GGGACTCGGG GGAACTGCTG TGTGTAGGGA GCTCCGAGTC GAAGTAGTAG ACATTTTCCA CGACTTTGAC TGGTAGGTTC GACGGCTTTT TCTAACACAC
```

Fig. 1C-3

```
2601  GGGATAATTC AAAACTAGAG GAAGATGCAG AATTTCTACA TCGTGGCGAT GTCAGGCTAA GAGATGCCAT CGTGGCTGTG CATTTTTATT GGAATCATAT
      CCCTATTAAG TTTTGATCTC CTTCTACGTC TTAAAGATGT AGCACCGCTA CAGTCCGATT CTCTACGGTA GCACCGACAC GTAAAAATAA CCTTAGTATA

2701  GTTTATTTGA GGGTGTCTTG GATATTACAA ATAAAATGTT GGAGCATCAG GCATATTTGG TACCTTCTGT CTAAGGCTCC CTGCCCCTTG TTAATTGGCA
      CAAATAAACT CCCACAGAAC CTATAATGTT TATTTTACAA CCTCGTAGTC CGTATAAACC ATGGAAGACA GATTCCGAGG GACGGGGAAC AATTAACCGT

2801  GCTCAGTTAT TCATCCAGGG CAAACATTCT GCTTACTATT CCTGAGAGCT TTCCTCATCC TCTAGATTGG CAGGGGAAAT GCAGATGCCT GGACAGCCTC
      CGAGTCAATA AGTAGGTCCC GTTTGTAAGA CGAATGATAA GGACTCTCGA AAGGAGTAGG AGATCTAACC GTCCCCTTTA CGTCTACGGA CCTGTCGGAG

2901  CCCTCTGCCA TACCAACAGA GCTTCACCAT CGAGGCATGC AGAGTGGACA GGGGCCTCAG TCCCAGCTTT CTCATTGGAC AGAAGGAGGA
      GGGAGACGGT ATGGTTGTCT CGAAGTGGTA GCTCCGTACG TCTCACCTGT CCCCGGAGTC AGGGTCGAAA GAGTAACCTG TCTTCCTCCT
                                                                        Psti
                                                                        wwwww 3001  GACTGGGGCT GGAGAGGGAC CTGGGCCCCC ACTAAGGCCA CAGCAGAGCC AGGACTTTAG TGCAGCCTGAC CTTGCCTCCA CTGCCCTCCT
      CTGACCCCGA CCTCTCCCTG GACCCGGGGG TGATTCCGGT GTCGTCTCGG TCCTGAAATC ACGTCGGACC GAACGGAGGT GACGGGAGGA 3101  TTGCCTCAAG AGCAAGGGAG CCTCAGAGTG GAGGAAGCAG CCCCTGGCCT TGCCTCCCAC CTCCCCCTCC CTATGCTGTT TTCCTGGGAC AGTGGGAGCT
      AACGGAGTTC TCGTTCCCTC GGAGTCTCAC CTCCTTCGTC GGGGACCGGA ACGGAGGGTG GAGGGGAGGG GATACGACAA AAGGACCCTG TCACCCTCGA 3201  GGCTTAGAAT GCCCTGGGGC CCCCAGGACC CTGGCATTTT AACCCCTCAG GGGCAGGAAG GCAGCCTGAG GTCCATCACC TGCTGTATGC
      CCGAATCTTA CGGGACCCCG GGGGTCCTGG GACCGTAAAA TTGGGGAGTC CCCGTCCTTC CGTCGGACTC CAGGTAGTGG ACGACATACG 3301  CACACACCAA CCCCACAGTT ACGTACTAGT TCGAAGCCAC GCGGACCGTT ATAGTTACGA GGAACCCCTA GTGATGGAGT TGGCCACTCC CTCTCTGCGC
      GTGTGTGGTT GGGGTGTCAA TGCATGATCA AGCTTCGGTG CGCCTGGCAA TATCAATGCT CCTTGGGGAT CACTACCTCA ACCGGTGAGG GAGAGACGCG
                                           SmaI              SmaI
                                           wwwwww            wwwwww
                                       XmaI              XmaI
                                       wwwwww            wwwwww
                                       AvaI              AvaI
                                       wwwwww            wwwwww 3401  GCTCGCTCGC TCACTGAGGC CGGGCGACCA AAGGTCGCCC GACGCCCGGG CTTTGCCCGG GCGCCGTCAG TGAGCGAGCG AGCGCGCAGA GAGGGAGTGG
      CGAGCGAGCG AGTGACTCCG GCCCGCTGGT TTCCAGCGGG CTGCGGGCCC GAAACGGGCC CGCGGCAGTC ACTCGCTCGC TCGCGCGTCT CTCCCTCACC

3501  CCAAAGATCT
      GGTTTCTAGA
```

Fig. 1C-4

*Significantly different from CTL3 by ANOVA, post hoc Tukey's Test

Human HTT Protein

Mouse HTT Protein

Rota Rod Test

Porsolt Swim Test

Body Weight at Sac

Brain Weight at Sac

VARIANT RNAI

CROSS-REFERENCE TO RELATED APPLICATIONS

This application is a National Phase application under 35 U.S.C. § 371 of International Application No. PCT/US2018/052221, filed Sep. 21, 2018, which claims the priority benefit of U.S. Provisional Application No. 62/561,843, filed Sep. 22, 2017, the disclosure of each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792014700SEQLIST.TXT, date recorded: Mar. 18, 2020, size: 19 KB).

FIELD OF THE INVENTION

The present invention relates to variant RNAi molecules. In some aspects, the invention relates to variant RNAi to treat Huntington's disease.

BACKGROUND

RNA interference (RNAi) has been shown to be a useful tool for gene silencing in basic research of gene function and shows great promise as a therapeutic agent to suppress genes associated with the development of a number of diseases. In nature, gene regulation by RNAi occurs through small RNAs known as microRNAs (miRNAs) (Ambros, (2004) Nature 431:350-355; Krol et al., (2010) Nat. Rev. Genet. 11:597-610). MicroRNAs have emerged as powerful regulators of diverse cellular processes, and when delivered by viral vectors, artificial miRNAs are continually expressed, resulting in a robust and sustained suppression of target genes. The elucidation of the mechanisms involved in miRNA processing has allowed scientists to co-opt the endogenous cellular RNAi machinery and direct the degradation of a target gene product with the use of artificial miRNAs (see. e.g., US PG Pub. 2014/0163214 and Davidson et al., (2012) *Cell* 150:873-875).

A hurdle to the clinical development of RNAi is the potential for off-target silencing where the seed region of the RNAi (typically nucleotides 1-7 or 1-8) pairs with sequences in non-target mRNAs in the 3' untranslated region (UTR) leading to transcript destabilization. Attempts to reduce off-target silencing include the use of algorithms to identify candidate seed sequences with high specificity for the target mRNA with minimal off-target potential (Boudreau R L et al., (2012) *Nucl. Acids Res.* 41(1):e9) and placing an internal bulge in the guide region of the RNAi (Terasawa et al., (2011) *Journal of nucleic acids* 2011:131579).

RNAi has been investigated as a therapeutic to treat Huntington's disease (HD). HD is an inherited neurodegenerative disease caused by an expansion of the CAG repeat in exon 1 of the huntingtin gene (HTT). The resulting extension of the polyglutamine tract in the N-terminal region confers a toxic gain-of-function to the mutant huntingtin protein (mHtt). The potential of silencing mHtt expression as a therapeutic strategy for HD was first demonstrated in a conditional mouse model of the disease (Yamamoto et al., (2000) *Cell* 101:57-66). When the expression of mHtt was induced in these mice, pathological and behavioral aberrations became apparent. Subsequent tetracycline-mediated repression of the mHtt transgene reversed these abnormalities, indicating that a reduction of mHtt levels allowed protein clearance mechanisms within neurons to normalize mHtt-induced changes. Hence, therapeutic strategies that reduce mHtt levels could potentially halt disease progression and alleviate HD symptoms. miRNAs that target Htt are provided in WO 2016/130589, incorporated herein in its entirety.

All references cited herein, including patent applications and publications, are incorporated by reference in their entirety.

BRIEF SUMMARY OF THE INVENTION

In some aspects, the invention provides an RNAi comprising a first strand and a second strand, wherein a) the first strand and the second strand form a duplex; b) the first strand comprises a guide region, wherein the guide region comprises the nucleic acid sequence 5'-UGGCCGUCCAUC-UUGGACCCG-3' (SEQ ID NO: 1) or 5'-AGUCGGUGUG-GUUGACAAGCA-3' (SEQ ID NO:7); and c) the second strand comprises a non-guide region. In some embodiments, the nucleic the guide region comprises the nucleic acid sequence 5'-UGGCCGUCCAUCUUGGACCCG-3' (SEQ ID NO: 1) and the non-guide region comprises the sequence 5'-CGGGUCCAAGAUGGACGGCCA-3' (SEQ ID NO:2). In some embodiments, the first strand comprises a nucleic acid sequence having about 90% identity to SEQ ID NO:1 or about 90% identity to SEQ ID NO:2. In other embodiments, the nucleic the guide region comprises the nucleic acid sequence 5'-AGUCGGUGUCGGUUGACAAGCA-3' (SEQ ID NO:7) and the non-guide region comprises the sequence 5'-UGCUUGUCAACCACACCGACU-3' (SEQ ID NO:8). In some embodiments, the second strand comprises a nucleic acid sequence having about 90% identity to SEQ ID NO:7 or about 90% identity to SEQ ID NO:8. In some embodiments of the above embodiments, the first strand and the second strand are linked by means of RNA linker capable of forming a loop structure. In some embodiments, the RNA linker comprises from 4 to 50 nucleotides. In some embodiments, the loop structure comprises 4 to 20 nucleotides. In some embodiments, the RNAi comprises 5' to 3' the second strand, the RNA linker, and the first strand. In some embodiments, the RNAi comprises 5' to 3' the first strand, the RNA linker, and the second strand. In some embodiments, the RNAi comprises the nucleic acid sequence of SEQ ID NO:4 or SEQ ID NO:10. In some embodiments, the RNAi comprises a nucleotide sequence about 90% identical to the nucleotide sequence of SEQ ID NO:4 or SEQ ID NO: 10. In some embodiments, the RNAi is a small inhibitory RNA (siRNA), a microRNA (miRNA), or a small hairpin RNA (shRNA). In some embodiments, the RNAi targets RNA encoding a polypeptide associated with Huntington's disease. In some embodiments, the polypeptide is huntingtin. In some embodiments, the huntingtin comprises a mutation associated with Huntington's disease.

In some embodiments of the above aspects and embodiments, the invention provides an expression construct comprising nucleic acid encoding the RNAi of any one of claims 1-16. In some embodiments, the nucleic acid encoding the RNAi comprises a miRNA scaffold. In some embodiments, the nucleic acid encoding the RNAi is operably linked to a promoter. In some embodiments, the promoter is selected from a cytomegalovirus (CMV) immediate early promoter, an RSV LTR, a MoMLV LTR, a phosphoglycerate kinase-1

(PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a β-actin promoter. In some embodiments, the expression construct further comprises a polyadenylation signal. In some embodiments, the polyadenylation signal is a bovine growth hormone polyadenylation signal, an SV40 polyadenylation signal, or a HSV TK pA.

In some embodiments, the invention provides a vector comprising the expression construct of any one of the embodiments described herein. In some embodiments, the vector is a recombinant adeno-associated virus (rAAV) vector, a recombinant adenoviral vector, a recombinant lentiviral vector or a recombinant herpes simplex virus (HSV) vector. In some embodiments, the vector is a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad. or porcine Ad type 3. In some embodiments, the recombinant adenoviral vector is derived from adenovirus serotype 2 or a variant of adenoviral serotype 5. In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In some embodiments, the vector is a rHSV vector. In some embodiments, the rHSV vector is derived from rHSV-1 or rHSV-2.

In some embodiments of the above aspects and embodiments, the vector is a rAAV vector. In some embodiments, the expression construct is flanked by one or more AAV inverted terminal repeat (ITR) sequences. In some embodiments, the expression construct is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the vector further comprises a stuffer nucleic acid. In some embodiments, the stuffer nucleic acid is located upstream or downstream of the nucleic acid encoding the RNAi. In some embodiments, the vector is a self-complementary rAAV vector. In some embodiments, the vector comprises first nucleic acid sequence encoding the RNAi and a second nucleic acid sequence encoding a complement of the RNAi, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence. In some embodiments, the invention provides a cell comprising any of vectors (e.g., rAAV vectors) described herein.

In some embodiments of the above aspects and embodiments, the invention provides a viral particle comprising any of the vectors described herein, wherein the viral particle is an AAV particle encapsidating the rAAV vector, an adenovirus particle encapsidating the recombinant adenoviral vector, a lentiviral particle encapsidating the recombinant lentiviral vector or an HSV particle encapsidating the recombinant HSV vector. In some embodiments, the viral particle is an adenovirus particle encapsidating the recombinant adenoviral vector. In some embodiments, the adenovirus particle comprises a capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the adenovirus particle comprises an adenovirus serotype 2 capsid or a variant of an adenoviral serotype 5 capsid. In some embodiments, the viral particle is a lentiviral particle encapsidating the recombinant lentiviral vector. In some embodiments, the lentiviral particle comprises a capsid pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In some embodiments, the viral particle is a HSV particle. In some embodiments, the HSV particle is a rHSV-1 particle or a rHSV-2 particle.

In some embodiments, the invention provides a recombinant AAV particle comprising any of the rAAV vectors described herein. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid, rAAV2-HBKO capsid (see WO 2015/168666, which is incorporated herein by reference). In some embodiments, the ITR and the capsid of the rAAV viral particle are derived from the same AAV serotype. In some embodiments, the ITR and the capsid of the rAAV viral particle are derived from different AAV serotypes. In some embodiments, the ITR is derived from AAV2 and the capsid of the rAAV particle is derived from AAV1. In some embodiments, the rAAV vector comprises 5' to 3' an AAV2 ITR, a promoter, nucleic acid encoding the RNAi, a polyadenylation signal, and an AAV2 ITR. In some embodiments, the promoter is a CBA promoter. In some embodiments, the polyadenylation signal is a bovine growth hormone polyadenylation signal. In some embodiments, the rAAV vector comprises 5' to 3' all or a portion (e.g., a functional portion) of an AAV2 ITR, the CBA promoter, an intron (e.g., a chimeric intron), nucleic acid encoding the RNAi, a bovine growth hormone polyadenylation signal, and an AAV2 ITR. In some embodiments, the vector further comprises a stuffer nucleic acid. In some embodiments, the stuffer nucleic acid further comprises nucleic acid encoding a reporter polypeptide (e.g., green fluorescent protein (GFP)). In some embodiments, the stuffer nucleic acid is located upstream or downstream of the nucleic acid encoding the RNAi.

In some embodiments, the invention provides a composition (e.g., a pharmaceutical composition) comprising any of the viral particles (e.g., rAAV particles) described herein.

In some embodiments, the composition further comprises a pharmaceutically acceptable carrier.

In some aspects, the invention provides a kit comprising any of the RNAi described herein. In some embodiments, the kit comprises any of the viral particles (e.g., rAAV particles) described herein. In some embodiments, the kit comprises any of the compositions described herein. In some embodiments, the kit further comprises instructions for use.

In some aspects, the invention provides methods for treating Huntington's disease in a mammal comprising administering to the mammal an RNAi comprising a first strand comprising a first nucleic acid comprising the sequence 5'-UGGCCGUCCAUCUUCGACCCG-3' (SEQ ID NO: 1) and a second strand comprising a second nucleic acid comprising the sequence 5'-CGGGUC-CAAGAUGGACGGCCA-3' (SEQ ID NO:2) or a first strand comprising a first nucleic acid comprising the sequence 5'-AGUCGGUGUGGUUGACAAGCA-3' (SEQ ID NO:7) and a second strand comprising a second nucleic acid comprising the sequence 5'-UGCUUGUCAAC-CACACCGACU-3' (SEQ ID NO:8). In some aspects, the invention provides methods for inhibiting the expression of htt in a mammal with Huntington's disease comprising administering to the mammal an RNAi comprising a first strand comprising a first nucleic acid comprising the sequence 5'-UGGCCGUCCAUCUUGGACCCG-3' (SEQ ID NO: 1) and a second strand comprising a second nucleic acid comprising the sequence 5'-CGGGUC-CAAGAUGGACGGCCA-3' (SEQ ID NO:2) or a first strand comprising a first nucleic acid comprising the sequence 5'-AGUCGGGUGUGGUUGACAAGCA-3' (SEQ ID NO:7) and a second strand comprising a second nucleic acid comprising the sequence 5'-UGCUUGU-CAACCACACCGACU-3' (SEQ ID NO: 10). In some aspects, the invention provides methods for inhibiting the accumulation of htt in a cell of a mammal with Huntington's disease comprising administering to the mammal an RNAi comprising a first strand comprising a first nucleic acid comprising the sequence 5'-UGGCCGUCCAUC-UUGGACCCG-3' (SEQ ID NO:1) and a second strand comprising a second nucleic acid comprising the sequence 5'-CGGGUCCAAGAUGGACGGCCA-3' (SEQ ID NO:2) or a first strand comprising a first nucleic acid comprising the sequence 5'-AGUCGGUGUGGUUGACAAGCA-3' (SEQ ID NO:7) and a second strand comprising a second nucleic acid comprising the sequence 5'-UGCUUGU-CAACCACACCGACU-3' (SEQ ID NO:8).

In some embodiments of the above methods, the first strand comprises a nucleic acid sequence having about 90% identity to SEQ ID NO:1 or about 90% identity to SEQ ID NO:7. In some embodiments, the second strand comprises a nucleic acid sequence having about 90% identity to SEQ ID NO:2 or about 90% identity to SEQ ID NO:8. In some embodiments, the first strand and the second strand are linked by means of RNA linker capable of forming a loop structure. In some embodiments, the RNA linker comprises from 4 to 50 nucleotides. In some embodiments, the loop structure comprises 4 to 20 nucleotides. In some embodiments, the RNAi comprises 5' to 3' the second strand, the RNA linker, and the first strand. In some embodiments, the RNAi comprises 5' to 3' the first strand, the RNA linker, and the second strand. In some embodiments, the RNAi comprises the nucleic acid sequence of SEQ ID NO:4 or SEQ ID NO:10. In some embodiments, the RNAi comprises a nucleotide sequence about 90% identical to the nucleotide sequence of SEQ ID NO:4 or SEQ ID NO: 10.

In some embodiments of the above methods, the RNAi is encoded on an expression construct. In some embodiments, the nucleic acid encoding the RNAi comprises a miRNA scaffold. In some embodiments, the nucleic acid encoding the RNAi is operably linked to a promoter. In some embodiments, the promoter is capable of expressing the RNAi in the brain of a mammal. In some embodiments, the promoter is selected from a cytomegalovirus (CMV) immediate early promoter, a RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), a E2F promoter, a telomerase (hTERT) promoter; a cytomegalovirus enhancer/chicken beta-actin/Rabbit β-globin (CAG) promoter, an elongation factor 1-alpha promoter (EF1-alpha) promoter and a human β-glucuronidase promoter. In some embodiments, the promoter is a hybrid chicken β-actin promoter. In some embodiments, the nucleic acid further comprises all or a portion (e.g., functional portion) of an intron and a polyadenylation signal. In some embodiments, the polyadenylation signal is a bovine growth hormone polyadenylation signal, and the intron is a chimeric intron.

In some embodiments of the above methods, the RNAi is encoded on a vector comprising the expression construct of any one of the embodiments described herein. In some embodiments, the vector is a recombinant adeno-associated virus (rAAV) vector, a recombinant adenoviral vector, a recombinant lentiviral vector or a recombinant herpes simplex virus (HSV) vector. In some embodiments, the vector is a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5. In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In some embodiments, the vector is a rHSV vector. In some embodiments, the rHSV vector is derived from rHSV-1 or rHSV-2.

In some embodiments of the above methods, the vector is a rAAV vector. In some embodiments, the expression construct is flanked by one or more AAV inverted terminal repeat (ITR) sequences. In some embodiments, the expression construct is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the vector further comprises a stuffer nucleic acid. In some embodiments, the stuffer nucleic acid is located between the promoter and the nucleic acid encoding the RNAi. In some embodiments, the vector is a self-complementary rAAV vector. In some embodiments, the vector comprises first nucleic acid sequence encoding the RNAi and a second nucleic acid sequence encoding a complement of the RNAi, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence. In some embodiments, the invention provides a cell comprising any of vectors (e.g., rAAV vectors) described herein.

In some embodiments of the above methods, vector encoding the RNAi is in a viral particle, wherein the viral particle is an AAV particle encapsidating the rAAV vector, an adenovirus particle encapsidating the recombinant adenoviral vector, a lentiviral particle encapsidating the recombinant lentiviral vector or an HSV particle encapsidating the recombinant HSV vector. In some embodiments, the viral particle is an adenovirus particle encapsidating the recombinant adenoviral vector. In some embodiments, the adenovirus particle comprises a capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the adenovirus particle comprises an adenovirus serotype 2 capsid or a variant of an adenoviral serotype 5 capsid. In some embodiments, the viral particle is a lentiviral particle encapsidating the recombinant lentiviral vector. In some embodiments, the lentiviral particle comprises a capsid pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In some embodiments, the viral particle is a HSV particle. In some embodiments, the HSV particle is a rHSV-1 particle or a rHSV-2 particle.

In some embodiments of the above methods, the invention provides a recombinant AAV particle comprising any of the rAAV vectors described herein. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the ITR and the capsid of the rAAV viral particle are derived from the same AAV serotype. In some embodiments, the ITR and the capsid of the rAAV viral particle are derived from different AAV serotypes. In some embodiments, the ITR is derived from AAV2 and the capsid of the rAAV particle is derived from AAV1. The invention provides a vector comprising the expression construct of any one of the embodiments described herein. In some embodiments, the vector is a recombinant adeno-associated virus (rAAV) vector, a recombinant adenoviral vector, a recombinant lentiviral vector or a recombinant herpes simplex virus (HSV) vector. In some embodiments, the vector is a recombinant adenoviral vector. In some embodiments, the recombinant adenoviral vector is derived from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the recombinant adenoviral vector is derived from adenovirus serotype 2 or a variant of adenoviral serotype 5. In some embodiments, the vector is a recombinant lentiviral vector. In some embodiments, the recombinant lentiviral vector is derived from a lentivirus pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In some embodiments, the vector is a rHSV vector. In some embodiments, the rHSV vector is derived from rHSV-1 or rHSV-2.

In some embodiments of the above aspects and embodiments, the vector is a rAAV vector. In some embodiments, the expression construct is flanked by one or more AAV inverted terminal repeat (ITR) sequences. In some embodiments, the expression construct is flanked by two AAV ITRs. In some embodiments, the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs. In some embodiments, the AAV ITRs are AAV2 ITRs. In some embodiments, the vector further comprises a stuffer nucleic acid. In some embodiments, the stuffer nucleic acid is located between the promoter and the nucleic acid encoding the RNAi. In some embodiments, the vector is a self-complementary rAAV vector. In some embodiments, the vector comprises first nucleic acid sequence encoding the RNAi and a second nucleic acid sequence encoding a complement of the RNAi, wherein the first nucleic acid sequence can form intrastrand base pairs with the second nucleic acid sequence along most or all of its length. In some embodiments, the first nucleic acid sequence and the second nucleic acid sequence are linked by a mutated AAV ITR, wherein the mutated AAV ITR comprises a deletion of the D region and comprises a mutation of the terminal resolution sequence. In some embodiments, the invention provides a cell comprising any of vectors (e.g., rAAV vectors) described herein.

In some embodiments of the above aspects and embodiments, the invention provides a viral particle comprising any of the vectors described herein, wherein the viral particle is an AAV particle encapsidating the rAAV vector, an adenovirus particle encapsidating the recombinant adenoviral vector, a lentiviral particle encapsidating the recombinant lentiviral vector or an HSV particle encapsidating the recombinant HSV vector. In some embodiments, the viral particle is an adenovirus particle encapsidating the recombinant adenoviral vector. In some embodiments, the adenovirus particle comprises a capsid from Adenovirus serotype 2, 1, 5, 6, 19, 3, 11, 7, 14, 16, 21, 12, 18, 31, 8, 9, 10, 13, 15, 17, 19, 20, 22, 23, 24-30, 37, 40, 41, AdHu2, AdHu 3, AdHu4, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad, or porcine Ad type 3. In some embodiments, the adenovirus particle comprises an adenovirus serotype 2 capsid or a variant of an adenoviral serotype 5 capsid. In some embodiments, the viral particle is a lentiviral particle encapsidating the recombinant lentiviral vector. In some embodiments, the lentiviral particle comprises a capsid pseudotyped with vesicular stomatitis virus (VSV), lymphocytic choriomeningitis virus (LCMV), Ross river virus (RRV), Ebola virus, Marburg virus, Mokala virus, Rabies virus, RD114 or variants therein. In some embodiments, the viral particle is a HSV particle. In some embodiments, the HSV particle is a rHSV-1 particle or a rHSV-2 particle.

In some embodiments, the invention provides a recombinant AAV particle comprising any of the rAAV vectors described herein. In some embodiments, the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the ITR and the capsid of the rAAV viral particle are derived from the same AAV serotype. In some embodiments, the ITR and the capsid of the rAAV viral particle are derived from different AAV serotypes. In some embodiments, the ITR is derived from AAV2 and the capsid of the rAAV particle is derived from AAV1. In some embodiments, the rAAV vector comprises 5' to 3' an AAV2 ITR, a promoter, nucleic acid encoding the RNAi, a polyadenylation signal, and an AAV2 ITR. In some embodiments, the promoter is a CBA promoter. In some embodiments, the polyadenylation signal is a bovine growth hormone polyadenylation signal. In some embodiments, the rAAV vector comprises 5' to 3' an AAV2 ITR, the CBA promoter, an intron, nucleic acid encoding the RNAi, a bovine growth hormone polyadenylation signal, and an AAV2 ITR. In some embodiments, the vector further comprises a stuffer nucleic acid. In some embodiments, the stuffer nucleic acid comprises nucleic acid encoding a green fluorescent protein (GFP). In some embodiments, the stuffer nucleic acid is located between the promoter and the nucleic acid encoding the RNAi.

In some embodiments of the above methods, the viral particle (e.g., the rAAV particle) is in a composition (e.g., a first pharmaceutical composition). In some embodiments, the composition further comprises a pharmaceutically acceptable carrier.

BRIEF DESCRIPTION OF THE DRAWINGS

FIG. 1C shows the sequence of the coding strand of ssAAV2/1miRHtt.de (SEQ ID NO: 16) and the noncoding strand of ssAAV2/1miRHtt.de (SEQ ID NO:19).

FIG. 6 * indicate a significant deficiency in CTL3 noncoding miRNA control mice, p<0.05; ANOVA followed by Tukey's post-hoc test compared to wild type mice, wild type mice treated with AAV2/1-miRNA-Htt-207, and YAC128 mice treated with AAV2/1-miRNA-Htt-207.

DETAILED DESCRIPTION

Figure 1A:
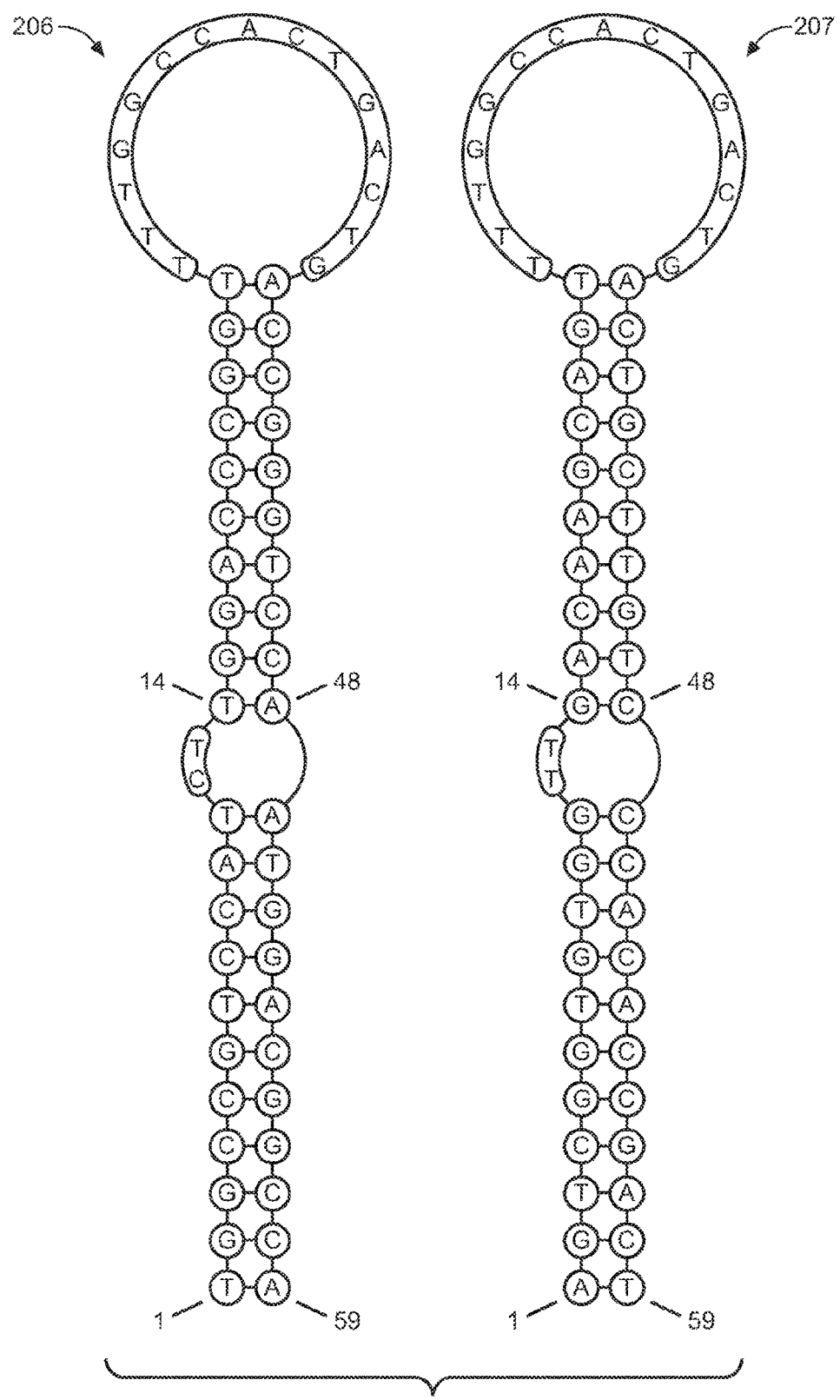
FIG. 1A shows a DNA sequence for Htt miRNA 206 (SEQ ID NO:22) and Htt miRNA 207 (SEQ ID NO:9).
Figure 1B:
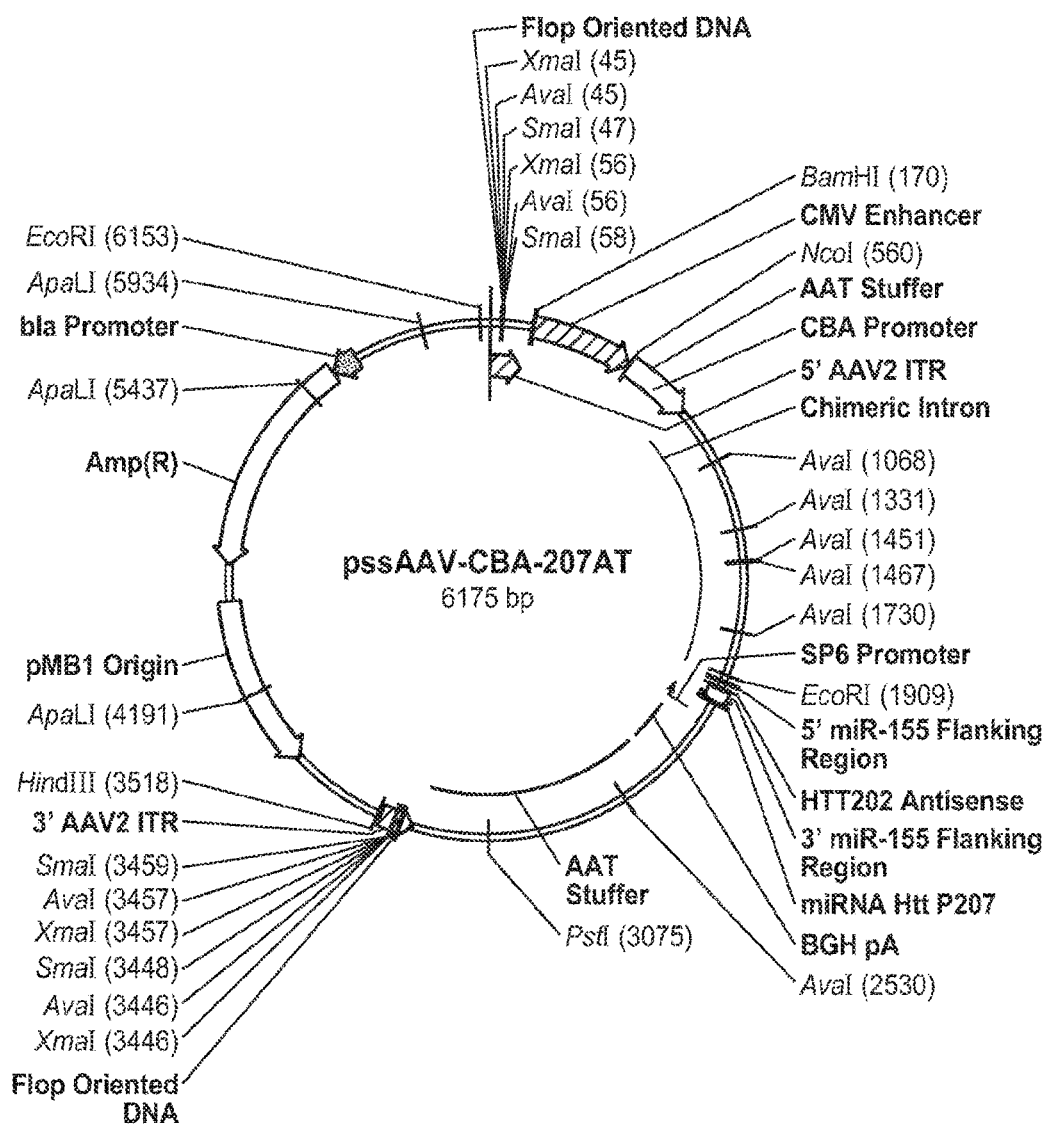
FIG. 1B shows a map of ssAAV2/1miRHtt.de.

In some aspects, the invention provides RNAi for treating Huntington's disease, wherein the RNAi comprises a first strand comprising a first nucleic acid comprising the sequence 5'-UGGCCGUCCAUCUUGGACCCG-3' (SEQ ID NO: 1) and a second strand comprising a second nucleic acid comprising the sequence 5'-CGGGUC-CAAGAUGGACGGCCA-3' (SEQ ID NO:2), where the first strand and second strand form a duplex. In some aspects, the invention provides RNAi for treating Huntington's disease, wherein the RNAi comprises a first strand comprising a first nucleic acid comprising the sequence 5'-AGUCGGUGUGGUUGACAAGCA-3' (SEQ ID NO:7) and a second strand comprising a second nucleic acid comprising the sequence 5'-UGCUUGUCAAC-CACACCGACU-3' (SEQ ID NO:8), where the first strand and second strand form a duplex. In some aspects, the invention provides expression cassettes, vectors (e.g., recombinant AAV, adenoviral, lentiviral, or HSV vectors), cells, viral particles (e.g., AAV, adenoviral, lentiviral, or HSV viral particles), and pharmaceutical compositions comprising an RNAi of the present disclosure. In further aspects, the invention provides methods for treating Huntington's disease, inhibiting the expression of htt, and inhibiting the accumulation of htt in a cell in a mammal comprising administering to the mammal a pharmaceutical composition comprising an RNAi of the present disclosure. In still further aspects, the invention provides for the use of a pharmaceutical composition comprising an RNAi of the present disclosure to treat Huntington's disease (e.g., ameliorate the symptoms of Huntington's disease), inhibit the expression of htt, or inhibit the accumulation of htt in a cell in a mammal with Huntington's disease. In yet further aspects, the invention provides kits for treating Huntington's disease in a mammal comprising an RNAi of the present disclosure.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); Antibodies (P. Finch, 1997): *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 2011).

II. Definitions

A "vector." as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—NH$_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one, and in some embodiments two, inverted terminal repeat sequences (ITRs).

A "recombinant AAV vector (rAAV vector)" refers to a polynucleotide vector comprising one or more heterologous sequences (i.e., nucleic acid sequence not of AAV origin) that are flanked by at least one, and in some embodiments two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. A rAAV vector can be in any of a number of forms, including, but not limited to, plasmids, linear artificial chromosomes, complexed with lipids, encapsulated within liposomes, and encapsidated in a viral particle, particularly an AAV particle. A rAAV vector can be packaged into an AAV virus capsid to generate a "recombinant adeno-associated viral particle (rAAV particle)".

A "recombinant adenoviral vector" refers to a polynucleotide vector comprising one or more heterologous sequences (i.e., nucleic acid sequence not of adenovirus origin) that are flanked by at least one adenovirus inverted terminal repeat sequence (ITR). In some embodiments, the recombinant nucleic acid is flanked by two inverted terminal repeat sequences (ITRs). Such recombinant viral vectors can be replicated and packaged into infectious viral particles when present in a host cell that is expressing essential adenovirus genes deleted from the recombinant viral genome (e.g., E1 genes, E2 genes, E4 genes, etc.). When a recombinant viral vector is incorporated into a larger polynucleotide (e.g., in a chromosome or in another vector such as a plasmid used for cloning or transfection), then the recombinant viral vector may be referred to as a "pro-vector" which can be "rescued" by replication and encapsidation in the presence of adenovirus packaging functions. A recombinant viral vector can be in any of a number of forms, including, but not limited to, plasmids, linear artificial chromosomes, complexed with lipids, encapsulated within liposomes, and encapsidated in a viral particle, for example, an adenovirus particle. A recombinant viral vector can be packaged into an adenovirus virus capsid to generate a "recombinant adenoviral particle."

A "recombinant lentivirus vector" refers to a polynucleotide vector comprising one or more heterologous sequences (i.e., nucleic acid sequence not of lentivirus origin) that are flanked by at least one lentivirus terminal repeat sequences (LTRs). In some embodiments, the recombinant nucleic acid is flanked by two lentiviral terminal repeat sequences (LTRs). Such recombinant viral vectors can be replicated and packaged into infectious viral particles when present in a host cell that has been infected with a suitable helper functions. A recombinant lentiviral vector can be packaged into a lentivirus capsid to generate a "recombinant lentiviral particle."

A "recombinant herpes simplex vector (recombinant HSV vector)" refers to a polynucleotide vector comprising one or more heterologous sequences (i.e., nucleic acid sequence not of HSV origin) that are flanked by HSV terminal repeat sequences. Such recombinant viral vectors can be replicated and packaged into infectious viral particles when present in a host cell that has been infected with a suitable helper functions. When a recombinant viral vector is incorporated into a larger polynucleotide (e.g., in a chromosome or in another vector such as a plasmid used for cloning or transfection), then the recombinant viral vector may be referred to as a "pro-vector" which can be "rescued" by replication and encapsidation in the presence of HSV packaging functions. A recombinant viral vector can be in any of a number of forms, including, but not limited to, plasmids, linear artificial chromosomes, complexed with lipids, encapsulated within liposomes, and encapsidated in a viral particle, for example, an HSV particle. A recombinant viral vector can be packaged into an HSV capsid to generate a "recombinant herpes simplex viral particle."

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as miRNA, siRNA, or shRNA.

"Chicken β-actin (CBA) promoter" refers to a polynucleotide sequence derived from a chicken β-actin gene (e.g., *Gallus gallus* beta actin, represented by GenBank Entrez Gene ID 396526). As used herein, "chicken β-actin promoter" may refer to a promoter containing a cytomegalovirus (CMV) early enhancer element, the promoter and first exon and intron of the chicken β-actin gene, and the splice acceptor of the rabbit beta-globin gene, such as the sequences described in Miyazaki, J. et al. (1989) *Gene* 79(2):269-77. As used herein, the term "CAG promoter" may be used interchangeably. As used herein, the term "CMV early enhancer/chicken beta actin (CAG) promoter" may be used interchangeably.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.*, 10:1031-1039; Veldwijk et al. (2002) *Mol. Ther.*, 6:272-278.

The term "vector genome (vg)" as used herein may refer to one or more polynucleotides comprising a set of the polynucleotide sequences of a vector, e.g., a viral vector. A vector genome may be encapsidated in a viral particle. Depending on the particular viral vector, a vector genome may comprise single-stranded DNA, double-stranded DNA, or single-stranded RNA, or double-stranded RNA. A vector genome may include endogenous sequences associated with a particular viral vector and/or any heterologous sequences inserted into a particular viral vector through recombinant techniques. For example, a recombinant AAV vector genome may include at least one ITR sequence flanking a promoter, a stuffer, a sequence of interest (e.g., an RNAi), and a polyadenylation sequence. A complete vector genome may include a complete set of the polynucleotide sequences of a vector. In some embodiments, the nucleic acid titer of a viral vector may be measured in terms of vg/mL. Methods suitable for measuring this titer are known in the art (e.g., quantitative PCR).

As used herein, the term "inhibit" may refer to the act of blocking, reducing, eliminating, or otherwise antagonizing the presence, or an activity of, a particular target. Inhibition may refer to partial inhibition or complete inhibition. For example, inhibiting the expression of a gene may refer to any act leading to a blockade, reduction, elimination, or any other antagonism of expression of the gene, including reduction of mRNA abundance (e.g., silencing mRNA transcription), degradation of mRNA, inhibition of mRNA translation, and so forth. In some embodiments, inhibiting the expression of HTT may refer a blockade, reduction, elimination, or any other antagonism of expression of HTT, including reduction of HTT mRNA abundance (e.g., silencing HTT mRNA transcription), degradation of HTT mRNA, inhibition of HTT mRNA translation, and so forth. As another example, inhibiting the accumulation of a protein in a cell may refer to any act leading to a blockade, reduction, elimination, or other antagonism of expression of the protein, including reduction of mRNA abundance (e.g., silencing mRNA transcription), degradation of mRNA, inhibition of mRNA translation, degradation of the protein, and so forth. In some embodiments, inhibiting the accumulation of HTT protein in a cell refers to a blockade, reduction, elimination, or other antagonism of expression of the HTT protein in a cell, including reduction of HTT mRNA abundance (e.g., silencing HTT mRNA transcription), degradation of HTT mRNA, inhibition of HTT mRNA translation, degradation of the HTT protein, and so forth The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.*, 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.*, 144:113-124; or in Fisher et al. (1996) *J. Virol.*, 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

"AAV helper functions" refer to functions that allow AAV to be replicated and packaged by a host cell. AAV helper functions can be provided in any of a number of forms, including, but not limited to, helper virus or helper virus genes which aid in AAV replication and packaging. Other AAV helper functions are known in the art such as genotoxic agents.

A "helper virus" for AAV refers to a virus that allows AAV (which is a defective parvovirus) to be replicated and packaged by a host cell. A helper virus provides "helper functions" which allow for the replication of AAV. A number of such helper viruses have been identified, including adenoviruses, herpesviruses and, poxviruses such as vaccinia and baculovirus. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV). Examples of adenovirus helper functions for the replication of AAV include E1A functions, E1B functions, E2A functions, VA functions and E4orf6 functions. Baculoviruses available from depositories include *Autographa californica* nuclear polyhedrosis virus.

A preparation of rAAV is said to be "substantially free" of helper virus if the ratio of infectious AAV particles to infectious helper virus particles is at least about $10^2$:1; at least about $10^4$:1, at least about $10^6$:1; or at least about $10^8$:1 or more. In some embodiments, preparations are also free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. A preferred alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D. and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms.

"Huntington's disease (HD)" refers to the progressive brain disorder typically caused by mutations in the HTT gene (aka huntingtin, HD or IT15). It may be characterized by symptoms including abnormal movements (termed chorea), gradual loss of motor function, emotional or psychiatric illnesses, and progressively impaired cognition. Although most symptoms appear in the 30s and 40s, juvenile forms of the disease have also been observed. For further description of HD, see OMIM Entry No. 143100.

"Huntingtin (HTI)" may refer either to the gene or to a polypeptide product thereof associated with most cases of Huntington's disease. The normal function of huntingtin is not fully understood. However, mutations in the huntingtin gene are known to cause HD. These mutations are typically inherited in an autosomal dominant fashion and involve expansion of trinucleotide CAG repeats in the HTT gene, leading to a polyglutamine (polyQ) tract in the Htt protein.

As used herein, an "RNAi" may refer to any RNA molecule that induces RNA interference in a cell. Examples of RNAi include without limitation small inhibitory RNAs (siRNAs), microRNAs (miRNAs), and small hairpin RNAs (shRNAs).

"miRNA scaffold" may refer to a polynucleotide containing (i) a double-stranded sequence targeting a gene of interest for knockdown by RNAi and (ii) additional sequences that form a stem-loop structure resembling that of endogenous miRNAs. A sequence targeting a gene of interest for RNAi (e.g., a short, ~20-nt sequence) may be ligated to sequences that create a miRNA-like stem-loop and a sequence that base pairs with the sequence of interest to form a duplex when the polynucleotide is assembled into the miRNA-like secondary structure. As described herein, this duplex may hybridize imperfectly, e.g., it may contain one or more unpaired or mispaired bases. Upon cleavage of this polynucleotide by Dicer, this duplex containing the sequence targeting a gene of interest may be unwound and incorporated into the RISC complex. A miRNA scaffold may refer to the miRNA itself or to a DNA polynucleotide encoding the miRNA. An example of a miRNA scaffold is the miR-155 sequence (Lagos-Quintana, M. et al. (2002) Curr. Biol. 12:735-9). Commercially available kits for cloning a sequence into a miRNA scaffold are known in the art (e.g., the Invitrogen™ BLOCK-iT™ Pol II miR RNAi expression vector kit from Life Technologies, Thermo Fisher Scientific; Waltham, Mass.).

As used herein, a "bulge" refers to a region of nucleic acid that is non-complementary to nucleic acid opposite it in a duplex nucleic acid. For example, a bulge may refer to a nucleic acid sequence that is noncomplementary to nucleic acid opposite in a duplex nucleic acid where the bulge is flanked by regions of nucleic acid that are complementary to nucleic acid opposite in a duplex nucleic acid. In some examples, the bulge may be any of 1, 2, 3, 4, 5, 6, 7, 8, 9, 10 or greater than 10 bases in length. In some examples, the bulge may be the result of mispairing (e.g., the opposite strand contains a base that is noncomplementary) or the bulge may be the result of nonpairing (e.g., the opposite strand comprises nucleic acid complementary to nucleic acid flanking the bulge but the opposite strand does not contain nucleic acid opposite the bulge).

As used herein, the term "sense" nucleic acid is a nucleic acid comprising a sequence that encodes all or a part of a transgene. In some examples, mRNA for a transgene is a sense nucleic acid.

As used herein, "antisense" nucleic acid is a sequence of nucleic acid that is complementary to a "sense" nucleic acid. For example, an antisense nucleic acid may be complementary to a mRNA encoding a transgene.

As used herein, the "guide region" of an RNAi is the strand of the RNAi that binds the target mRNA, typically on the basis of complementarity. The region of complementarity may encompass the all or a portion of the guide region. Typically, the region of complementarity includes at least the seed region. In many cases, the antisense region of a RNAi is the guide region.

As used herein, the "passenger region," or "non-guide region," used interchangeably herein, of an RNAi is the region of the RNAi that is complementary to the guide region. In many cases, the sense region of a RNAi is the passenger region.

As used herein, the "seed region" of a RNAi (e.g., miRNA) is a region of about 1-8 nucleotides in length of a microRNA. In some examples, the seed region and the 3'-UTR of its target mRNA may be a key determinant in RNAi recognition.

As used herein, "off-target gene silencing" refers to the pairing of a seed region of an RNAi with sequences in 3'-UTRs of unintended mRNAs and directs translational repression and destabilization of those transcripts (e.g., reduces expression of the unintended mRNAs).

Reference to "about" a value or parameter herein includes (and describes) embodiments that are directed to that value or parameter per se. For example, description referring to "about X" includes description of "X."

As used herein, the singular form of the articles "a." "an," and "the" includes plural references unless indicated otherwise.

It is understood that aspects and embodiments of the invention described herein include "comprising." "consisting," and/or "consisting essentially of" aspects and embodiments.

III. RNAi

In some aspects, the invention provides improved RNAi targeting htt RNA for the treatment of Huntington's disease. In some embodiments, the RNAi is a small inhibitory RNA (siRNA), a microRNA (miRNA), or a small hairpin RNA (shRNA). A small inhibitory or interfering RNA (siRNA) is known in the art as a double-stranded RNA molecule of approximately 19-25 (e.g., 19-23) base pairs in length that induces RNAi in a cell. A small hairpin RNA (shRNA) is known in the art as an RNA molecule comprising approximately 19-25 (e.g., 19-23) base pairs of double stranded RNA linked by a short loop (e.g., ~4-11 nucleotides) that induces RNAi in a cell. In some embodiments, the RNAi comprises a first strand and a second strand, wherein a) the first strand and the second strand form a duplex; b) the first strand comprises a guide region, wherein the guide region comprises the nucleic acid sequence 5'-UGGCCGUC-CAUCUUGGACCCG-3' (SEQ ID NO:1) or 5'-AGUCG-GUGUGGUUGACAAGCA-3' (SEQ ID NO:7); and c) the second strand comprises a non-guide region. In some embodiments, the nucleic the guide region comprises the nucleic acid sequence 5'-UGGCCGUCCAUCUUGGACCCG-3' (SEQ ID NO: 1) and the non-guide region comprises the sequence 5'-CGGGUCCAAGAUGGACGGCCA-3' (SEQ ID NO:2). In other embodiments, the nucleic the guide region comprises the nucleic acid sequence 5'-AGUCGGUGUGGUUGACAAGCA-3' (SEQ ID NO:7) and the non-guide region comprises the sequence 5'-UGCUUGUCAACCACACCGACU-3' (SEQ ID NO:8).

In some embodiments, the first strand comprises a guide region, wherein the guide region comprises a nucleic acid sequence having more than about 75%, 80%, 85%, 90%, 95%, 96%, 97%, 98%, 99% identity to 5'-UGGCCGUCCAUCUUGGACCCG-3' (SEQ ID NO:1). In some embodiments, the first strand comprises a guide region, wherein the guide region comprises a nucleic acid sequence having more than about 75%, 80%, 85%, 90%, 95%, 96%, 97%, 98%, 99% identity to 5'-UGGCCGUCCAUCUUGGACCCG-3' (SEQ ID NO:1) but maintains at least one CpG motif. In some embodiments, the first strand comprises a guide region, wherein the guide region comprises a nucleic acid sequence having more than about 75%, 80%, 85%, 90%, 95%, 96%, 97%, 98%, 99% identity to 5'-AGUCGGUGUGGUUGACAAGCA-3' (SEQ ID NO:7). In some embodiments, the first strand comprises a guide region, wherein the guide region comprises a nucleic acid sequence having more than about 75%, 80%, 85%, 90%, 95%, 96%, 97%, 98%, 99% identity to 5'-AGUCGGUGUGGUUGACAAGCA-3' (SEQ ID NO:7) but maintains at least one CpG motif. In some embodiments, the second strand comprises a non-guide region, wherein the non-guide region comprises a nucleic acid sequence having more than about 75%, 80%, 85%, 90%, 95%, 96%, 97%, 98%, 99% identity to 5'-CGGGUCCAAGAUGGACGGCCA-3' (SEQ ID NO:2). In some embodiments, the second strand comprises a non-guide region, wherein the non-guide region comprises a nucleic acid sequence having more than about 75%, 80%, 85%, 90%, 95%, 96%, 97%, 98%, 99% identity to 5'-CGGGUCCAAGAUGGACGGCCA-3' (SEQ ID NO:2) but maintains at least one CpG motif. In some embodiments, the second strand comprises a non-guide region, wherein the non-guide region comprises a nucleic acid sequence having more than about 75%, 80%, 85%, 90%, 95%, 96%, 97%, 98%, 99% identity to 5'-UGCUUGUCAACCACACCGACU-3' (SEQ ID NO:8). In some embodiments, the second strand comprises a non-guide region, wherein the non-guide region comprises a nucleic acid sequence having more than about 75%, 80%, 85%, 90%, 95%, 96%, 97%, 98%, 99% identity to 5'-UGCUUGUCAACCACACCGACU-3' (SEQ ID NO:8) but maintains at least one CpG motif.

In some embodiments, the RNAi comprises the nucleic acid sequence of SEQ ID NO:4. In some embodiments, the RNAi comprises a nucleic acid sequence having more than about 75%, 80%, 85%, 90%, 95%, 96%, 97%, 98%, 99% identity to SEQ ID NO:4. In some embodiments, the RNAi comprises a nucleic acid sequence having more than about 75%, 80%, 85%, 90%, 95%, 96%, 97%, 98%, 99% identity to SEQ ID NO:4 but maintains at least one sequence (e.g., in a seed sequence). In some embodiments, the RNAi is miRNA-207. In other embodiments, the RNAi is miRNA-206.

In some embodiments, the RNAi comprises the nucleic acid sequence of SEQ ID NO: 10. In some embodiments, the RNAi comprises a nucleic acid sequence having more than about 75%, 80%, 85%, 90%, 95%, 96%, 97%, 98%, 99% identity to SEQ ID NO:10. In some embodiments, the RNAi comprises a nucleic acid sequence having more than about 75%, 80%, 85%, 90%, 95%, 96%, 97%, 98%, 99% identity to SEQ ID NO: 10 but maintains at least one CpG sequence (e.g., in a seed sequence). In some embodiments, the RNAi is miRNA-207. In some embodiments, the RNAi is miRNA-206.

A microRNA (miRNA) is known in the art as an RNA molecule that induces RNAi in a cell comprising a short (e.g., 19-25 base pairs) sequence of double-stranded RNA linked by a loop and containing one or more additional sequences of double-stranded RNA comprising one or more bulges (e.g., mispaired or unpaired base pairs). As used herein, the term "miRNA" encompasses endogenous miRNAs as well as exogenous or heterologous miRNAs. In some embodiments. "miRNA" may refer to a pri-miRNA or a pre-miRNA. During miRNA processing, a pri-miRNA transcript is produced. The pri-miRNA is processed by Drosha-DGCR8 to produce a pre-miRNA by excising one or more sequences to leave a pre-miRNA with a 5'flanking region, a guide strand, a loop region, a non-guide strand, and a 3'flanking region; or a 5'flanking region, a non-guide strand, a loop region, a guide strand, and a 3'flanking region. The pre-miRNA is then exported to the cytoplasm and processed by Dicer to yield a siRNA with a guide strand and a non-guide (or passenger) strand. The guide strand is then used by the RISC complex to catalyze gene silencing, e.g., by recognizing a target RNA sequence complementary to the guide strand. Further description of miRNAs may be found, e.g., in WO 2008/150897. The recognition of a target sequence by a miRNA is primarily determined by pairing between the target and the miRNA seed sequence, e.g., nucleotides 1-8 (5' to 3') of the guide strand (see, e.g., Boudreau, R. L. et al. (2013) *Nucleic Acids Res.* 41:e9).

In the pri/pre-miRNA structure, the guide strand:non-guide strand interface in a duplex is formed in part through complementary base pairing (e.g., Watson-Crick base pairing). However, in some embodiments, this complementary base pairing does not extend through the entire duplex. In some embodiments, a bulge in the interface may exist at one or more nucleotide positions. As used herein, the term "bulge" may refer to a region of nucleic acid that is non-complementary to the nucleic acid opposite it in a duplex. In some embodiments, the bulge is formed when the regions of complementary nucleic acids bind to each other, whereas the regions of central non-complementary region do not bind. In some embodiments, the bulge is formed when the two strands of nucleic acid positioned between the two complementary regions are of different lengths. As described below, a bulge may comprise 1 or more nucleotides.

During miRNA processing, the miRNA is cleaved at a cleavage site adjacent to the guide strand:non-guide strand interface, thus releasing the siRNA duplex of the guide and non-guide strands. In some embodiments, the miRNA comprises a bulge in the sense or antisense strand adjacent to the cleavage site. To state another way, in some embodiments, the miRNA comprises a bulge in the guide or non-guide strand adjacent to the seed sequence. See FIG. 1A.

In some embodiments, the miRNA comprises a bulge in the guide strand opposite the 5' cleavage site of the mature non-guide strand. In some embodiments, the miRNA comprises a bulge opposite the 5' nucleotide of the non-guide strand. In some embodiments, the miRNA comprises a bulge in the sense strand opposite the 3' cleavage site of the mature guide strand. In some embodiments, the miRNA comprises a bulge opposite the 3' nucleotide of the guide strand.

In some embodiments, the RNAi comprises a first strand and a second strand, wherein a) the first strand and the second form a duplex; b) the first strand comprises a guide region of at least 11 bases, wherein the guide region comprises a seed region comprising bases 1-N of the guide strand, wherein N=7 or N=8; and c) the second strand comprises a non-guide region of at least 11 bases, wherein the non-guide region comprises a bulge sequence opposite of any one or more of bases 1-(N+2) of the guide region in the duplex. In some embodiments, wherein N=7 and the bulge is opposite base 1, 2, 3, 4, 5, 6, 7, 8, or 9 of the guide region. In other embodiments, N=8 and the bulge is opposite base 1, 2, 3, 4, 5, 6, 7, 8, 9, or 10 of the guide region.

In some embodiments, the RNAi comprises a first strand and a second strand, wherein a) the first strand and the second form a duplex; b) the first strand comprises a guide region of at least 10 bases, wherein the guide region comprises a seed region comprising bases 1-N of the guide strand, wherein N=7 or N=8; and c) the second strand comprises a non-guide region of at least 10 bases, wherein the non-guide region comprises a bulge sequence opposite of any one or more of bases 1-(N+1) of the guide region in the duplex. In some embodiments, wherein N=7 and the bulge is opposite base 1, 2, 3, 4, 5, 6, 7, or 8 of the guide region. In other embodiments, N=8 and the bulge is opposite base 1, 2, 3, 4, 5, 6, 7, 8, or 9 of the guide region.

In some embodiments, the non-guide region comprises a bulge sequence opposite of any one or more of bases 1-N of the guide region in the duplex. In some embodiments, N=7 and the bulge is opposite base 1, 2, 3, 4, 5, 6 or 7 of the guide region. In other embodiments, N=8 and the bulge is opposite base 1, 2, 3, 4, 5, 6, 7 or 8 of the guide region.

In some embodiments, the RNAi comprises a first strand and a second strand, wherein a) the first strand and the second form a duplex, b) the first strand comprises a guide region of at least 9 bases, wherein the guide region comprises a seed region comprising bases 2-7 or 2-8 of the guide strand, and c) the second strand comprises a non-guide region of at least 9 bases, wherein the non-guide region comprises a bulge sequence opposite of base 1 or base 9 of the guide region in the duplex.

In some embodiments, the RNAi comprises a first strand and a second strand, wherein a) the first strand and the second form a duplex, b) the first strand comprises a guide region of at least 9 bases, wherein the guide region comprises a seed region comprising bases 2-7 or 2-8 of the guide strand, and c) the second strand comprises a non-guide region of at least 9 bases, wherein the non-guide region comprises a bulge sequence opposite of base 1 of the guide region in the duplex.

In some embodiments, the bulge is formed by one or more bases of the non-guide strand in the duplex that lack a complementary base on the guide region, wherein the bulge is flanked by bases that do basepair with the guide strand. In some embodiments, the bulge sequence has about 1-10 nucleotides. In some embodiments, the bulge sequence has about 2-15 nucleotides. In some embodiments, the bulge sequence has about 1, about 2, about 3, about 4, about 5, about 6, about 7, about 8, about 9, about 10, about 11, about 12, about 13, about 14, or about 15 nucleotides.

The safety of RNAi-based therapies can be hampered by the ability of small inhibitory RNAs (siRNAs) to bind to unintended mRNAs and reduce their expression, an effect known as off-target gene silencing. Off-targeting primarily occurs when the seed region (nucleotides 2-8 of the small RNA) pairs with sequences in 3'-UTRs of unintended mRNAs and directs translational repression and destabilization of those transcripts. Reduced off-targeting RNAi may be designed by substituting bases within the guide and nonguide sequences; e.g., by creating CpG motifs. Potential substitutions that may result in a significantly lower off-target score can be evaluated using the SiSPOTR algorithm, a specificity-focused siRNA design algorithm which identifies candidate sequences with minimal off-targeting potentials and potent silencing capacities (Boudreau et al, *Nucleic Acids Res.* 2013 January; 41(1) e9. A reduced SiSPOTR score predicts sequences that have a lower number of potential human off targets compared parent RNAi molecules. In some embodiments of the invention, the RNAi is improved to reduce off-target gene silencing. In some embodiments, the RNAi comprises one or more CpG motifs. In some embodiments, the RNAi comprises one or more CpG motifs in a seed region.

In some embodiments, the first strand and the second strand are linked by means of a RNA (e.g., a RNA linker) capable of forming a loop structure. As is commonly known in the art, an RNA loop structure (e.g., a stem-loop or hairpin) is formed when an RNA molecule comprises two sequences of RNA that basepair together separated by a sequence of RNA that does not base pair together. For example, a loop structure may form in the RNA molecule A-B-C if sequences A and C are complementary or partially complementary such that they base pair together, but the bases in sequence B do not base pair together.

In some embodiments, the RNA capable of forming a loop structure comprises from 4 to 50 nucleotides. In certain embodiments, the RNA capable of forming a loop structure comprises 13 nucleotides. In some embodiments, the number of nucleotides in the RNA capable of forming a loop is from 4 to 50 nucleotides or any integer therebetween. In some embodiments, from 0-50% of the loop can be complementary to another portion of the loop. As used herein, the term "loop structure" is a sequence that joins two complementary strands of nucleic acid. In some embodiments, 1-3 nucleotides of the loop structure are contiguous to the complementary strands of nucleic acid and may be complementary to 1-3 nucleotides of the distal portion of the loop structure. For example, the three nucleotides at the 5' end of the loop structure may be complementary to the three nucleotides at the 3' end of the loop structure.

In some embodiments, nucleic acid encoding an RNAi of the present disclosure comprises a heterologous miRNA scaffold. In some embodiments, use of a heterologous miRNA scaffold is used to modulate miRNA expression; for example, to increase miRNA expression or to decrease miRNA expression. Any miRNA scaffold known in the art may be used. In some embodiments, the miRNA scaffold is derived from a miR-155 scaffold (see, e.g., Lagos-Quintana, M. et al. (2002) *Curr. Biol.* 12:735-9 and the Invitrogen™ BLOCK-iT™ Pol II miR RNAi expression vector kit from Life Technologies, Thermo Fisher Scientific; Waltham, Mass.).

IV. Huntington's Disease and Experimental Models Thereof

Huntington's disease (HD) is an inherited neurodegenerative disease caused by an expansion of the CAG repeat in exon 1 of the huntingtin gene (HTF). The resulting extension of the polyglutamine tract in the N-terminal region confers a toxic gain-of-function to the mutant huntingtin protein (mHtt), mHtt toxicity may arise from the formation of insoluble mHtt-containing aggregates, transcriptional dysregulation, and perturbations in protein homeostasis, all of which can lead to neuronal death (Saudou et al. (1998) *Cell*, 95:55-66; Zuccato et al. (2003) *Nat. Genet.* 35:76-83; Schaffar et al. (2004) *Mol. Cell.* 15:95-105; Benn et al., (2008) *J. Neurosci.* 28:10720-10733). Pathological findings in patients with HD include cortical thinning and a striking progressive loss of striatal neurons (Rosas et al., (2002) Neurology 58:695-701). Disease onset typically occurs during the third to fourth decade of life; symptoms include choreiform movements, impaired coordination, progressive dementia, and other psychiatric disturbances (Vonsattel et al., (1985) *J. Neuropathol. Exp. Neurol.* 44:559-577). In most cases, symptoms begin to appear between 30 and 40 years of age with subtle disruptions in motor skills, cognition, and personality. Over time, these progress into jerky, uncontrollable movements and loss of muscle control, dementia, and psychiatric illnesses such as depression, aggression, anxiety, and obsessive-compulsive behaviors. Death typically occurs 10-15 years after the onset of symptoms. Less than 10% of HD cases involve a juvenile-onset form of the disease, characterized by a faster disease progression. It is thought that approximately 1 in 10,000 Americans has HD.

Although the genetic basis of HD has been known for almost 20 years, current therapies are largely palliative and do not address the underlying cause of the disease. This is likely due in part to the fact that the etiology of this disease is complex, with detrimental effects observed in a wide variety of cellular processes. Hence, the focus of drug development has been directed at addressing the primary offending trigger, namely, the mutant HTT gene itself.

Most cases of HD are associated with a trinucleotide CAG repeat expansion in the HTT gene. The number of CAG repeats in the HTT gene is strongly correlated with the manifestation of HD. For example, individuals with 35 or fewer repeats typically do not develop HD, but individuals with between 27 and 35 repeats have a greater risk of having offspring with HD. Individuals with between 36 and 40-42 repeats have an incomplete penetrance of HD, whereas individuals with more than 40-42 repeats show complete penetrance. Cases of juvenile-onset HD may be associated with CAG repeat sizes of 60 or more.

The polyQ-expanded Htt protein resulting from this CAG repeat expansion is associated with cellular aggregates or inclusion bodies, perturbations to protein homeostasis, and transcriptional dysregulation. While these toxic phenotypes may be seen throughout the body, they are most typically associated with neuronal cell death in the CNS. HD patients often display cortical thinning and a striking, progressive loss of striatal neurons. The striatum appears to be the most vulnerable region of the brain in HD (particularly the striatal medium spiny neurons), with early effects seen in the putamen and caudate nucleus. Cell death in the striatal spiny neurons, increased numbers of astrocytes, and activation of microglia are observed in the brains of HD patients. HD may also affect certain regions of the hippocampus, cerebral cortex, thalamus, hypothalamus, and cerebellum.

Proposed approaches to blocking Htt expression include the use of antisense oligonucleotides (ASOs) as well as RNA interference (RNAi) that uses either duplex RNAs (dsRNAs) or chemically modified single-stranded RNAs (ssRNAs) (Harper et al., (2005) *Proc. Natl. Acad. Sci. USA* 102:5820-5825; DiFiglia et al., (2007) *Proc. Natl. Acad. Sci. USA* 104:17204-17209; Boudreau et al., (2009b) *Mol. Ther.* 17:1053-1063; Drouet et al., (2009) *Ann. Neurol.* 65:276-285; Sah et al., (2011) *J. Clin. Invest.* 121:500-507; Matsui et al., (2012) *Drug Discov. Today* 17:443-450; Yu et al., (2012) *Cell* 150:895-908). However, hurdles to translating an ASO approach into the clinic may include the need to incorporate a device to facilitate repeated and chronic infusions of ASO into the CNS, and to the need to adequately distribute the drug to target regions in a large brain.

To circumvent these potential issues with ASO, employing AAV-mediated expression of an RNAi (e.g., siRNA), which offers the potential for increased safety, increased efficiency, and longer-lasting efficacy, may be advantageous. As HD patients express both mutant and wild-type Htt alleles, a majority of siRNA targeting sequences will likely degrade both alleles. However, non-allele-specific Htt silencing in HD mice has been shown to be well tolerated and can afford the same benefit as reducing mutant Htt alone (Boudreau et al., (2009b) *Mol. Ther.* 17:1053-1063; Drouet et al., (2009) *Ann. Neurol.* 65:276-285; Kordasiewicz et al., (2012) *Neuron* 74(6):1031-1044). Moreover, the partial and sustained suppression of wild-type Htt in the putamen of non-human primates following AAV-mediated RNAi reportedly did not have any untoward effects, which suggests that the adult brain can tolerate reduced levels of wild-type Htt (McBride et al., (2011) *Mol. Ther.* 19:2152-2162; Grondin et al., (2012) *Brain* 135:1197-1209).

Animal models of HD may be used to test potential therapeutic strategies, such as the compositions and methods of the present disclosure. Mouse models for HD are known in the art. These include mouse models with fragments of mutant HT such as the R6/1 and N171-82Q HD mice (Harper et al., (2005) *Proc. Natl. Acad. Sci. USA* 102:5820-5825, Rodriguez-Lebron et al., (2005) *Mol. Ther.* 12:618-633, Machida et al., (2006) *Biochem. Biophys. Res. Commun.* 343:190-197). Another example of a mouse HD model described herein is the YAC128 mouse model. This model bears a yeast artificial chromosome (YAC) expressing a mutant human H7T gene with 128 CAG repeats, and YAC128 mice exhibit significant and widespread accumulation of Htt aggregates in the striatum by 12 months of age (Slow et al., (2003) *Hum. Mol. Genet.* 12:1555-1567, Pouladi et al., (2012) *Hum. Mol. Genet.* 21:2219-2232).

Other animal models for HD may also be used. For example, transgenic rat (von Horsten, S. et al. (2003) *Hum. Mol. Genet.* 12:617-24) and rhesus monkey (Yang, S. H. et al. (2008) *Nature* 453:921-4) models have been described. Non-genetic models are also known. These most often involve the use of excitotoxic compounds (such as quinolinic acid or kainic acid) or mitochondrial toxins (such as 3-nitropropionic acid and malonic acid) to induce striatal neuron cell death in rodents or non-human primates (for more description and references, see Ramaswamy, S. et al. (2007) *ILAR J.* 48:356-73).

V. Methods to Treat Huntington's Disease

In some aspects, the invention provides methods and compositions for treating Huntington's disease in a mammal comprising administering to the mammal a pharmaceutical composition of the present disclosure (e.g., a pharmaceutical composition comprising a viral particle of the present disclosure). In some aspects, the invention provides methods and compositions for inhibiting the expression of htt in a mammal with Huntington's disease comprising administering to the mammal a pharmaceutical composition of the present disclosure (e.g., a pharmaceutical composition comprising a viral particle of the present disclosure). In some aspects, the invention provides methods and compositions for inhibiting the accumulation of htt in a cell of a mammal with Huntington's disease comprising administering to the mammal a pharmaceutical composition of the present disclosure (e.g., a pharmaceutical composition comprising a viral particle of the present disclosure).

In some aspects, the invention provides methods and compositions for ameliorating a symptom of HD, comprising administration of an effective amount of recombinant viral particles comprising a vector encoding an RNAi of the present disclosure to the brain of a mammal. In some embodiments, the symptoms of HD include, but are not limited to, chorea, rigidity, uncontrollable body movements, loss of muscle control, lack of coordination, restlessness, slowed eye movements, abnormal posturing, instability, ataxic gait, abnormal facial expression, speech problems, difficulties chewing and/or swallowing, disturbance of sleep, seizures, dementia, cognitive deficits (e.g., diminished abilities related to planning, abstract thought, flexibility, rule acquisition, interpersonal sensitivity, self-control, attention, learning, and memory), depression, anxiety, changes in personality, aggression, compulsive behavior, obsessive-compulsive behavior, hypersexuality, psychosis, apathy, irritability, suicidal thoughts, weight loss, muscle atrophy, heart failure, reduced glucose tolerance, testicular atrophy, and osteoporosis.

In some aspects, the invention provides methods to prevent or delay progression of HD. Autosomal dominant HD is a genetic disease that can be genotyped. For example, the number of CAG repeats in HT may be determined by PCR-based repeat sizing. This type of diagnosis may be performed at any stage of life through directly testing juveniles or adults (e.g., along with presentation of clinical symptoms), prenatal screening or prenatal exclusion testing (e.g., by chorionic villus sampling or amniocentesis), or preimplantation screening of embryos. As such, the methods described herein may be used as a prophylactic treatment of HD since diagnosis may occur before symptom onset. For example, HD may be diagnosed by genetic testing (prenatal testing, testing at birth, etc.) and treated prophylactically (e.g., using a rAAV particle described herein) prior to symptom onset (e.g., CNS cell loss) to prevent HD symptom onset and/or progression. HD patients may display shrinkage of the caudate nuclei and/or putamen and/or cortex and/or enlarged ventricles as seen by brain imaging. These symptoms, combined with a family history of HD and/or clinical symptoms, may indicate HD.

Means for determining amelioration of the symptoms of HD are known in the art. For example, the Unified Huntington's Disease Rating Scale (UHDRS) may be used to assess motor function, cognitive function, behavioral abnormalities, and functional capacity (see, e.g., Huntington Study Group (1996) *Movement Disorders* 11:136-42). This rating scale was developed to provide a uniform, comprehensive test for multiple facets of the disease pathology, incorporating elements from tests such as the HD Activities and Daily Living Scale, Marsden and Quinn's chorea severity scale, the Physical Disability and Independence scales, the HD motor rating scale (HDMRS), the HD functional capacity scale (HDFCS), and the quantitated neurological exam (QNE). Other test useful for determining amelioration of HD symptoms may include without limitation the Montreal Cognitive Assessment, brain imaging (e.g., MRI), Category Fluency Test, Trail Making Test, Map Search, Stroop Word Reading Test, Speeded Tapping Task, and the Symbol Digit Modalities Test.

In some aspects of the invention, the methods and compositions are used for the treatment of humans with HD. As described above, HD is inherited in an autosomal dominant manner and caused by CAG repeat expansion in the HTT gene. Juvenile-onset HD is most often inherited from the paternal side. Huntington disease-like phenotypes have also been correlated with other genetic loci, such as HDL1, PRNP, HDL2, HDL3, and HDL4. It is thought that other genetic loci may modify the manifestation of HD symptoms, including mutations in the GRIN2A, GRIN2B, MSX1, GRIK2, and APOE genes.

In some aspects, the invention provides an improved RNAi for targeting htt mRNA in a mammal with Huntington's disease. In some embodiments, the RNAi comprises a first strand comprising a first nucleic acid comprising the sequence 5'-UGGCCGUCCAUCUUGGACCCG-3' (SEQ ID NO:1) and a second strand comprising a second nucleic acid comprising the sequence 5'-CGGGUC-CAAGAUGGACGGCCA-3' (SEQ ID NO:2). An RNAi described herein (e.g., as part of a rAAV vector) may find use, inter alia, in treating Huntington's disease.

In some aspects, the invention provides an improved RNAi for targeting htt mRNA in a mammal with Huntington's disease. In some embodiments, the RNAi comprises a first strand comprising a first nucleic acid comprising the sequence 5'-AGUCGGUGUGGUUGACAAGCA-3' (SEQ ID NO:7) and a second strand comprising a second nucleic acid comprising the sequence 5'-UGCUUGUCAAC-CACACCGACU-3' (SEQ ID NO:8). An RNAi described herein (e.g., as part of a rAAV vector) may find use, inter alia, in treating Huntington's disease.

In some embodiments of the invention, the RNAi is improved to reduce off-target gene silencing. In some embodiments, the RNAi comprises one or more CpG motifs. In some embodiments, the RNAi comprises one or more CpG motifs in a seed region.

In some embodiments, the first strand comprises a nucleic acid sequence having more than about any of 75%, 80%, 85%, 90%, 95%, 96%, 97%, 98% or 99% identity to SEQ ID NO:1 but maintains the CpG motif. In some embodiments, the second strand comprises a nucleic acid sequence having more than about any of 75%, 80%, 85%, 90%, 95%, 96%, 97%, 98% or 99% identity to SEQ ID NO:2 but maintains the CpG motif.

In some embodiments, the first strand comprises a nucleic acid sequence having more than about any of 75%, 80%, 85%, 90%, 95%, 96%, 97%, 98% or 99% identity to SEQ ID NO:7 but maintains the CpG motif. In some embodiments, the second strand comprises a nucleic acid sequence having more than about any of 75%, 80%, 85%, 90%, 95%, 96%, 97%, 98% or 99% identity to SEQ ID NO:8 but maintains the CpG motif.

In some embodiments, the RNAi is a small inhibitory RNA (siRNA), a microRNA (miRNA), or a small hairpin RNA (shRNA). A small inhibitory or interfering RNA (siRNA) is known in the art as a double-stranded RNA molecule of approximately 19-25 (e.g., 19-23) base pairs in length that induces RNAi in a cell. A small hairpin RNA (shRNA) is known in the art as an RNA molecule comprising approximately 19-25 (e.g., 19-23) base pairs of double stranded RNA linked by a short loop (e.g., ~4-11 nucleotides) that induces RNAi in a cell.

In some embodiments, the miRNA comprises a guide sequence that is about 90% identical to SEQ ID NO:1. In some embodiments, the miRNA comprises a guide sequence that is about any of 90% identical, 91% identical, 92% identical, 93% identical, 94% identical, 95% identical, 96% identical, 97% identical, 98% identical, 99% identical, or 100% identical to SEQ ID NO:1.

In some embodiments, the miRNA comprises a non-guide sequence that is about 90% identical to SEQ ID NO:2. In some embodiments, the miRNA comprises a non-guide sequence that is about any of 90% identical, 91% identical, 92% identical, 93% identical, 94% identical, 95% identical, 96% identical, 97% identical, 98% identical, 99% identical, or 100% identical to SEQ ID NO:2.

In some embodiments, the miRNA comprises a guide sequence that is about 90% identical to SEQ ID NO:7. In some embodiments, the miRNA comprises a guide sequence that is about any of 90% identical, 91% identical, 92% identical, 93% identical, 94% identical, 95% identical, 96% identical, 97% identical, 98% identical, 99% identical, or 100% identical to SEQ ID NO:7.

In some embodiments, the miRNA comprises a non-guide sequence that is about 90% identical to SEQ ID NO:8. In some embodiments, the miRNA comprises a non-guide sequence that is about any of 90% identical, 91% identical, 92% identical, 93% identical, 94% identical, 95% identical, 96% identical, 97% identical, 98% identical, 99% identical, or 100% identical to SEQ ID NO:8.

In some embodiments, the first strand and the second strand are linked by means of RNA capable of forming a loop structure. As is commonly known in the art, an RNA loop structure (e.g., a stem-loop or hairpin) is formed when an RNA molecule comprises two sequences of RNA that basepair together separated by a sequence of RNA that does not base pair together. For example, a loop structure may form in the RNA molecule A-B-C if sequences A and C are complementary or partially complementary such that they base pair together, but the bases in sequence B do not base pair together.

In some embodiments, the RNA capable of forming a loop structure comprises from 4 to 50 nucleotides. In certain embodiments, the RNA capable of forming a loop structure comprises 13 nucleotides. In certain embodiments, the RNA capable of forming a loop structure comprises the nucleotide sequence GUUUUGGCCACUGACUGAC (SEQ ID NO: 13). In some embodiments, the vector genome comprises a nucleotide sequence that is at least about any of 80%, 85%, 90%, 91%, 92%, 93%, 94%, 95%, 96%, 97%, 98%, or 99% identical to the sequence of SEQ ID NO:13.

In some aspects, the invention provides methods comprising administering to a mammal (e.g., a mammal with HD) an RNAi comprising a first strand comprising a first nucleic acid comprising the sequence 5'-UGGCCGUC-CAUCUUGGACCCG-3' (SEQ ID NO: 1) and a second strand comprising a second nucleic acid comprising the sequence 5'-CGGGUCCAAGAUGGACGGCCA-3' (SEQ ID NO:2). In some embodiments, a recombinant viral particle comprises the RNAi. In some embodiments, the recombinant viral particle is an AAV particle encapsidating a rAAV vector, an adenovirus particle encapsidating a recombinant adenoviral vector, a lentiviral particle encapsidating a recombinant lentiviral vector or an HSV particle encapsidating a recombinant HSV vector wherein the rAAV vector, the adenoviral vector, the lentiviral vector or the HSV vector encodes the RNAi.

In some aspects, the invention provides methods comprising administering to a mammal (e.g., a mammal with HD) an RNAi comprising a first nucleic acid comprising the sequence 5'-AGUCGGUGUGGUUGACAAGCA-3' (SEQ ID NO:7) and a second strand comprising a second nucleic acid comprising the sequence 5'-UGCUUGUCAAC-CACACCGACU-3' (SEQ ID NO:8). In some embodiments, a recombinant viral particle comprises the RNAi. In some embodiments, the recombinant viral particle is an AAV particle encapsidating a rAAV vector, an adenovirus particle encapsidating a recombinant adenoviral vector, a lentiviral particle encapsidating a recombinant lentiviral vector or an HSV particle encapsidating a recombinant HSV vector wherein the rAAV vector, the adenoviral vector, the lentiviral vector or the HSV vector encodes the RNAi.

In some embodiments, delivery of recombinant viral particles is by injection of viral particles to the brain. In some embodiments, delivery of recombinant viral particles is by injection of viral particles to the striatum. Intrastriatal administration delivers recombinant viral particles to an area of the brain, the striatum (including the putamen and caudate nucleus), that is highly affected by HD. In addition, and without wishing to be bound to theory, it is thought that recombinant viral particles (e.g., rAAV particles) injected into the striatum may be also dispersed (e.g., through retrograde transport) to other areas of the brain, including without limitation projection areas (e.g., the cortex). In some embodiments, the recombinant viral particles are delivered by convection enhanced delivery (e.g., convection enhanced delivery to the striatum).

In some aspects, the invention provides methods for treating Huntington's disease in a mammal comprising administering to the mammal the pharmaceutical composition of the present disclosure. In some aspects, the invention provides methods for inhibiting the accumulation of htt in a cell of a mammal with Huntington's disease comprising administering to the mammal the pharmaceutical composition of the present disclosure. In some aspects, the invention provides methods for inhibiting the expression of htt in a mammal with Huntington's disease comprising administering to the mammal the pharmaceutical composition of the present disclosure. In some embodiments, the htt is a mutant htt (e.g., an htt comprising greater than 35, greater than 36, greater than 37, greater than 38, greater than 39, greater than 40, greater than 41, or greater than 42 CAG repeats). In some embodiments, expression and/or accumulation of a wild-type htt is also inhibited. As described herein, and without wishing to be bound to theory, it is thought that inhibition of expression and/or accumulation of mutant htt in a mammal with HD is highly beneficial, but the inhibition of expression and/or accumulation of wild-type htt in the same mammal as a side effect (e.g., of an RNAi of the present disclosure) may be well tolerated (e.g., produces few or no unintended side effects).

In some embodiments, a cell comprises a vector (e.g., a vector comprising an expression construct encoding an RNAi of the present disclosure). In some embodiments, the vector is a rAAV vector. In some embodiments, the vector is a recombinant adenoviral vector, a recombinant lentiviral vector or a recombinant herpes simplex virus (HSV) vector. In some embodiments, the cell is a central nervous system (CNS) cell.

In some embodiments, the administration of an effective amount of recombinant viral particles comprising a vector encoding an RNAi of the present disclosure transduces neurons (e.g., striatal neurons, such as spiny neurons) at or near the site of administration. In some embodiments, more than about any of 5%, 10%, 15%, 20%, 25%, 30%, 35%, 40%, 45%, 50%, 55%, 60%, 65%, 70%, 75% or 100% of neurons are transduced. In some embodiments, about 5% to about 100%, about 10% to about 50%, about 10% to about 30%, about 25% to about 75%, about 25% to about 50%, or about 30% to about 50% of the neurons are transduced. Methods to identify neurons transduced by recombinant viral particles expressing miRNA are known in the art; for example, immunohistochemistry, RNA detection (e.g., qPCR, Northern blotting, RNA-seq, in situ hybridization, and the like) or the use of a co-expressed marker such as enhanced green fluorescent protein can be used to detect expression.

In some embodiments of the invention, the methods comprise administration to the brain of a mammal an effective amount of recombinant viral particles comprising a vector encoding an RNAi of the present disclosure for treating a mammal, e.g., a human, with HD. In some embodiments, the composition is injected to one or more locations in the brain to allow expression of an RNAi of the present disclosure in at least the neurons. In some embodiments, the composition is injected into any one of one, two, three, four, five, six, seven, eight, nine, ten or more than ten locations in the brain. In some embodiments, the composition is injected into the striatum. In some embodiments, the composition is injected into the dorsal striatum. In some embodiments, the composition is injected into the putamen. In some embodiments, the composition is injected into the caudate nucleus. In some embodiments, the composition is injected into the putamen and into the caudate nucleus.

In some embodiments, the recombinant viral particles are administered to one hemisphere of the brain. In some embodiments, the recombinant viral particles are administered to both hemispheres of the brain.

In some embodiments the recombinant viral particles are administered to more than one location simultaneously or sequentially. In some embodiment, multiple injections of recombinant viral particles are no more than one hour, two hours, three hours, four hours, five hours, six hours, nine hours, twelve hours or 24 hours apart.

In some embodiments, the invention provides a method for treating a human with HD by administering an effective amount of a pharmaceutical composition comprising a recombinant viral vector encoding an RNAi of the present disclosure to suppress the activity of a mutant HTT. In some embodiments, the pharmaceutical composition comprises one or more pharmaceutically acceptable excipients.

In some embodiments, the methods comprise administering an effective amount of a pharmaceutical composition comprising a recombinant viral vector encoding an RNAi of the present disclosure to suppress the activity of a mutant HTT. In some embodiments, the viral titer of the viral particles (e.g., rAAV particles) is at least about any of $5 \times 10^{12}$, $6 \times 10^{12}$, $7 \times 10^{12}$, $8 \times 10^{12}$, $9 \times 10^{12}$, $10 \times 10^{12}$, $11 \times 10^{12}$, $15 \times 10^{12}$, $20 \times 10^{12}$, $25 \times 10^{12}$, $30 \times 10^{12}$, or $50 \times 10^{12}$ genome copies/mL. In some embodiments, the viral titer of the viral particles (e.g., rAAV particles) is about any of $5 \times 10^{12}$ to $6 \times 10^{12}$, $6 \times 10^{12}$ to $7 \times 10^{12}$, $7 \times 10^{12}$ to $8 \times 10^{12}$ $8 \times 10^{12}$ to $9 \times 10^{12}$, $9 \times 10^{12}$ to $10 \times 10^{12}$, $10 \times 10^{12}$ to $11 \times 10^{12}$, $11 \times 10^{12}$ to $15 \times 10^{12}$, $15 \times 10^{12}$ to $20 \times 10^{12}$, $20 \times 10^{12}$ to $25 \times 10^{12}$, $25 \times 10^{12}$ to $30 \times 10^{12}$, $30 \times 10^{12}$ to $50 \times 10^{12}$, or $50 \times 10^{12}$ to $100 \times 10^{12}$ genome copies/mL. In some embodiments, the viral titer of the viral particles (e.g., rAAV particles) is about any of $5 \times 10^{12}$ to $10 \times 10^{12}$, $10 \times 10^{12}$ to $25 \times 10^{12}$, or $25 \times 10^{12}$ to $50 \times 10^{12}$ genome copies/mL. In some embodiments, the viral titer of the viral particles (e.g., rAAV particles) is at least about any of $5 \times 10^9$, $6 \times 10^9$, $7 \times 10^9$, $8 \times 10^9$, $9 \times 10$, $10 \times 10^9$, $11 \times 10^9$, $15 \times 10^9$, $20 \times 10^9$, $25 \times 10^9$, $30 \times 10^9$, or $50 \times 10^9$ transducing units/mL. In some embodiments, the viral titer of the viral particles (e.g., rAAV particles) is about any of $5 \times 10^9$ to $6 \times 10^9$, $6 \times 10^9$ to $7 \times 10^9$, $7 \times 10^9$ to $8 \times 10^9$, $8 \times 10^9$ to $9 \times 10^9$, $9 \times 10^9$ to $10 \times 10^9$, $10 \times 10^9$ to $11 \times 10^9$, $11 \times 10^9$ to $1 \times 10^9$, $15 \times 10^9$ to $20 \times 10^9$, $20 \times 10^9$ to $25 \times 10^9$, $25 \times 10^9$ to $30 \times 10^9$, $30 \times 10^9$ to $50 \times 10^9$ or $50 \times 10^9$ to $100 \times 10^9$ transducing units/mL. In some embodiments, the viral titer of the viral particles (e.g., rAAV particles) is about any of $5 \times 10^9$ to $10 \times 10^9$, $10 \times 10^9$ to $15 \times 10^9$, $15 \times 10^9$ to $25 \times 10^9$, or $25 \times 10^9$ to $50 \times 10^9$ transducing units/mL. In some embodiments, the viral titer of the viral particles (e.g., rAAV particles) is at least any of about $5 \times 10^{10}$, $6 \times 10^{10}$, $7 \times 10^{10}$, $8 \times 10^{10}$, $9 \times 10^{10}$, $10 \times 10^{10}$, $11 \times 10^{10}$, $15 \times 10^{10}$, $20 \times 10^{10}$, $25 \times 10^{10}$, $30 \times 10^{10}$, $40 \times 10^{10}$, or $50 \times 10^{10}$ infectious units/mL. In some embodiments, the viral titer of the viral particles (e.g., rAAV particles) is at least any of about $5 \times 10^{10}$ to $6 \times 10^{10}$, $6 \times 10^{10}$ to $7 \times 10^{10}$, $7 \times 10^{10}$ to $8 \times 10^{10}$, $8 \times 10^{10}$ to $9 \times 10^{10}$, $9 \times 10^{10}$ to $10 \times 10^{10}$, $10 \times 10^{10}$ to $11 \times 10^{10}$, $11 \times 10^{10}$ to $15 \times 10^{10}$, $15 \times 10^{10}$ to $20 \times 10^{10}$, $20 \times 10^{10}$ to $25 \times 10^{10}$, $25 \times 10^{10}$ to $30 \times 10^{10}$, $30 \times 10^{10}$ to $40 \times 10^{10}$, $40 \times 10^{10}$ to $50 \times 10^{10}$, or $50 \times 10^{10}$ to $100 \times 10^{10}$ infectious units/mL. In some embodiments, the viral titer of the viral particles (e.g., rAAV particles) is at least any of about $5 \times 10^{10}$ to $10 \times 10^{10}$, $10 \times 10^{10}$ to $15 \times 10^{10}$, $15 \times 10^{10}$ to $25 \times 10^{10}$, or $25 \times 10^{10}$ to $50 \times 10^{10}$ infectious units/mL.

In some embodiments, the dose of viral particles administered to the individual is at least about any of $1 \times 10^8$ to about $1 \times 10^{13}$ genome copies/kg of body weight. In some embodiments, the dose of viral particles administered to the individual is about any of $1 \times 10^8$ to about $1 \times 10^{13}$ genome copies/kg of body weight.

In some embodiments, the total amount of viral particles administered to the individual is at least about any of $1 \times 10^9$ to about $1 \times 10^{14}$ genome copies. In some embodiments, the total amount of viral particles administered to the individual is about any of $1 \times 10^9$ to about $1 \times 10^{14}$ genome copies.

In some embodiments of the invention, the volume of the composition injected to the striatum is more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, or 1 mL, or any amount therebetween.

In some embodiments, a first volume of the composition is injected into a first region of the brain, and a second volume of the composition is injected into a second region of the brain. For example, in some embodiments, a first volume of the composition is injected into the caudate nucleus, and a second volume of the composition is injected into the putamen. In some embodiments, a 1× volume of the composition is injected into the caudate nucleus, and a 1.5×, 2×, 2.5×, 3×, 3.5×, or 4× volume of the composition is injected into the putamen, where X is a volume that is more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl, or 1 mL, or any amount therebetween.

Compositions of the invention (e.g., recombinant viral particles comprising a vector encoding an RNAi of the present disclosure) can be used either alone or in combination with one or more additional therapeutic agents for treating HD. The interval between sequential administration can be in terms of at least (or, alternatively, less than) minutes, hours, or days.

V. RNAi Expression Constructs and Vectors

The invention provides expression constructs, vectors and viral particles for expression of the RNAi described herein.

In some embodiments, nucleic acid encoding an RNAi of the present disclosure comprises a heterologous miRNA scaffold. In some embodiments, use of a heterologous miRNA scaffold is used to modulate miRNA expression; for example, to increase miRNA expression or to decrease miRNA expression. Any miRNA scaffold known in the art may be used. In some embodiments, the miRNA scaffold is derived from a miR-155 scaffold (see, e.g., Lagos-Quintana, M. et al. (2002) *Curr. Biol.* 12:735-9 and the Invitrogen™ BLOCK-iT™ Pol II miR RNAi expression vector kit from Life Technologies, Thermo Fisher Scientific; Waltham, Mass.). In some embodiments, nucleic acid encoding an RNAi of the present disclosure comprises a miRNA scaffold. In some embodiments, miRNA scaffold is provided by SEQ ID NO: 14.

In some embodiments, the RNAi targets RNA encoding a polypeptide associated with Huntington's disease (e.g., mutant HTT). Without wishing to be bound to theory, it is thought that an RNAi may be used to reduce or eliminate the expression and/or activity of a polypeptide whose gain-of-function has been associated with Huntington's disease (e.g., mutant HT).

In some embodiments, the transgene (e.g., an RNAi of the present disclosure) is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., *Gene*, 1991, 108(2):193-9) and the elongation factor 1-alpha promoter (EF1-alpha) promoter (Kim et al., *Gene*, 1990, 91(2):217-23 and Guo et al., *Gene Ther.*, 1996, 3(9):802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the invention provides a recombinant vector comprising nucleic acid encoding a heterologous transgene of the present disclosure operably linked to a CBA promoter. Exemplary promoters and descriptions may be found, e.g., in U.S. PG Pub. 20140335054. In some embodiments, the promoter is a CBA promoter, a minimum CBA promoter, a CMV promoter or a GUSB promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EFla promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, *Proc. Natl. Acad. Sci. USA*, 93:3346-3351 (1996)), the tetracycline-repressible system (Gossen et al, *Proc. Natl. Acad. Sci. USA*, 89:5547-5551 (1992)), the tetracycline-inducible system (Gossen et al, *Science*, 268:1766-1769 (1995), see also Harvey et al, *Curr. Opin. Chem. Biol.*, 2:512-518 (1998)), the RU486-inducible system (Wang et al, *Nat. Biotech.*, 15:239-243 (1997) and Wang et al. *Gene Ther.*, 4:432-441 (1997)) and the rapamycin-inducible system (Magari et al, *J. Clin. Invest.*, 100:2865-2872 (1997)). Still other types of inducible promoters which may be useful in this context are those which are regulated by a specific physiological state. e.g., temperature, acute phase, a particular differentiation state of the cell, or in replicating cells only.

In another embodiment, the native promoter, or fragment thereof, for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: neuronal such as neuron-specific enolase (NSE) promoter (Andersen et al., *Cell. Mol. Neurobiol.*, 13:503-15 (1993)), neurofilament light-chain gene promoter (Piccioli et al., *Proc. Natl. Acad. Sci. USA*. 88:5611-5 (1991)), and the neuron-specific vgf gene promoter (Piccioli et al., *Neuron*, 15:373-84 (1995)). In some embodiments, the tissue-specific promoter is a promoter of a gene selected from: neuronal nuclei (NeuN), glial fibrillary acidic protein (GFAP), adenomatous polyposis coli (APC), and ionized calcium-binding adapter molecule 1 (Iba-1). Other appropriate tissue specific promoters will be apparent to the skilled artisan. In some embodiments, the promoter is a chicken Beta-actin (CBA) promoter.

In some embodiments, the promoter expresses the heterologous nucleic acid in a cell of the CNS. As such, in some embodiments, a therapeutic polypeptide or a therapeutic nucleic acid of the invention may be used to treat a disorder of the CNS. In some embodiments, the promoter expresses the heterologous nucleic acid in a brain cell. A brain cell may refer to any brain cell known in the art, including without limitation a neuron (such as a sensory neuron, motor neuron, interneuron, dopaminergic neuron, medium spiny neuron, cholinergic neuron, GABAergic neuron, pyramidal neuron, etc.), a glial cell (such as microglia, macroglia, astrocytes, oligodendrocytes, ependymal cells, radial glia, etc.), a brain parenchyma cell, microglial cell, ependemal cell, and/or a Purkinje cell. In some embodiments, the promoter expresses the heterologous nucleic acid in a neuron and/or glial cell. In some embodiments, the neuron is a medium spiny neuron of the caudate nucleus, a medium spiny neuron of the putamen, a neuron of the cortex layer IV and/or a neuron of the cortex layer V.

Various promoters that express transcripts (e.g., a heterologous transgene) in CNS cells, brain cells, neurons, and glial cells are known in the art and described herein. Such promoters can comprise control sequences normally associated with the selected gene or heterologous control sequences. Often, useful heterologous control sequences include those derived from sequences encoding mammalian or viral genes. Examples include, without limitation, the SV40 early promoter, mouse mammary tumor virus LTR promoter, adenovirus major late promoter (Ad MLP), a herpes simplex virus (HSV) promoter, a cytomegalovirus (CMV) promoter such as the CMV immediate early promoter region (CMVIE), a Rous sarcoma virus (RSV) promoter, synthetic promoters, hybrid promoters, and the like. In addition, sequences derived from nonviral genes, such as the murine metallothionein gene, may also be used. Such promoter sequences are commercially available from, e.g., Stratagene (San Diego, Calif.). CNS-specific promoters and inducible promoters may be used. Examples of CNS-specific promoters include without limitation those isolated from CNS-specific genes such as myelin basic protein (MBP), glial fibrillary acid protein (GFAP), and neuron specific enolase (NSE). Examples of inducible promoters include DNA responsive elements for ecdysone, tetracycline, metallothionein, and hypoxia, inter alia.

The present invention contemplates the use of a recombinant viral genome for introduction of one or more nucleic acid sequences encoding for a RNAi as described herein or packaging into an AAV viral particle. The recombinant viral genome may include any element to establish the expression of a RNAi, for example, all or a functional portion of a promoter, an intron (e.g., a chimeric intron)), a heterologous nucleic acid, an ITR, a ribosome binding element, terminator, enhancer, selection marker, intron, polyA signal, and/or origin of replication. In some embodiments, the rAAV vector comprises one or more of an enhancer, an intron (e.g., a splice donor/splice acceptor pair), a matrix attachment site, or a polyadenylation signal. A variety of introns for use in the invention are known to those of skill in the art, and include the MVM intron, the F IX truncated intron 1, the β-globin SD/immunoglobulin heavy chain SA, the adenovirus SD/immunoglobin SA, the SV40 late SD/SA (19S/16S), and the hybrid adenovirus SD/IgG SA. (Wu et al. 2008, Kurachi et al., 1995, Choi et al. 2014), Wong et al. 1985, Yew et al. 1997, Huang and Gorman (1990).

In some embodiments, the administration of an effective amount of rAAV particles comprising a vector encoding a RNAi transduces cells (e.g., CNS cells, brain cells, neurons, and/or glial cells) at or near the site of administration (e.g., the striatum and/or cortex) or more distal to the site of administration. In some embodiments, more than about any of 5%, 10%, 15%, 20%, 25%, 30%, 35%, 40%, 45%, 50%, 55%, 60%, 65%, 70%, 75% or 100% of neurons are transduced. In some embodiments, about 5% to about 100%, about 10% to about 50%, about 10% to about 30%, about 25% to about 75%, about 25% to about 50%, or about 30% to about 50% of the neurons are transduced. Methods to identify neurons transduced by recombinant viral particles expressing miRNA are known in the art; for example, immunohistochemistry, RNA detection (e.g., qPCR, Northern blotting, RNA-seq, in situ hybridization, and the like) or the use of a co-expressed marker such as enhanced green fluorescent protein can be used to detect expression.

In some aspects, the invention provides viral particles comprising a recombinant self-complementing genome (e.g., a self-complementary rAAV vector). AAV viral particles with self-complementing vector genomes and methods of use of self-complementing AAV genomes are described in U.S. Pat. Nos. 6,596,535; 7,125,717; 7,465,583; 7,785,888; 7,790,154; 7,846,729; 8,093,054; and 8,361,457; and Wang Z., et al., (2003) Gene Ther 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a heterologous nucleic acid). In some embodiments, the vector comprises first nucleic acid sequence encoding the heterologous nucleic acid and a second nucleic acid sequence encoding a complement of the nucleic acid, where the first nucleic acid sequence can form intrastrand base pairs with the second nucleic acid sequence along most or all of its length.

In some embodiments, the first heterologous nucleic acid sequence encoding a RNAi and a second heterologous nucleic acid sequence encoding the complement of the RNAi are linked by a mutated ITR (e.g., the right ITR). In some embodiments, the ITR comprises the polynucleotide sequence 5'-CCACTCCCTCTCTGCGCGCTCGCTCGCT-CACTGAGGCCGGGCGACCAAAGGTCGC CCGACGCCCGGGCTTTGCCCGGGCGGCCTCAGT-GAGCGAGCGAGCGCGCAGAGA GGGA-3 (SEQ ID NO:15). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR.

VI. Viral Particles and Methods of Producing Viral Particles

The invention provides, inter alia, recombinant viral particles comprising a nucleic acid encoding an RNAi of the present disclosure, as well as methods of use thereof to treat a disease or disorder in a mammal; e.g., Huntington's disease.

Viral Particles

The invention provides viral particles comprising the RNAi as disclosed herein. In some embodiments, the invention provides viral particles for delivering the RNAi of the invention as disclosed herein. For example, the invention provides methods of using recombinant viral particles to deliver RNAi to treat a disease or disorder in a mammal; e.g., rAAV particles comprising RNAi to treat HD. In some embodiments, the recombinant viral particle is a recombinant AAV particle. In some embodiments, the viral particle is a recombinant AAV particle comprising a nucleic acid comprising a sequence an RNAi of the present disclosure flanked by one or two ITRs. The nucleic acid is encapsidated in the AAV particle. The AAV particle also comprises capsid proteins. In some embodiments, the nucleic acid comprises the coding sequence(s) of interest (e.g., nucleic acid an RNAi of the present disclosure) operatively linked components in the direction of transcription, control sequences including transcription initiation and termination sequences, thereby forming an expression cassette. The expression cassette is flanked on the 5' and 3' end by at least one functional AAV ITR sequences. By "functional AAV ITR sequences" it is meant that the ITR sequences function as intended for the rescue, replication and packaging of the AAV virion. See Davidson et al., PNAS, 2000, 97(7)3428-32; Passini et al., J. Virol., 2003, 77(12):7034-40; and Pechan et al., Gene Ther., 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.*, 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10): 6081-6; and Bossis et al., *J. Virol.*, 2003, 77(12):6799-810. Use of any AAV serotype is considered within the scope of the present invention. In some embodiments, a rAAV vector is a vector derived from an AAV serotype, including without limitation, AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs or the like. In some embodiments, the nucleic acid in the AAV comprises an ITR of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs or the like. In some embodiments, the nucleic acid in the AAV further encodes an RNAi as described herein. For example, the nucleic acid in the AAV can comprise at least one ITR of any AAV serotype contemplated herein and can further encode an RNAi comprising one strand that comprises a guide region and another strand that comprises a non-guide region. In one embodiment, the nucleic acid in the AAV can comprise at least one ITR of any AAV serotype and can further encode an RNAi comprising a first strand comprising a first nucleic acid comprising the sequence 5'-UGGCCGUCCAUCUUGGACCCG-3' (SEQ ID NO: 1) and a second strand comprising a second nucleic acid comprising the sequence 5'-CGGGUC-CAAGAUGGACGGCCA-3' (SEQ ID NO:2). In some embodiments, the nucleic acid in the AAV comprises 5' to 3' nucleic acid encoding the following: an ITR (e.g., an AAV2 ITR), a promoter, a nucleic acid encoding an RNAi as disclosed herein, a polyadenylation signal, and an AAV ITR (e.g., an AAV2 ITR). In some embodiments, the nucleic acid in the AAV comprises 5' to 3' nucleic acid encoding the following: an ITR (e.g., an AAV2 ITR), a promoter, a nucleic acid encoding an RNAi comprising a first strand comprising a first nucleic acid comprising the sequence 5'-UGGCCGUCCAUCUUGGACCCG-3' (SEQ ID NO:1) and a second strand comprising a second nucleic acid comprising the sequence 5'-CGGGUC-CAAGAUGGACGGCCA-3' (SEQ ID NO:2), a polyadenylation signal, and an AAV ITR (e.g., an AAV2 ITR). In some embodiments, the nucleic acid in the AAV comprises 5' to 3' nucleic acid encoding the following: an ITR (e.g., an AAV2 ITR), a CBA promoter, a nucleic acid encoding an RNAi as disclosed herein, a polyadenylation signal (e.g., a bovine growth hormone polyA), and an AAV ITR (e.g., an AAV2 ITR). In some embodiments, the nucleic acid in the AAV comprises 5' to 3' nucleic acid encoding the following: all or a functional portion of an ITR (e.g., an AAV2 ITR), a CBA promoter, an intron (e.g., a chimeric intron), a nucleic acid encoding an RNAi comprising a first strand comprising a first nucleic acid comprising the sequence 5'-UGGCCGU-CCAUCUUGGACCCG-3' (SEQ ID NO: 1), and a second strand comprising a second nucleic acid comprising the sequence 5'-CGGGUCCAAGAUGGACGGCCA-3' (SEQ ID NO:2), a polyadenylation signal (e.g., a bovine growth hormone polyA), and an AAV ITR (e.g., an AAV2 ITR). In some embodiments, the first strand and second strand form a duplex. In some embodiments, the first strand is linked to the second strand by a linker. In some embodiments, the linker comprises the nucleic acid sequence of SEQ ID NO:13.

In some embodiments, the nucleic acid in the AAV comprises 5' to 3' nucleic acid encoding the following: an ITR (e.g., an AAV2 ITR), a CBA promoter, a nucleic acid encoding an RNAi comprising a first strand comprising a first nucleic acid comprising the sequence 5'-CGGGUC-CAAGAUGGACGGCCA-3' (SEQ ID NO:2), and a second strand comprising a second nucleic acid comprising the sequence 5'-UGGCCGUCCAUCUUGGACCCG-3' (SEQ ID NO:1), a polyadenylation signal (e.g., a bovine growth hormone polyA), and an AAV ITR (e.g., an AAV2 ITR). In some embodiments, the first strand and second strand form a duplex. In some embodiments, the first strand is linked to the second strand by a linker. In some embodiments, the linker comprises the nucleic acid sequence of SEQ ID NO: 13.

In another embodiment, the nucleic acid in the AAV can comprise at least one ITR of any AAV serotype contemplated herein and can further encode an RNAi comprising a first strand comprising a first nucleic acid comprising the sequence 5'-AGUCGGUGUGGUUGACAAGCA-3' (SEQ ID NO:7) and a second strand comprising a second nucleic acid comprising the sequence 5'-UGCUUGUCAAC-CACACCGACU-3' (SEQ ID NO:8). In some embodiments, the nucleic acid in the AAV comprises 5' to 3' nucleic acid encoding the following: an ITR (e.g., an AAV2 ITR), a promoter, a nucleic acid encoding an RNAi as disclosed herein, a polyadenylation signal, and an AAV ITR (e.g., an AAV2 ITR). In some embodiments, the nucleic acid in the AAV comprises 5' to 3' nucleic acid encoding the following: an ITR (e.g., an AAV2 ITR), a promoter, a nucleic acid encoding an RNAi comprising a first strand comprising a first nucleic acid comprising the sequence 5'-AGUCGGU-GUGGUUGACAAGCA-3' (SEQ ID NO:7) and a second strand comprising a second nucleic acid comprising the sequence 5'-UGCUUGUCAACCACACCGACU-3' (SEQ ID NO:8), a polyadenylation signal, and an AAV ITR (e.g., an AAV2 ITR). In some embodiments, the nucleic acid in the AAV comprises 5' to 3' nucleic acid encoding the following: an ITR (e.g., an AAV2 ITR), a CBA promoter, a chimeric intron, a nucleic acid encoding an RNAi as disclosed herein, a polyadenylation signal (e.g., a bovine growth hormone polyA), and an AAV ITR (e.g., an AAV2 ITR). In some embodiments, the nucleic acid in the AAV comprises 5' to 3' nucleic acid encoding the following: an ITR (e.g., an AAV2 ITR), a CBA promoter, a chimeric intron, a nucleic acid encoding an RNAi comprising a first strand comprising a first nucleic acid comprising the sequence 5'-AGUCGGU-GUGGUUGACAAGCA-3' (SEQ ID NO:7), and a second strand comprising a second nucleic acid comprising the sequence 5'-UGCUUGUCAACCACACCGACU-3' (SEQ ID NO:8), a polyadenylation signal (e.g., a bovine growth hormone polyA), and an AAV ITR (e.g., an AAV2 ITR). In some embodiments, the first strand and second strand form a duplex. In some embodiments, the first strand is linked to the second strand by a linker. In some embodiments, the linker comprises the nucleic acid sequence of SEQ ID NO: 13.

In another embodiment, the nucleic acid in the AAV can comprise at least one ITR of any AAV serotype contemplated herein and can further encode an RNAi comprising a first strand comprising a first nucleic acid comprising the sequence 5'-UGCUUGUCAACCACACCGACU-3' (SEQ ID NO:8) and a second strand comprising a second nucleic acid comprising the sequence AGUCGGUGUGUGGUUGACAAGCA-3' (SEQ ID NO:7). In some embodiments, the nucleic acid in the AAV comprises 5' to 3' nucleic acid encoding the following: an ITR (e.g., an AAV2 ITR), a promoter, a nucleic acid encoding an RNAi as disclosed herein, a polyadenylation signal, and an AAV ITR (e.g., an AAV2 ITR). In some embodiments, the nucleic acid in the AAV comprises 5' to 3' nucleic acid encoding the following: an ITR (e.g., an AAV2 ITR), a promoter, an intron, a nucleic acid encoding an RNAi comprising a first strand comprising a first nucleic acid comprising the sequence 5'-UGCUUGUCAACCACACCGACU-3' (SEQ ID NO:8) and a second strand comprising a second nucleic acid comprising the sequence 5'-AGUCGGUGUGGUUGACAAGCA-3' (SEQ ID NO:7), a polyadenylation signal, and an AAV ITR (e.g., an AAV2 ITR). In some embodiments, the nucleic acid in the AAV comprises 5' to 3' nucleic acid encoding the following: an ITR (e.g., an AAV2 ITR), a CBA promoter, a nucleic acid encoding an RNAi as disclosed herein, a polyadenylation signal (e.g., a bovine growth hormone polyA), and an AAV ITR (e.g., an AAV2 ITR). In some embodiments, the nucleic acid in the AAV comprises 5' to 3' nucleic acid encoding the following: an ITR (e.g., an AAV2 ITR), a CBA promoter, an intron, a nucleic acid encoding an RNAi comprising a first strand comprising a first nucleic acid comprising the sequence 5'-UGCUUGUCAACCACACCGACU-3', and a second strand comprising a second nucleic acid comprising the sequence 5'-AGUCGGUGUGGUUGACAAGCA-3' (SEQ ID NO:7), a polyadenylation signal (e.g., a bovine growth hormone polyA), and an AAV ITR (e.g., an AAV2 ITR). In some embodiments, the first strand and second strand form a duplex. In some embodiments, the first strand is linked to the second strand by a linker. In some embodiments, the linker comprises the nucleic acid sequence of SEQ ID NO: 13.

In some embodiments, a vector may include a (one or more) stuffer nucleic acid. In some embodiments, the stuffer nucleic acid may comprise a sequence that encodes a reporter polypeptide. As will be appreciated by those of skill in the art, the stuffer nucleic acid may be located in a variety of regions within the vector, and may be comprised of a continuous sequence (e.g., a single stuffer nucleic acid in a single location) or multiple sequences (e.g., more than one stuffer nucleic acid in more than one location (e.g., 2 locations, 3 locations, etc.) within the vector. In some embodiments, the stuffer nucleic acid may be located downstream of the RNAi sequence. In embodiments, the stuffer nucleic acid may be located upstream of the RNAi sequence (e.g., between the promoter and the nucleic acid encoding the RNAi). As will also be appreciated by those of skill in the art a variety of nucleic acids may be used as a stuffer nucleic acid. In some embodiments, the stuffer nucleic acid comprises all or a portion of a human alpha-1-antitrypsin (AAT) stuffer sequence or a C16 P1 chromosome 16 P1 clone (human C16) stuffer sequence. In some embodiments, the stuffer sequence comprises all or a portion of a gene. For example, the stuffer sequence comprises a portion of the human AAT sequence. One skilled in the art would recognize that different portions of a gene (e.g., the human AAT sequence) can be used as a stuffer fragment. For example, the stuffer fragment may be from the 5' end of the gene, the 3' end of the gene, the middle of a gene, a non-coding portion of the gene (e.g., an intron), a coding region of the gene (e.g. an exon), or a mixture of non-coding and coding portions of a gene. One skilled in the art would also recognize that all or a portion of stuffer sequence may be used as a stuffer sequence. In some embodiments, the stuffer sequence comprises the nucleotide sequence of SEQ ID NO: 18.

In further embodiments, the rAAV particle comprises capsid proteins of AAV1, AAV2, AAV3, AAV4, AAV5, AA6, AAV7, AAV8, AAV9, AAVrh.8, AAVrh8R, AAVrh.10, AAV11, AAV12, or mutants of these capsid proteins. In some embodiments, a mutant capsid protein maintains the ability to form an AAV capsid. In some embodiments, the rAAV particle comprises AAV5 tyrosine mutant capsid (Zhong L. et al., (2008) *Proc Natl Acad Sci USA* 105(22): 7827-7832. In further embodiments, the rAAV particle comprises capsid proteins of an AAV serotype from Clades A-F (Gao, et al., *J. Virol.* 2004, 78(12):6381).

Different AAV serotypes are used to optimize transduction of particular target cells or to target specific cell types within a particular target tissue (e.g., a diseased tissue). A rAAV particle can comprise viral proteins and viral nucleic acids of the same serotype or a mixed serotype. For example, in some embodiments a rAAV particle can comprise AAV1 capsid proteins and at least one AAV2 ITR or it can comprise AAV2 capsid proteins and at least one AAV1 ITR. Any combination of AAV serotypes for production of a rAAV particle is provided herein as if each combination had been expressly stated herein. In some embodiments, the invention provides rAAV particles comprising an AAV1 capsid and a rAAV vector of the present disclosure (e.g., an expression cassette comprising nucleic acid encoding an RNAi of the present disclosure), flanked by at least one AAV2 ITR. In some embodiments, the invention provides rAAV particles comprising an AAV2 capsid.

In some aspects, the invention provides viral particles comprising a recombinant self-complementing genome. AAV viral particles with self-complementing genomes and methods of use of self-complementing AAV genomes are described in U.S. Pat. Nos. 6,596,535; 7,125,717; 7,465,583; 7,785,888; 7,790,154; 7,846,729; 8,093,054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the invention provides an AAV viral particle comprising an AAV genome, wherein the rAAV genome comprises a first heterologous polynucleotide sequence (e.g., an RNAi of the present disclosure) and a second heterologous polynucleotide sequence (e.g., antisense strand of an RNAi of the present disclosure) wherein the first heterologous polynucleotide sequence can form intrastrand base pairs with the second polynucleotide sequence along most or all of its length. In some embodiments, the first heterologous polynucleotide sequence and a second heterologous polynucleotide sequence are linked by a sequence that facilitates intrastrand basepairing; e.g., a hairpin DNA structure. Hairpin structures are known in the art, for example in miRNA or siRNA molecules. In some embodiments, the first heterologous polynucleotide sequence and a second heterologous polynucleotide sequence are linked by a mutated ITR (e.g., the right ITR). In some embodiments, the ITR comprises the polynucleotide sequence 5'-CCACTCCCTCTCTGCGCGCTCGCTCGCTCACT-GAGGCCGGGCGACCAAAGGTC GCCCGACGCCCGGGCTTTGCCCGGGCGGCCTCAGT-GAGCGAGCGAGCGCGCAGA GAGGGA-3 (SEQ ID NO: 15). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR. In some embodiments, the invention provides AAV viral particles comprising a recombinant viral genome comprising a functional AAV2 ITR, a first polynucleotide sequence encoding an RNAi of the present disclosure, a mutated AAV2 ITR comprising a deletion of the D region and lacking a functional terminal resolution sequence, a second polynucleotide sequence comprising the complementary sequence to the sequence encoding an RNAi of the present disclosure, of the first polynucleotide sequence and a functional AAV2 ITR.

In some embodiments, the viral particle is an adenoviral particle. In some embodiments, the adenoviral particle is a recombinant adenoviral particle. e.g., a polynucleotide vector comprising an RNAi of the present disclosure between two ITRs. In some embodiments, the adenoviral particle lacks or contains a defective copy of one or more E1 genes, which renders the adenovirus replication-defective. Adenoviruses include a linear, double-stranded DNA genome within a large (~950 Å), non-enveloped icosahedral capsid. Adenoviruses have a large genome that can incorporate more than 30 kb of heterologous sequence (e.g., in place of the E1 and/or E3 region), making them uniquely suited for use with larger heterologous genes. They are also known to infect dividing and non-dividing cells and do not naturally integrate into the host genome (although hybrid variants may possess this ability). In some embodiments, the adenoviral vector may be a first generation adenoviral vector with a heterologous sequence in place of E1. In some embodiments, the adenoviral vector may be a second generation adenoviral vector with additional mutations or deletions in E2A, E2B, and/or E4. In some embodiments, the adenoviral vector may be a third generation or gutted adenoviral vector that lacks all viral coding genes, retaining only the ITRs and packaging signal and requiring a helper adenovirus in trans for replication, and packaging. Adenoviral particles have been investigated for use as vectors for transient transfection of mammalian cells as well as gene therapy vectors. For further description, see, e.g., Danthinne, X. and Imperiale, M. J. (2000) *Gene Ther.* 7:1707-14 and Tatsis, N. and Ertl, H. C. (2004) *Mol. Ther.* 10:616-29.

In some embodiments, the viral particle is a recombinant adenoviral particle comprising a nucleic acid encoding an RNAi of the present disclosure. Use of any adenovirus serotype is considered within the scope of the present invention. In some embodiments, the recombinant adenoviral vector is a vector derived from an adenovirus serotype, including without limitation, AdHu2, AdHu 3, AdHu4, AdHu5, AdHu7, AdHu11, AdHu24, AdHu26, AdHu34, AdHu35, AdHu36, AdHu37, AdHu41, AdHu48, AdHu49, AdHu50, AdC6, AdC7, AdC69, bovine Ad type 3, canine Ad type 2, ovine Ad. and porcine Ad type 3. The adenoviral particle also comprises capsid proteins. In some embodiments, the recombinant viral particles comprise an adenoviral particle in combination with one or more foreign viral capsid proteins. Such combinations may be referred to as pseudotyped recombinant adenoviral particles. In some embodiments, foreign viral capsid proteins used in pseudotyped recombinant adenoviral particles are derived from a foreign virus or from another adenovirus serotype. In some embodiments, the foreign viral capsid proteins are derived from, including without limitation, reovirus type 3. Examples of vector and capsid protein combinations used in pseudotyped adenovirus particles can be found in the following references (Tatsis, N. et al. (2004) *Mol. Ther.* 10(4): 616-629 and Ahi, Y. et al. (2011) *Curr. Gene Ther.* 11(4): 307-320). Different adenovirus serotypes can be used to optimize transduction of particular target cells or to target specific cell types within a particular target tissue (e.g., a diseased tissue). Tissues or cells targeted by specific adenovirus serotypes, include without limitation, lung (e.g. HuAd3), spleen and liver (e.g. HuAd37), smooth muscle, synoviocytes, dendritic cells, cardiovascular cells, tumor cell lines (e.g. HuAd11), and dendritic cells (e.g. HuAd5 pseudotyped with reovirus type 3, HuAd30, or HuAd35). For further description, see Ahi, Y. et al. (2011) *Curr. Gene Ther.* 11(4):307-320, Kay, M. et al. (2001) *Nat. Med* 7(1): 33-40, and Tatsis, N. et al. (2004) *Mol. Ther.* 10(4):616-629. Adenoviral vectors have been administered by intrastriatal administration (see, e.g., Mittoux, V. et al. (2002) *J. Neurosci.* 22:4478-86).

In some embodiments, the viral particle is a lentiviral particle. In some embodiments, the lentiviral particle is a recombinant lentiviral particle, e.g., a polynucleotide vector encoding an RNAi of the present disclosure between two LTRs. Lentiviruses are positive-sense, ssRNA retroviruses with a genome of approximately 10 kb. Lentiviruses are known to integrate into the genome of dividing and non-dividing cells. Lentiviral particles may be produced, for example, by transfecting multiple plasmids (typically the lentiviral genome and the genes required for replication and/or packaging are separated to prevent viral replication) into a packaging cell line, which packages the modified lentiviral genome into lentiviral particles. In some embodiments, a lentiviral particle may refer to a first generation vector that lacks the envelope protein. In some embodiments, a lentiviral particle may refer to a second generation vector that lacks all genes except the gag/pol and tat/rev regions. In some embodiments, a lentiviral particle may refer to a third generation vector that only contains the endogenous rev, gag, and pol genes and has a chimeric LTR for transduction without the tat gene (see Dull, T. et al. (1998) *J. Virol.* 72:8463-71). For further description, see Durand, S. and Cimarelli, A. (2011) *Viruses* 3:132-59.

In some embodiments, the viral particle is a recombinant lentiviral particle comprising a nucleic acid encoding an RNAi of the present disclosure. Use of any lentiviral vector is considered within the scope of the present invention. In some embodiments, the lentiviral vector is derived from a lentivirus including, without limitation, human immunodeficiency virus-1 (HIV-1), human immunodeficiency virus-2 (HIV-2), simian immunodeficiency virus (SIV), feline immunodeficiency virus (FIV), equine infectious anemia virus (EIAV), bovine immunodeficiency virus (BIV), Jembrana disease virus (JDV), visna virus (VV), and caprine arthritis encephalitis virus (CAEV). The lentiviral particle also comprises capsid proteins. In some embodiments, the recombinant viral particles comprise a lentivirus vector in combination with one or more foreign viral capsid proteins. Such combinations may be referred to as pseudotyped recombinant lentiviral particles. In some embodiments, foreign viral capsid proteins used in pseudotyped recombinant lentiviral particles are derived from a foreign virus. In some embodiments, the foreign viral capsid protein used in pseudotyped recombinant lentiviral particles is Vesicular stomatitis virus glycoprotein (VSV-GP). VSV-GP interacts with a ubiquitous cell receptor, providing broad tissue tropism to pseudotyped recombinant lentiviral particles. In addition, VSV-GP is thought to provide higher stability to pseudotyped recombinant lentiviral particles. In other embodiments, the foreign viral capsid proteins are derived from, including without limitation, Chandipura virus, Rabies virus, Mokola virus, Lymphocytic choriomeningitis virus (LCMV), Ross River virus (RRV), Sindbis virus, Semliki Forest virus (SFV), Venezuelan equine encephalitis virus, Ebola virus Reston, Ebola virus Zaire, Marburg virus, Lassa virus, Avian leukosis virus (ALV), Jaagsiekte sheep retrovirus (JSRV), Moloney Murine leukemia virus (MLV), Gibbon ape leukemia virus (GALV), Feline endogenous retrovirus (RD114), Human T-lymphotrophic virus 1 (HTLV-1), Human foamy virus, Maedi-visna virus (MVV), SARS-CoV, Sendai virus, Respiratory syncytia virus (RSV), Human parainfluenza virus type 3, Hepatitis C virus (HCV), Influenza virus, Fowl plague virus (FPV), or *Autographa californica* multiple nucleopolyhedro virus (AcMNPV). Examples of vector and capsid protein combinations used in pseudotyped Lentivirus particles can be found, for example, in Cronin, J. et al. (2005). *Curr. Gene Ther.* 5(4):387-398. Different pseudotyped recombinant lentiviral particles can be used to optimize transduction of particular target cells or to target specific cell types within a particular target tissue (e.g., a diseased tissue). For example, tissues targeted by specific pseudotyped recombinant lentiviral particles, include without limitation, liver (e.g. pseudotyped with a VSV-G, LCMV, RRV, or SeV F protein), lung (e.g. pseudotyped with an Ebola, Marburg, SeV F and HN, or JSRV protein), pancreatic islet cells (e.g. pseudotyped with an LCMV protein), central nervous system (e.g. pseudotyped with a VSV-G, LCMV, Rabies, or Mokola protein), retina (e.g. pseudotyped with a VSV-G or Mokola protein), monocytes or muscle (e.g. pseudotyped with a Mokola or Ebola protein), hematopoietic system (e.g. pseudotyped with an RD114 or GALV protein), or cancer cells (e.g. pseudotyped with a GALV or LCMV protein). For further description, see Cronin, J. et al. (2005). *Curr. Gene Ther.* 5(4):387-398 and Kay, M. et al. (2001) *Nat. Med.* 7(1):33-40.

In some embodiments, the viral particle is a herpes simplex virus (HSV) particle. In some embodiments, the HSV particle is a rHSV particle, e.g., a polynucleotide vector encoding an RNAi of the present disclosure between two TRs. HSV is an enveloped, double-stranded DNA virus with a genome of approximately 152 kb. Advantageously, approximately half of its genes are nonessential and may be deleted to accommodate heterologous sequence. HSV particles infect non-dividing cells. In addition, they naturally establish latency in neurons, travel by retrograde transport, and can be transferred across synapses, making them advantageous for transfection of neurons and/or gene therapy approaches involving the nervous system. In some embodiments, the HSV particle may be replication-defective or replication-competent (e.g., competent for a single replication cycle through inactivation of one or more late genes). For further description, see Manservigi, R. et al. (2010) Open *Virol. J.* 4:123-56.

In some embodiments, the viral particle is a rHSV particle comprising a nucleic acid encoding an RNAi of the present disclosure. Use of any HSV vector is considered within the scope of the present invention. In some embodiments, the HSV vector is derived from a HSV serotype, including without limitation, HSV-1 and HSV-2. The HSV particle also comprises capsid proteins. In some embodiments, the recombinant viral particles comprise a HSV vector in combination with one or more foreign viral capsid proteins. Such combinations may be referred to as pseudotyped rHSV particles. In some embodiments, foreign viral capsid proteins used in pseudotyped rHSV particles are derived from a foreign virus or from another HSV serotype. In some embodiments, the foreign viral capsid protein used in a pseudotyped rHSV particle is a Vesicular stomatitis virus glycoprotein (VSV-GP). VSV-GP interacts with a ubiquitous cell receptor, providing broad tissue tropism to pseudotyped rHSV particles. In addition, VSV-GP is thought to provide higher stability to pseudotyped rHSV particles. In other embodiments, the foreign viral capsid protein may be from a different HSV serotype. For example, an HSV-1 vector may contain one or more HSV-2 capsid proteins. Different HSV serotypes can be used to optimize transduction of particular target cells or to target specific cell types within a particular target tissue (e.g., a diseased tissue). Tissues or cells targeted by specific adenovirus serotypes include without limitation, central nervous system and neurons (e.g. HSV-1). For further description, see Manservigi, R. et al. (2010) *Open Virol J* 4:123-156, Kay, M. et al. (2001) *Nat. Med.* 7(1):33-40, and Meignier, B. et al. (1987) *J. Infect. Dis.* 155(5):921-930.

Production of Viral Particles rAAV particles can be produced using methods known in the art. See, e.g., U.S. Pat. Nos. 6,566,118; 6,989,264; and 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

Methods known in the art for production of rAAV vectors include but are not limited to transfection, stable cell line production, and infectious hybrid virus production systems which include adenovirus-AAV hybrids, herpesvirus-AAV hybrids (Conway, J E et al., (1997) *J. Virology* 71(11):8780-8789) and baculovirus-AAV hybrids. rAAV production cultures for the production of rAAV virus particles all require; 1) suitable host cells, including, for example, human-derived cell lines such as HeLa, A549, or 293 cells, or insect-derived cell lines such as SF-9, in the case of baculovirus production systems; 2) suitable helper virus function, provided by wild-type or mutant adenovirus (such as temperature sensitive adenovirus), herpes virus, baculovirus, or a plasmid construct providing helper functions; 3) AAV rep and cap genes and gene products; 4) a nucleic acid (such as a therapeutic nucleic acid) flanked by at least one AAV ITR sequences: and 5) suitable media and media components to support rAAV production. In some embodiments, the AAV rep and cap gene products may be from any AAV serotype. In general, but not obligatory, the AAV rep gene product is of the same serotype as the ITRs of the rAAV vector genome as long as the rep gene products may function to replicated and package the rAAV genome. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV vectors. In some embodiments, the AAV helper functions are provided by adenovirus or HSV. In some embodiments, the AAV helper functions are provided by baculovirus and the host cell is an insect cell (e.g., *Spodoptera frugiperda* (Sf9) cells).

In some embodiments, rAAV particles may be produced by a triple transfection method, such as the exemplary triple transfection method provided infra. Briefly, a plasmid containing a rep gene and a capsid gene, along with a helper adenoviral plasmid, may be transfected (e.g., using the calcium phosphate method) into a cell line (e.g., HEK-293 cells), and virus may be collected and optionally purified. As such, in some embodiments, the rAAV particle was produced by triple transfection of a nucleic acid encoding the rAAV vector, a nucleic acid encoding AAV rep and cap, and a nucleic acid encoding AAV helper virus functions into a host cell, wherein the transfection of the nucleic acids to the host cells generates a host cell capable of producing rAAV particles.

In some embodiments, rAAV particles may be produced by a producer cell line method, such as the exemplary producer cell line method provided infra (see also (referenced in Martin et al., (2013) *Human Gene Therapy Methods* 24:253-269). Briefly, a cell line (e.g., a HeLa cell line) may be stably transfected with a plasmid containing a rep gene, a capsid gene, and a promoter-heterologous nucleic acid sequence. Cell lines may be screened to select a lead clone for rAAV production, which may then be expanded to a production bioreactor and infected with an adenovirus (e.g., a wild-type adenovirus) as helper to initiate rAAV production. Virus may subsequently be harvested, adenovirus may be inactivated (e.g., by heat) and/or removed, and the rAAV particles may be purified. As such, in some embodiments, the rAAV particle was produced by a producer cell line comprising one or more of nucleic acid encoding the rAAV vector, a nucleic acid encoding AAV rep and cap, and a nucleic acid encoding AAV helper virus functions.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication and/or encapsidation protein; (ii) an rAAV pro-vector comprising a nucleic acid encoding an RNAi of the present disclosure as described herein flanked by at least one AAV ITR, and (iii) an AAV helper function; and (b) recovering the rAAV particles produced by the host cell. In some embodiments, the RNAi comprises the nucleotide sequence of SEQ ID NO:7. In some embodiments, said at least one AAV ITR is selected from the group consisting of AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs or the like. In some embodiments, said encapsidation protein is selected from the group consisting of AAV1, AAV2, AAV3, AAV4, AAV5, AAV6 (e.g., a wild-type AAV6 capsid, or a variant AAV6 capsid such as ShH10, as described in U.S. PG Pub. 2012/0164106), AAV7, AAV8, AAVrh8, AAVrh8R, AAV9 (e.g., a wild-type AAV9 capsid, or a modified AAV9 capsid as described in U.S. PG Pub. 2013/0323226), AAV10, AAVrh10, AAV11, AAV12, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), AAV2 N587A capsid, AAV2 E548A capsid, AAV2 N708A capsid, AAV V708K capsid, goat AAV capsid, AAV1/AAV2 chimeric capsid, bovine AAV capsid, mouse AAV capsid, rAAV2/HBoV1 capsid, or an AAV capsid described in U.S. Pat. No. 8,283,151 or International Publication No. WO/2003/042397. In some embodiments, a mutant capsid protein maintains the ability to form an AAV capsid. In some embodiments, the encapsidation protein is an AAV5 tyrosine mutant capsid protein. In further embodiments, the rAAV particle comprises capsid proteins of an AAV serotype from Clades A-F. In some embodiments, the rAAV particles comprise an AAV1 capsid and a recombinant genome comprising AAV2 ITRs, a mutant AAV2 ITR and nucleic acid encoding an RNAi of the present disclosure. In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

Numerous methods are known in the art for production of adenoviral vector particles. For example, for a gutted adenoviral vector, the adenoviral vector genome and a helper adenovirus genome may be transfected into a packaging cell line (e.g., a 293 cell line). In some embodiments, the helper adenovirus genome may contain recombination sites flanking its packaging signal, and both genomes may be transfected into a packaging cell line that expresses a recombinase (e.g., the Cre/loxP system may be used), such that the adenoviral vector of interest is packaged more efficiently than the helper adenovirus (see, e.g., Alba, R. et al. (2005) *Gene Ther.* 12 Suppl 1:S18-27). Adenoviral vectors may be harvested and purified using standard methods, such as those described herein.

Numerous methods are known in the art for production of lentiviral vector particles. For example, for a third-generation lentiviral vector, a vector containing the lentiviral genome of interest with gag and pol genes may be co-transfected into a packaging cell line (e.g., a 293 cell line) along with a vector containing a rev gene. The lentiviral genome of interest also contains a chimeric LTR that promotes transcription in the absence of Tat (see Dull, T. et al. (1998) *J. Virol.* 72:8463-71). Lentiviral vectors may be harvested and purified using methods (e.g., Segura M M, et al., (2013) *Expert Opin Biol Ther.* 13(7):987-1011) described herein.

Numerous methods are known in the art for production of HSV particles. HSV vectors may be harvested and purified using standard methods, such as those described herein. For example, for a replication-defective HSV vector, an HSV genome of interest that lacks all of the immediate early (IE) genes may be transfected into a complementing cell line that provides genes required for virus production, such as ICP4, ICP27, and ICP0 (see, e.g., Samaniego, L. A. et al. (1998) *J. Virol.* 72:3307-20). HSV vectors may be harvested and purified using methods described (e.g., Goins, W F et al., (2014) Herpes Simplex Virus Methods in Molecular Biology 1144:63-79).

Also provided herein are pharmaceutical compositions comprising a recombinant viral particle comprising a transgene encoding an RNAi of the present disclosure and a pharmaceutically acceptable carrier. The pharmaceutical compositions may be suitable for any mode of administration described herein. A pharmaceutical composition of a recombinant viral particle comprising a nucleic acid encoding an RNAi of the present disclosure can be introduced to the brain. For example, a recombinant viral particle comprising a nucleic acid encoding an RNAi of the present disclosure can be administered intrastriatally. Any of the recombinant viral particles of the present disclosure may be used, including rAAV, adenoviral, lentiviral, and HSV particles.

In some embodiments, the pharmaceutical compositions comprising a recombinant viral particle comprising a transgene encoding an RNAi of the present disclosure described herein and a pharmaceutically acceptable carrier is suitable for administration to human. Such carriers are well known in the art (see, e.g., Remington's Pharmaceutical Sciences, 15th Edition, pp. 1035-1038 and 1570-1580). In some embodiments, the pharmaceutical compositions comprising a rAAV described herein and a pharmaceutically acceptable carrier is suitable for injection into the brain of a mammal (e.g., intrastriatal administration). In some embodiments, the pharmaceutical compositions comprising a recombinant lentiviral particle described herein and a pharmaceutically acceptable carrier is suitable for injection into the brain of a mammal (e.g., intrastriatal administration). In some embodiments, the pharmaceutical compositions comprising a recombinant adenoviral particle described herein and a pharmaceutically acceptable carrier is suitable for injection into the brain of a mammal (e.g., intrastriatal administration). In some embodiments, the pharmaceutical compositions comprising a recombinant HSV particle described herein and a pharmaceutically acceptable carrier is suitable for injection into the brain of a mammal (e.g., intrastriatal administration).

Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

VII. Articles of Manufacture and Kits

Also provided are kits or articles of manufacture for use in the methods described herein. In aspects, the kits comprise the compositions described herein (e.g., a recombinant viral particle of the present disclosure, such as a rAAV particle comprising nucleic acid encoding an RNAi of the present disclosure) in suitable packaging. Suitable packaging for compositions (such as intrastriatal compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein. For example, in some embodiments, the kit comprises a composition of recombinant viral particles comprising a transgene encoding an RNAi of the present disclosure for delivery of at least $1 \times 10^9$ genome copies into the brain of a mammal (e.g., through intrastriatal administration) to a primate as described herein, a pharmaceutically acceptable carrier suitable for injection into the brain of a primate, and one or more of: a buffer, a diluent, a filter, a needle, a syringe, and a package insert with instructions for performing injections into the brain of a primate (e.g., intrastriatal administration). In some embodiments, the kit comprising instructions for treating Huntington's disease with the recombinant viral particles described herein. In some embodiments, the kit comprising instructions for using the recombinant viral particles described herein according to any one of the methods described herein.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: AAV2/1-miRNA-Htt Reduces Htt Expression In Vitro

RNA interference (RNAi) provides an approach for the treatment of many human diseases. However, the safety of RNAi-based therapies can be hampered by the ability of small inhibitory RNAs (siRNAs) to bind to unintended mRNAs and reduce their expression, an effect known as off-target gene silencing. Off-targeting primarily occurs when the seed region (nucleotides 2-8 of the small RNA) pairs with sequences in 3'-UTRs of unintended mRNAs and directs translational repression and destabilization of those transcripts. To date, most therapeutic RNAi sequences are selected primarily for gene silencing efficacy, and later evaluated for safety. Two siRNAs were generated to treat Huntington's disease (HD), a dominant neurodegenerative disorder, with minimal off-targeting potential (i.e., those with a scarcity of seed complements within all known human and rhesus monkey 3'-UTRs) which demonstrates potent huntingtin silencing in the mouse brain with a low in silico off-target profile (Table 1, FIG. 1A). One sequence (207) was tested for its ability to rescue behavioral phenotypes in the YAC128 mouse model of HD. Striatal delivery of AAV2/1-miRNA-Htt-207 not only reduces Htt mRNA and protein levels in the brain, but also corrects the aberrant behavioral profiles in YAC128 mice and demonstrates high guide strand activity and precise 5' processing, minimizing the potential for off target effects.

TABLE 1 miRNA and reverse complement (target) sequences for 206 and 207 as well as the top and bottom sequences for cloning, including restriction site overhangs.

| miRNA ID | Component | Sequence | SEQ ID NO: |
|---|---|---|---|
| 206 | miRNA sequence (anti-sense, 5'→3') | uGGCCGUCCAUCUUGGACCCG | 1 |
| 206 | reverse complement (sense, 5'→3') | CGGGUCCAAGAUGGACGGCCa | 2 |
| 206 | DNA sequence encoding miRNA duplex | GTGGCCGTCCATCTTGGACC CGGTTTTGGCCACTGACTGA CCGGGTCCAATGGACGGCCA | 3 |
| 206 | RNA sequence of miRNA duplex | GUGGCCGUCCAUCUUGGACC CGGUUUUGGCCACUGACUGA CCGGGUCCAAUGGACGGCCA | 4 |
| 206 | top sequence for cloning (5'→3') stem loop that contains the actual miRNA sequence, including restriction site overhangs for cloning* | <u>TGCT</u>GTGGCCGTCCATCTTG GACCCGGTTTTGGCCACTGA CTGAC*CGGGTCC*AATGGACG GCCA | 5 |
| 206 | bottom sequence for cloning (5'→3') reverse complement of sequence in column to the left, including restriction site overhangs for cloning* | <u>CCTG</u>TGGCCGTCCAT*TGGAC CCG*GTCAGTCAGTGGCCAAA ACCGGGTCCAAGATGGACGG CCA<u>C</u> | 6 |
| 207 | miRNA sequence (anti-sense, 5'→3') | AGUCGGUGUGGUUGACAAGCA | 7 |
| 207 | reverse complement (sense, 5'→3') | UGCUUGUCAACCACACCGACU | 8 |
| 207 | DNA sequence encoding miRNA duplex | AGTCGGTGTGGTTGACAAGCA GTTTTGGCCACTGACTGACTG CTTGTCCCACACCGACT | 9 |
| 207 | RNA sequence of miRNA duplex | AGUCGGUGUGGUUGACAAGCA GUUUUGGCCACUGACUGACUG CUUGUCCCACACCGACU | 10 |
| 207 | top sequence for cloning (5'→3') stem loop that contains the actual miRNA sequence, including restriction site overhangs for cloning* | <u>TGCT</u>GAGTCGGTGTGGTTGA CAAGCAGTTTTGGCCACTGA CTGAC*TGCTTGTC*CCACACC GACT | 11 |
| 207 | bottom sequence for cloning (5'→3') reverse complement of sequence in column to the left, including restriction site overhangs for cloning* | <u>CCTG</u>AGTCGGTGTGG*GACAA GCA*GTCAGTCAGTGGCCAAA ACTGCTTGTCAACCACACCG ACT<u>C</u> | 12 |

*For sequences for cloning-Restriction site overhangs for cloning are underlined; miRNA sequences in bold; loop sequence in plain text; bases 1-8 of miRNA reverse complement in bold, italics: bases 11-21 (11-20 for 170XX) of miRNA reverse complement in italics.

The ability of AAV2/1-miRNA-Htt 206 and 207 to mediate human huntingtin mRNA reduction was tested in vitro using human embryonic kidney (HEK293) cells. AAV2/1-miRNA-206 and 207 expression plasmids, as well as a positive control plasmid (170XA) containing a miRNA sequence previously shown to reduce Htt levels by approximately 50%, were transfected HEK293 cells (8 replicates per treatment). Cells were transfected using Fugene transfection reagent and harvested 48 hours later. Total RNA was isolated using the TaqMan® Cells-to-CT™ Kit (Ambion). RNA levels were measured by quantitative real-time RT-PCR (conducted and analyzed on an ABI Prism 7500

Figure 2:
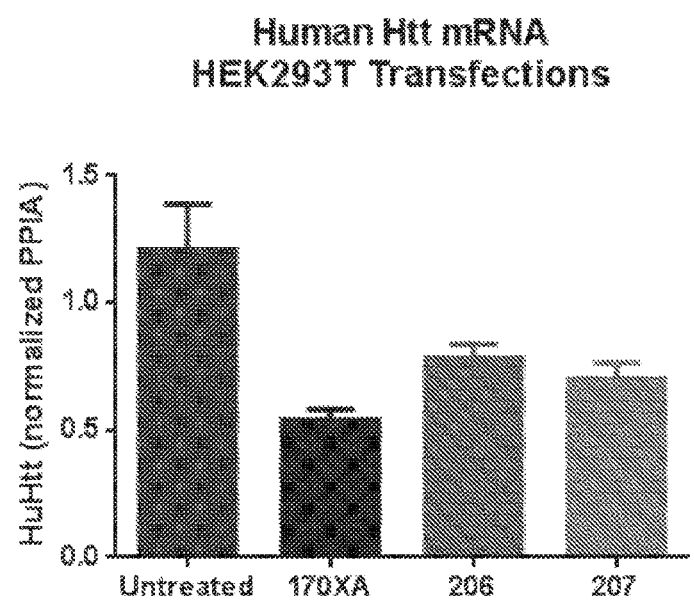
FIG. 2 shows the ability of Htt miRNA 170XA, Htt miRNA 206 and Htt miRNA 207 to mediate Htt reduction in vitro. Values are given as the means±SEM.

Sequence Detector (Applied Biosystems)). Expression levels were normalized to human PPIA (peptidylprolyl isomerase). As shown in FIG. 2, human Htt mRNA levels were reduced following transfection with both 206 and 207 plasmids compared to untreated untreated controls. Level of Htt reduction were nearly equivalent compared the 170XA positive control.

Example 2: AAV2/1-miRNA-Htt Reduces Htt Expression In Vivo

Figure 3A:
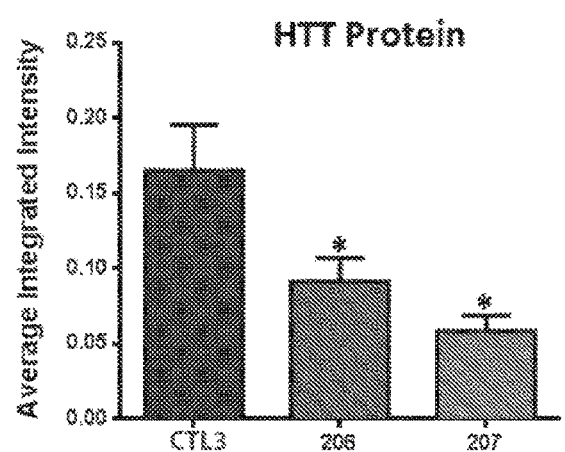
FIGS. 3A and 3B show the ability of AAV2/1-Htt miRNA 206 and AAV2/1-Htt miRNA 207 to mediate Htt reduction as measured by protein (FIG. 3A) or mRNA (FIG. 3B). CTL-3 is a noncoding miRNA control. Values are given as the means±SEM. * indicates significantly different from CTL3 mice, p<0.05; ANOVA followed by Tukey's post-hoc test.
Figure 3B:
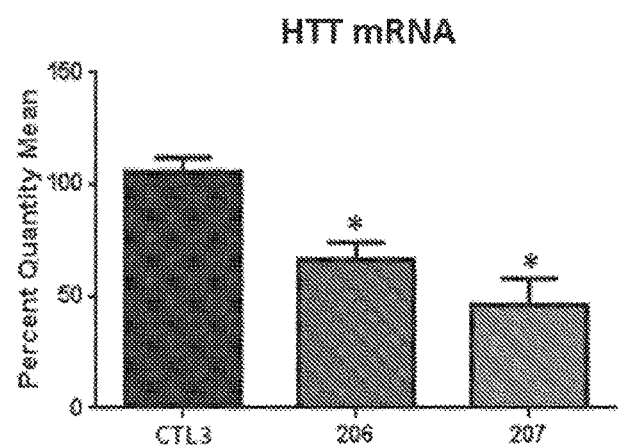

The ability of AAV2/1-miRNA-206 and 207 to reduce HTT protein levels in the striatum of YAC128 HD mice was tested. Adult YAC128 mice received bilateral intra-striatal injections of AAV2/1-miRNA-Htt 206 (1e10 vgs/site) or AAV2/1-miRNA-Htt 207 (1e10 vgs/site), or AAV2/1-CTL3 (a noncoding miRNA control) (1e10 vgs/site). One month following AAV injection, animals were sacrificed and perfused with PBS. Brains were collected for histology and biochemical analyses. For biochemical analyses the striatal region of one hemisphere was micro-dissected and snap frozen in liquid nitrogen. Striatal levels of mutant human and mouse Htt mRNA and HTT protein were evaluated by QPCR and Western blot respectively. Mutant human Htt and mouse Htt mRNA was significantly reduced in AAV2/1-miRNA-Htt 206 and AAV2/1-miRNA-Htt 207 injected mice when compared to CTL3 control animals (FIG. 3A). PPIA served as a normalization control gene for all QPCR assays. Mutant human and mouse HTT protein was significantly reduced in all AAV2/1-miRNA-Htt-injected mice when compared to CTL3 control animals and an equivalent extent of reduction (approximately 50%, $p<0.05$) was noted across all treatments (FIG. 3B). Beta-tubulin served as a normalization control gene for all western blots.

Figure 4A:
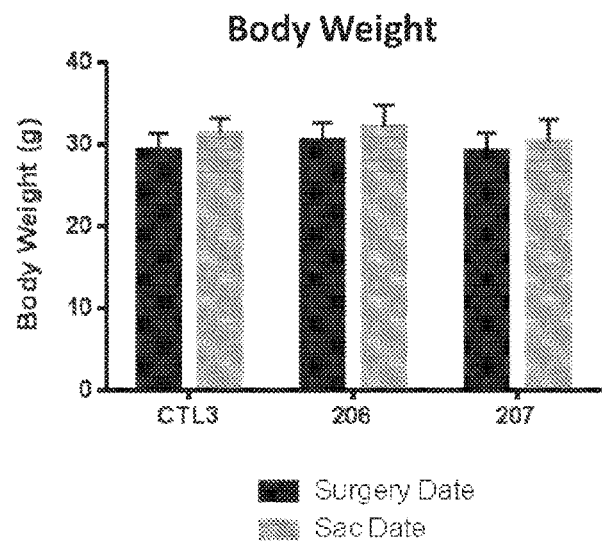
FIGS. 4A and 4B show body weight (FIG. 4A) and brain weight (FIG. 4B) one month after administration of AAV2/1-Htt miRNA 206 and AAV2/1-Htt miRNA 207. CTL-3 is a noncoding miRNA control. *Significantly different from CTL3 control mice, p<0.05; ANOVA followed by Tukey's post-hoc test.
Figure 4B:
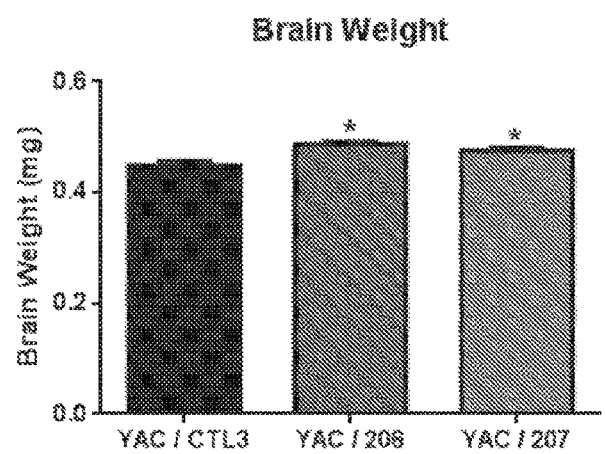

The effect of AAV2/1-miRNA-Htt 206 and 207 on brain and body weights of YAC128 mice was evaluated. Animal body weights on the day of surgery were compared to body weights taken on the day of sacrifice, 1 month post injection (FIG. 4A). There were no differences between AAV2/1-miRNA-Htt 206 and 207 compared to CTL3 controls. All mice appeared healthy, alert, and responsive one month post treatment and no weight loss was observed in any treatment group. Wet brain wets were recorded after PBS perfusion and brain dissection. A statistically significant increase in brain weights of YAC128 mice treated with AAV2/1-miRNA-Htt 206 and 207 was observed compared on CTL3 treated controls (FIG. 4B).

Figure 5A:
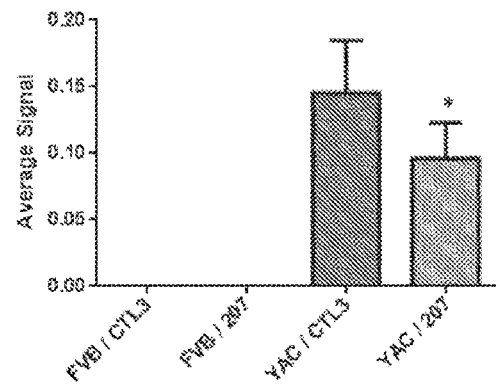
FIGS. 5A-5D show human Htt was significantly reduced in the striatum of AAV2/1-miRNA-Htt-207 injected YAC128 and FVB wild-type littermate mice. Human HTT protein levels are shown in FIG. 5A. Mouse HTT protein levels are shown in FIG. 5B. Human HTT mRNA levels are shown in FIG. 5C. Mouse HTT mRNA levels are shown in FIG. 5D.
Figure 5B:
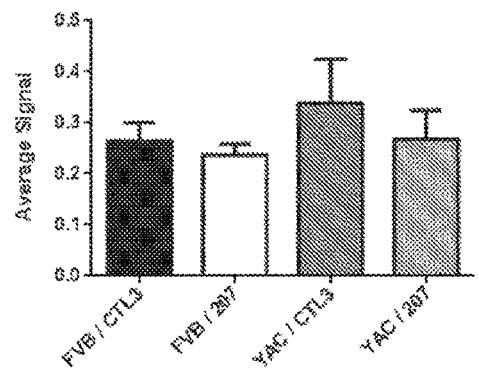
Figure 5C:
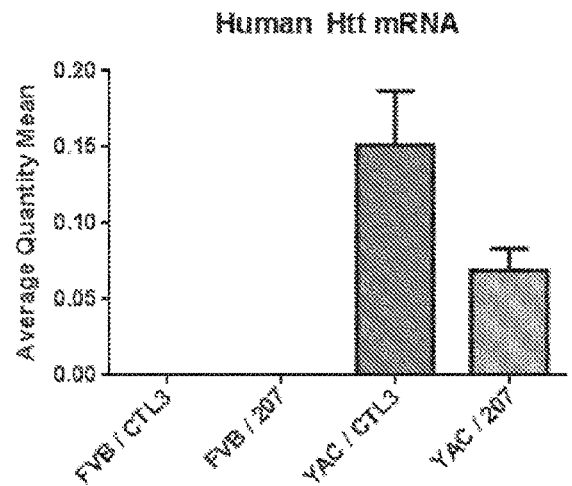
Figure 5D:
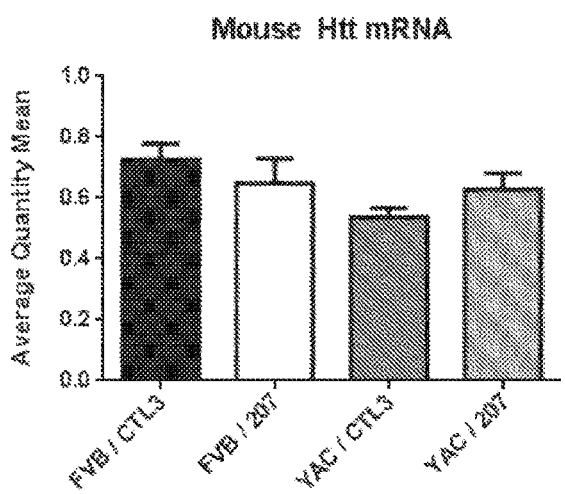

Example 3: AAV2/1-miRNA-Htt Corrects Behavioral and Coordination Deficits in YAC128 Mice The ability of striatal delivery of AAV2/1-miRNA-Htt-207 to correct the aberrant behavioral phenotypes in YAC128 mice was evaluated. The impact of the AAV2/1-miRNA-Htt 207 mediated reduction of mutant Htt levels on the well-characterized phenotypic deficits that are present in the YAC128 mouse model of HD was also examined. Age-matched (3 month old) YAC128 and FVB wild-type littermate mice received bilateral intra-striatal injections of either AAV2/1-miRNA-Htt-207 (2e10 vg/site) or AAV2/1-CTL3 control vector (2e10 vgs/site). Mice received behavioral testing and were sacrificed 3 months after treatment. Western blot analysis of brain homogenates showed the levels of mutant human HTT protein was significantly reduced in the striatum of AAV2/1-miRNA-Htt-207 injected YAC128 and FVB wild-type littermate mice (approximately 50% reduction, $p<0.01$) when compared to AAV2/1-CTL3-treated controls. Mouse HTT protein levels were not significantly reduced in this study (FIGS. 5A and 5B). Real-time quantitative PCR analysis indicated a commensurate reduction in mRNA levels (FIGS. 5C and 5D).

Figure 6A:
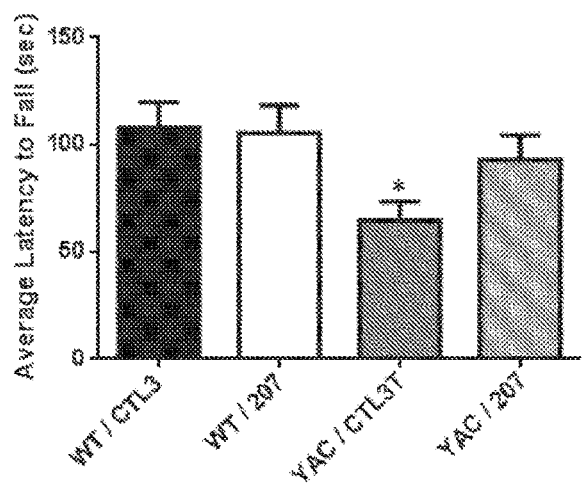
FIGS. 6A and 6B show that treatment with AAV2/1-miRNA-Htt-207 can correct motor coordination deficits in YAC128 mice as determined by rotarod test (FIG. 6A) and a depressive phenotype in YAC128 mice as determined using the Porsolt swim test (FIG. 6B). Mice were either wild type (WT also referred to as FVB) or YAC128 (YAC) treated with a non-coding RNA control (CTL3) or AAV2/1-miRNA-Htt-207 (207).
Figure 6B:
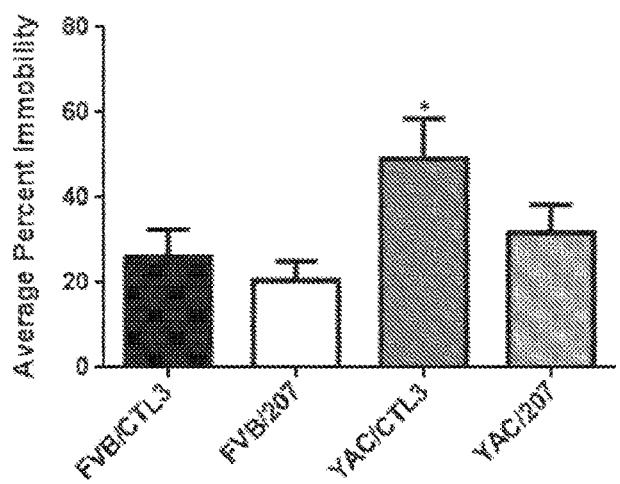

YAC128 mice have been reported to exhibit motor coordination deficits (which can be revealed using the rotarod test) and a depressive phenotype (which can be revealed using the Porsolt swim test) beginning at 3 months of age (Slow et al., 2003, Van Raamsdonk et al., 2007). Rotarod testing of AAV2/1-CTL3-treated YAC128 mice at 3 months post-injection showed significant motor coordination deficits when compared to AAV2/1-CTL3-treated wild-type littermates (ANOVA, $p<0.05$) (FIG. 6A). However, YAC128 mice that had been treated with AAV2/1-miRNA-Htt-207 showed performance levels that were indistinguishable from those of wild-type mice (ANOVA, Tukey's post-hoc; WT 207 vs. YAC128 207, p=NS; WT CTL3 vs. YAC128 CTL3, $p<0.05$). Hence, partial lowering of mutant Htt levels was sufficient to correct the motor deficits of YAC128 mice. There were no significant differences in rotarod performance between wild-type mice that received AAV2/1-miRNA-Htt-207 and wild-type mice that received AAV2/1-CTL3. Previous reports indicated that YAC128 mice exhibit a depressive phenotype that can be detected using the Porsolt swim test (Pouladi et al., 2009). Animals are deemed to exhibit a depressive state if they are immobile for an extended period when placed into a container of water. Using a basic swim speed test (where swim latency to reach a platform was measured) researchers have demonstrated that this depressive phenotype in the Porsolt swim test is unrelated to the swimming ability of YAC128 mice and is independent of the well documented motor coordination deficits observed in this model (Pouladi et al., 200). Three-month-old YAC128 and WT littermate mice were injected with AAV2/1-miRNA-Htt-207- or AAV2/1-CTL3-vectors and tested 3 months later in the Porsolt swim test. CTL3 treated YAC128 mice displayed an increased period of time in an immobile state when compared to either AAV2/1-miRNA-Htt-207-treated YAC mice or AAV2/1-CTL3-treated wild-type animals (FIG. 6B; ANOVA $p<0.05$). Again, there were no significant differences in the performance of wild-type mice that received either AAV2/1-miRNA-Htt or AAV2/1-CTL3. YAC28 mice that had been injected with AAV2/1-miRNA-Htt-207 spent significantly less time in an immobile state than AAV2/1-CTL3-treated controls. Indeed, the performance of AAV2/1-miRNA-Htt-207 treated YAC128 mice was similar to that of their wild-type littermates, suggesting a near-complete correction of this aberrant phenotype (ANOVA, Tukey's post-hoc; YAC207 vs. YAC CTL3, $p<0.05$).

Figure 7A:
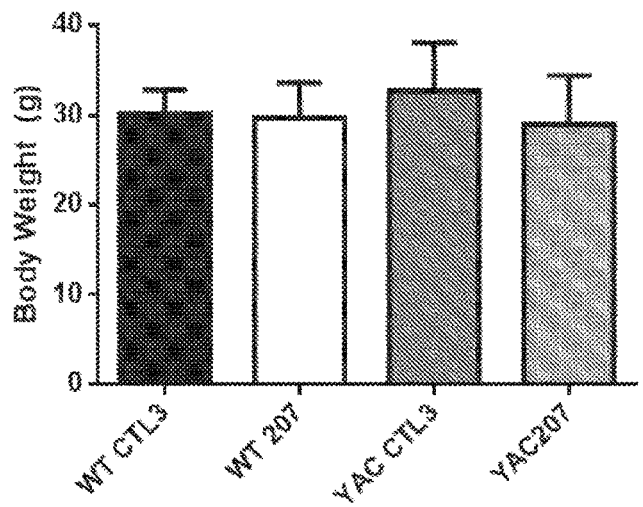
FIGS. 7A and 7B show body weights (FIG. 7A) and brain weights (FIG. 7B) three months post infection. Mice were either wild type (WT) or YAC128 (YAC) treated with a non-coding RNA control (CTL3) or AAV2/1-miRNA-Htt-207 (207).
Figure 7B:
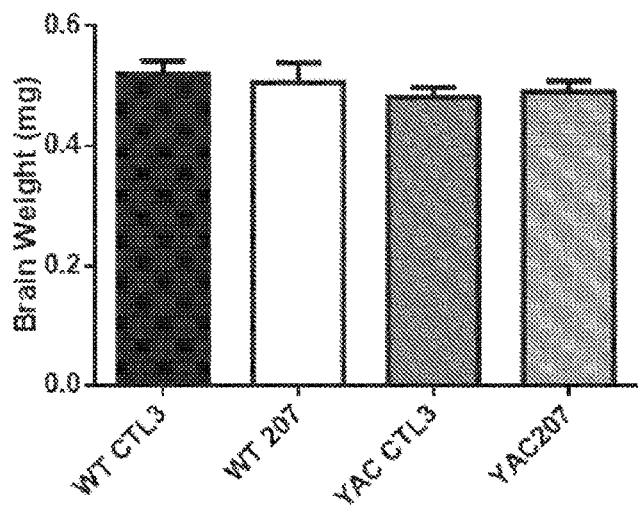

The effect of AAV2/1-miRNA-Htt 207 on brain and body weights of YAC128 mice was evaluated. Animal body weights on the day of surgery were compared to body weights taken on the day of sacrifice, 3 months post injection. There were no differences in body weight between AAV2/1-miRNA-Htt 207 treated mice compared to CTL3 treated controls (FIG. 7A). All mice appeared healthy, alert, and responsive three months post treatment and no weight loss was observed in any treatment group. Wet brain wets were recorded after PBS perfusion and brain dissection. There were no differences in brain weights of YAC128 mice treated with AAV2/1-miRNA-Htt 207 compared on CTL3 treated controls (FIG. 7B).

Example 4. miRNA's Demonstrate High Guide Activity and Precise 5' Processing Following In Vivo Delivery YAC128 mice were treated with AAV2/1-miRNA-Htt 206 or AAV2/1-miRNA-Htt 207 via intracranial injection. Post-treatment, the striatum was removed, and total RNA was isolated. Small RNA sequencing libraries were constructed using the NEBNext Small RNA Library Prep Set (New England Biolabs), and sequencing was performed on the Illumina MiSeq instrument. Samples from 2 separate mice were analyzed for each treatment. Here the total of all miRNA reads including endogenous sequences are shown as well as the total guide and passenger reads for each treatment vector. The AAV2/1-miRNA-Htt 202T vector treatment was included in this experiment as a control since it had been previously sequenced. The percent expected start position for each guide and passenger strand was >99%, and the 207 vector had high guide: passenger strand ratios of 76.1% and 79.3%.

TABLE 2

Guide activity and 5' processing

| Vector | 202T# | 206 | | 207 | |
|---|---|---|---|---|---|
| Sample ID # | 202 | 23 | 28 | 33 | 34 |
| Total Reads* | 1,898,745 | 3,184,602 | 3,307,273 | 3,386,131 | 2,599,808 |
| # Total Reads (guide) | 47,001 | 196 | 186 | 11,801 | 39,177 |
| % within expected start position | 99.1 | 100 | 99.5 | 97.9 | 97.6 |
| # Total Reads (passenger) | 465,981 | 554 | 719 | 3,075 | 12,327 |
| % within expected start position | 99.2 | 99.1 | 99.4 | 99.5 | 99.2 |
| % Guide | 0.2 | 26.1 | 20.6 | 79.3 | 79.1 |

Example 5. Self-Complementary miRHtt207 Vector

Figure 8:
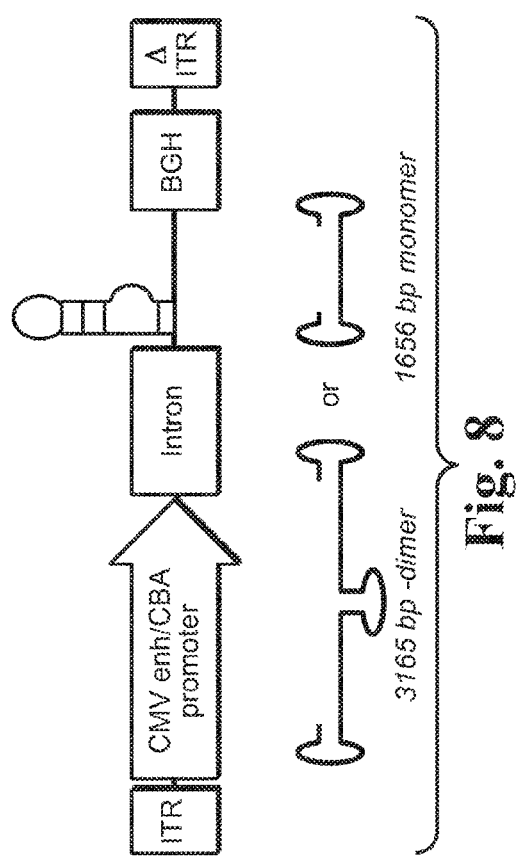
FIG. 8 shows a map of a self-complementary miRHtt 207 vector genome. CMV enh/CBA promoter is the CMV enhancer/chicken beta actin promoter. Δ chimeric intron is an abbreviated chimeric intron. BGH is the bovine growth hormone polyadenylation signal. ΔITR is an AAV ITR lacking the terminal resolution sequence.

The 207 miRHtt expression cassette can be packaged as a self-complementary vector genome. To achieve this, the ITR plasmid is designed to be only 2.3 kb in size, this facilitates packaging of a 4.6 kb dimeric vector; 4.6 kb is the packaging capacity of an AAV vector. The ITR plasmid can be designed to have a 5'WT ITR and a mutated D deleted, truncated 3'ITR (Δ ITR), as depicted in FIG. 8. The predicted vector genomes that could be packaged are the self-complementary vector genome, which would be 3165 bp, and would contain a 5' and 3' WT ITR and a third, internal, delta ITR (e.g., a chimeric intron). Additionally, it is expected that some monomeric vector genomes would be packaged, and these would be 1656 bp in size.

Figure 9:
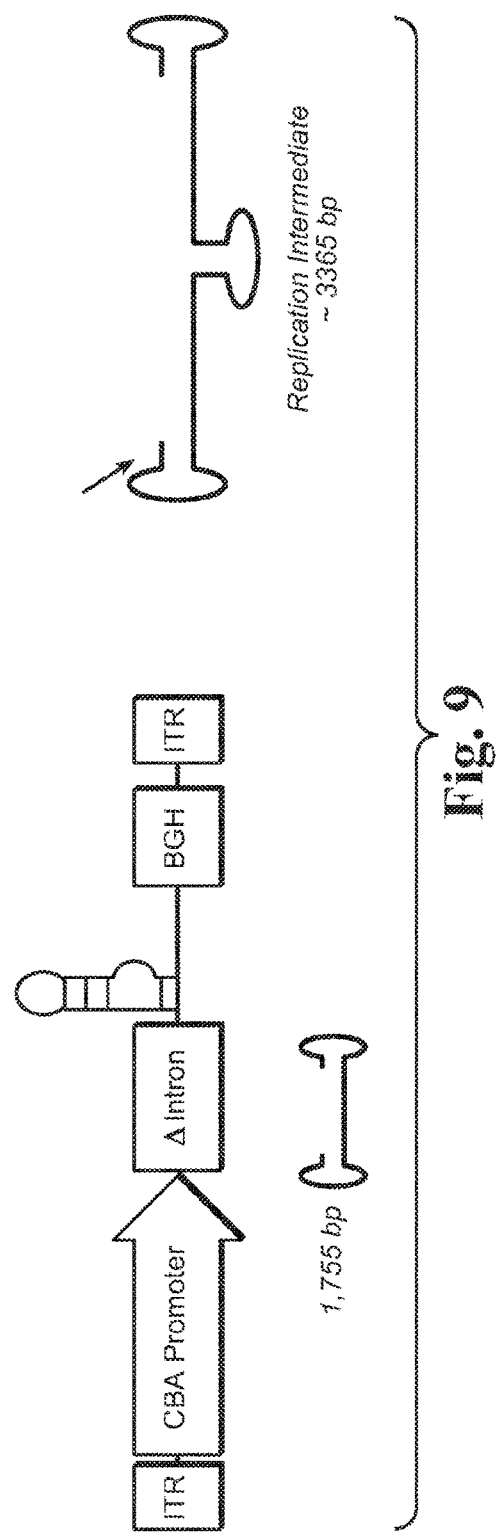
FIG. 9 shows a map of an alternative self-complementary miRHtt 207 vector genome. CBA promoter is the chicken beta actin promoter. Δ chimeric intron is an abbreviated chimeric intron. BGH is the bovine growth hormone polyadenylation signal.

An alternative approach to generating a self-complementary AAV miRHtt 207 vector i.e., packaging two vector genomes per capsid, would be to make a small, single stranded, i.e., 1755 bp vector genome, so that two copies of the vector genome are packaged as a replication intermediate species, 3365 bp, (FIG. 9). In this example the ITR plasmid would have a 5' and 3' WT ITR and the replication intermediate, 3365 bp, would have three WT ITRs, one 5' and 3' and one internal ITR. The single stranded vector gnome species, 1755 bp, could also be packaged.

```
ADDITIONAL SEQUENCES
All polypeptide sequences are presented as N-terminal to C-terminal unless
indicated otherwise. All nucleic acid sequences are presented as 5' to 3'
unless indicated otherwise.
miRNA scaffold DNA sequence
                                                            (SEQ ID NO: 14)
ctggaggcttgctgaaggctgtatgctgttagacaatgattcacacggtgttttggccactgactgacaccgtgt gtcattgtctaacaggacacaaggcctgttactagcactcacatggaacaaatggcc Variant AAV ITR for scAAV vectors
                                                            (SEQ ID NO: 15)
CCACTCCCTCTCTGCGCGCTCGCTCGCTCACTGAGGCCGGGCGACCAAAGGTCGCCCGACGCCCGGGCTTTGCCC

GGGCGGCCTCAGTGAGCGAGCGAGCGCGCAGAGAGGGA.
```

-continued ssAAV2/1miRHtt.de (SEQ ID NO: 16)
TTGGCCACTCCCTCTCTGCGCGCTCGCTCGCTCACTGAGGCCGCCCGGGCAAAGCCCGGGCGTCGGGCGACCTTT

GGTCGCCCGGCCTCAGTGAGCGAGCGAGCGCGCAGAGAGGGAGTGGCCAACTCCATCACTAGGGGTTCCTCTATA

TTACCCTGCTAGGCAATTGGATCCCGACCGTCGACATTGATTATTGACTAGTTATTAATAGTAATCAATTACGG

GGTCATTAGTTCATAGCCCATATATGGAGTTCCGCGTTACATAACTTACGGTAAATGGCCCGCCTGGCTGACCGC

CCAACGACCCCGCCCATTGACGTCAATAATGACGTATGTTCCCATAGTAACGCCAATAGGGACTTTCCATTGAC

GTCAATGGGTGGAGTATTTACGGTAAACTGCCCACTTGGCAGTACATCAAGTGTATCATATGCCAAGTACGCCCC

CTATTGACGTCAATGACGGTAAATGGCCCGCCTGGCATTATGCCCAGTACATGACCTTATGGGACTTTCCTACTT

GGCAGTACATCTACGTATTAGTCATCGCTATTACCATGGTCGAGGTGAGCCCCACGTTCTGCTTCACTCTCCCCA

TCTCCCCCCCCTCCCCACCCCCAATTTTGTATTTATTTATTTTTTAATTATTTTGTGCAGCGATGGGGGCGGGGG

GGGGGGGGGGGGCGCGCCAGGCGGGGCGGGGCGGGGCGAGGGGCGGGGCGGGGCGAGGCGGAGAGGTGCGGCGG

CAGCCAATCAGAGCGGCGCGCTCCGAAAGTTTCCTTTTATGGCGAGGCGGCGGCGGCGGCGGGCCTATAAAAAGC

GAAGCGCGCGGCGGGCGGGAGTCGCTGCGCGCTGCCTTCGCCCCGTGCCCCGCTCCGCCGCCGCCTCGCGCCGCC

CGCCCCGGCTCTGACTGACCGCGTTACTCCCACAGGTGAGCGGGCGGGACGGCCCTTCTCCTCCGGGCTGTAATT

AGCGCTTGGTTTAATGACGGCTTGTTTCTTTTCTGTGGCTGCGTGAAAGCCTTGAGGGGCTCCGGGAGGGCCCTT

TGTGCGGGGGAGCGGCTCGGGGGTGCGTGCGTGTGTGTGCGTGGGGAGCGCCGCGTGCGGCTCCGCGCTGC

CCGGCGGCTGTGAGCGCTGCGGGCGCGGCGCGGGGCTTTGTGCGCTCCGCAGTGTGCGCGAGGGGAGCGCGGCCG

GGGGCGGTGCCCCGCGGTGCGGGGGGGCTGCGAGGGGAACAAAGGCTGCGTGCGGGGTGTGTGCGTGGGGGGGT

GAGCAGGGGGTGTGGGCGCGTCGGTCGGGCTGCAACCCCCCTGCACCCCCCTCCCCGAGTTGCTGAGCACGGCC

CGGCTTCGGGTGCGGGGCTCCGTACGGGGCGTGGCGCGGGGCTCGCCGTGCCGGGCGGGGGGTGGCGGCAGGTGG

GGGTGCCGGGCGGGGCGGGGCCGCCTCGGGCCGGGGAGGGCTCGGGGGAGGGGCGCGGCGGCCCCCGGAGCGCCG

GCGGCTGTCGAGGCGCGGCGAGCCGGAGCCATTGCCTTTTATGGTAATCGTGCGAGAGGGCGCAGGGACTTCCTT

TGTCCCAAATCTGTGCGGAGCCGAAATCTGGGAGGCGCCGCCGCACCCCCTCTAGCGGGCGCGGGGCGAAGCGGT

GCGGCGCCGGCAGGAAGGAAATGGGCGGGAGGGCCTTCGTGCGTCGCCGCGCCGCCGTCCCCTTCTCCCTCTCC

AGCCTCGGGGCTGTCCGCGGGGGGACGGCTGCCTTCGGGGGGGACGGGGCAGGGCGGGGTTCGGCTTCTGGCGTG

TGACCGGCGGCTCTAGAGCCTCTGCTAACCATGTTCATGCCTTCTTCTTTTTCCTACAGCTCCTGGGCAACGTGC

TGGTTATTGTGCTGTCTCATCATTTTGGCAAAGAATTCTTCGAAAGATCTGCTAGCCTGGAGGCTTGCTGAAGGC

TGTATGCTGAGTCGGTGTGGTTGACAAGCAGTTTTGGCCACTGACTGACTGCTTGTCCCACACCGACTCAGGACA

CAAGGCCTGTTACTAGCACTCACATGGAACAAATGGCCATGCATCTAGAGGGCCCTATTCTATAGTGTCACCTAA

ATGCTAGAGCTCGCTGATCAGCCTCGACTGTGCCTTCTAGTTGCCAGCCATCTGTTGTTTGCCCCTCCCCCGTGC

CTTCCTTGACCCTGGAAGGTGCCACTCCCACTGTCCTTTCCTAATAAAATGAGGAAATTGCATCGCATTGTCTGA

*GTAGGTGTCATTCTATTCTGGGGGGTGGGGTGGGGCAGGACAGCAAGGGGGAGGATTGGGAAGACAATAGCAGGC*

*ATGCTGGGGAGCTAGAGTCGACCGACCGGTGGAAGTCCTCTTCCTCGGTGTCCTTGACTTCAAAGGGTCTCTCC*

*CATTTGCCTGGAGAGAGGGGAAGGTGGGCATCACCAGGGGTGAGTGAAGGTTTGGAAGAGTGTAGCAGAATAAGA*

*AACCATGAGTCCCCTCCCTGAGAAGCCCTGAGCCCCCTTGACGACACACATCCCTCGAGGCTCAGCTTCATCATC*

*TGTAAAAGGTGCTGAAACTGACCATCCAAGCTGCCGAAAAAGATTGTGTGGGATAATTCAAAACTAGAGGAAGA*

*TGCAGAATTTCTACATCGTGGCGATGTCAGGCTAAGAGATGCCATCGTGGCTGTGCATTTTTATTGGAATCATAT*

*GTTTATTTGAGGGTGTCTTGGATATTACAAATAAAATGTTGGAGCATCAGGCATATTTGGTACCTTCTGTCTAAG*

*GCTCCCTGCCCCTTGTTAATTGGCAGCTCAGTTATTCATCCAGGGCAAACATTCTGCTTACTATTCCTGAGAGCT*

*TTCCTCATCCTCTAGATTGGCAGGGGAAATGCAGATGCCTGAGCAGCCTCCCCTCTGCCATACCAACAGAGCTTC*

-continued

*ACCATCGAGGCATGCAGAGTGGACAGGGGCCTCAGGGACCCCTGATCCCAGCTTTCTCATTGGACAGAAGGAGGA*

*GACTGGGGCTGGAGAGGGACCTGGGCCCCCACTAAGGCCACAGCACAGCCAGGACTTTAGCTGTGCTGACTGCAC*

*CCTGGCTTGCCTCCACTGCCCTCCTTTGCCTCAAGAGCAAGGGAGCCTCAGAGTGGAGGAAGCAGCCCCTGGCCT*

*TGCCTCCCACCTCCCCTCCCCTATGCTGTTTTCCTGGGACAGTGGGAGCTGGCTTAGAATGCCCTGGGGCCCCCA*

*GGACCCTGGCATTTTAACCCCTCAGGGGCAGGAAGGCAGCCTGAGATACAGAAGAGTCCATCACCTGCTGTATGC*

*CACACACCATCCCCACAGTTACGTACTAGTTCGAAGCCACGCGGACCGTTATAGTTACGAGGAACCCCTAGTGAT*

GGAGTTGGCCACTCCCTCTCTGCGCGCTCGCTCGCTCACTGAGGCCGGGCGACCAAAGGTCGCCCGACGCCCGGG

CTTTGCCCGGGCGGCCTCAGTGAGCGAGCGAGCGCGCAGAGAGGGAGTGGCCAAAGATCT
mIR207 DNA sequence shown in bold (SEQ ID NO: 17)
Stuffer sequence shown in italics (SEQ ID NO: 18)

Portion of A1AT gene
(SEQ ID NO: 20)
aattcgcccttgggctaggcaattggatccgccggcagagaaaacatcccaggattttacagatcacatgcagg cagggaccagctcaaccccttctttaatgtcatccagggaggggccagggatggaggggaggggttgaggagcga gaggcagttattttggggtgggattcaccacttttcccatgaagaggggagacttggtattttgttcaatcatta agaagacaaagggtttgttgaacttgacctcggggggatagacatgggtatggcctctaaaaacatggccccag cagcttcagtcccttctcgtcgatggtcagcacagccttatgcacggcctggaggggagagaagcagagacacg ttgtaaggctgatcccaggcctcgagcaaggctcacgtggacacctcccaggaagcgctcactcccctggacgg ccctggccctgcacatcctctccctccctgtcacataggccttgctcctcctcaaggctttggctgatgggctg gctcccctctgtccatcttcctgacaagcgcctctcccctgctcaggtgcacccacaactcagaacagggaaga gcatcgtcactccacgtctgcctccagggctctctcctttctagtacacggcttgaagctccttgaggacacgga ccctggcagtgaccttcacagtgcccagaccccaagataatgcagccattcatggaactgcaggttgttcattgg tcgcctttagttttccaaaataagtgtcactttagctgaaatcattcattaattcagacaccaaatctcacagat cgaaggagtcagaaattcctttgaaacaacttagcccaaacctttctgtgtcagtatggataaatcaaggcccaa tgtctagaaggtcttgggcaaagttgaaattcagggtcagtgacacaacctcaagggaggccccgaaagtgccag ctgcacagcagcccctgcctggctttgctgtttgccaccgtcccgtgtcagtgaatcacgggcatcttcaggag ctcagcctgggtcttcatttgtttccctcggccccttcctcagcctcaggacagtgctgcagcccccacacattc ttccctacagataccatggtgcaacaaggtcgtcagggtgatctcaccttggagagcttcaggggtgcctcctct gtgaccccggagaggtcagccccattgctgaagaccttagtgatgcccagttgacccaggacgctcttcagatca taggttccagtaatggacagtttgggtaaatgtaagctggcagacctgtcgtgcagaaaagaaattcaaggcatg gcacagcattcctcttgttcttctgggacccaccacagtgcaagtgttttctttttctgattatttctgccactta ctcctgtgtcctccacccacactaagatgggaactcggctttggtttgttctacttttagctcttctacattgag tcaaagaatgttaacatcgaatgaatcacaaaagcttgaaatgccacctcctctgatattctaggtgtcctggaa gcctgtctcatcttgccctgtagtgttgggtcacctggccccagcctgtaacatccccagggccctacacccag agaaacacggggctggtggcagtgcccagtgacaaccgtttagtggataagagaagagtgaccacaccaggctga gtgctcctctctggttttccatggggagacaatgccaccctgagcagggtctggtgtgagcggcagctggctctg ggctctctgatccgttaccctctcagcctcttttgttctttctcaaccctggagcagagacctcaggaggtgctg gcatggaacagagaaattccagcctcgattcctattatgaacccgacacctttgtattttcatcttggttttac agtgtacaaaacgaactagatcagcagggcatgggcataatcacgaatgcacacacatacactaatgtgtggctc atgtttaagtatcacttactacaggacacccaatctaacagcaccgataaagtgacagagaaacgcaagccttct gcgaacatggcctggctgttccaattccgaaccttgcttttctgggccttgccacacaggctcttcccccgtccc cccagggacattctaccccttgaactccacactccactgctgcctttgccaggaagcccatctgttccttttggt tctgccagaacgtgtggtggtgctgctgtccctgccttgggcactggatattgggaagggacagtgtccacactg

```
gagtgggaagttcccagggacgagacctttacctcctcaccctgggtactgttctcctcatggagcatggacggc gctgcctgaactcagtggtggcctcattctggaagccaagtttatacagagtagcagtgacccagggatgtgggg ttcaccctcctcagccctctggccagtcctgatgggcctcagtcccaacatggctaagaggtgtgggcagcttct tggtcaccctcaggttggggaatcaccttctgtcttcattttccaggaacttggtgatgatatcgtgggtgagtt catttaccaggtgctgtagtttcccctcatcaggcaggaagaagatggcggtggcattgcccaggtatttcatca gcagcacccagctggacagcttcttacagtgctggatgttaaacatgcctaaacgcttcatcataggcaccttca cggtggtcacctggtccacgtggaagtcctcttcctcggtgtccttgacttcaaagggtctctcccatttgcctg gagagaggggaaggtgggcatcaccaggggtgagtgaaggtttggaagagtgtagcagaataagaaaccatgagt cccctccctgagaagccctgagccccttgacgacacacatccctcgaggctcagcttcatcatctgtaaaaggt gctgaaactgaccatccaagctgccgaaaaagattgtgtggggataattcaaaactagaggaagatgcagaattt ctacatcgtggcgatgtcaggctaagagatgccatcgtggctgtgcattttattggaatcatatgtttatttga gggtgtcttggatattacaaataaaatgttggagcatcaggcatatttggtaccttctgtctaaggctccctgcc ccttgttaattggcagctcagttattcatccagggcaaacattctgcttactattcctgagagctttcctcatcc tctagattggcaggggaaatgcagatgcctgagcagcctccctctgccataccaacagagcttcaccatcgagg catgcagagtggacaggggcctcagggacccctgatcccagctttctcattggacagaaggaggagactgggct ggagagggacctggcccccactaaggccacagcagagccaggactttagctgtgctgactgcagcctggcttgc ctccactgccctcctttgcctcaagagcaagggagcctcagagtggaggaagcagcccctggccttgcctcccac ctccctccctatgctgtttcctgggacagtgggagctggcttagaatgccctgggcccccaggaccctggc attttaacccctcagggcaggaaggcagcctgagatacagaagagtccatcacctgctgtatgccacacaccat ccccacagttacgtactagttcgaagccacgcgtccgaagggcgaatt
```
Stuffer sequence used in some embodiments is underlined Delta chimeric intron sequence (SEQ ID NO: 21)
```
ggagtcgctgcgcgctgccttcgccccgtgccccgctccgccgccgcctcgcgccgcccgccccggctctgactg accgcgttactcccacaggtgagcgggcgggacgcccttctcctccgggctgtaattagcgcttggtttaatga cggcttgtttcttttctgtggctgcgtgaaagccttgaggggctccgggagctagagcctctgctaaccatgttc atgccttcttctttttcctacagctcctgggcaacgtgctggttattgtgctgtctcatcattttggcaaagaat tcctcgaagatccggtacccaattccggggcccccacgctgcgcatccgcg
```

---

What is claimed is:

1. An RNAi comprising a first strand and a second strand, wherein
   a) the first strand and the second strand form a duplex;
   b) the first strand comprises a guide region, wherein the guide region comprises the nucleic acid sequence 5'-UGGCCGUCCAUCUUGGACCCG-3' (SEQ ID NO:1) or a nucleic acid sequence having more than 90% identity to SEQ ID NO: 1; or 5'-AGUCGGU-GUGGUUGACAAGCA-3' (SEQ ID NO:7), or a nucleic acid sequence having more than 90% identity to SEQ ID NO: 7; and
   c) the second strand comprises a non-guide region.

2. The RNAi of claim 1, wherein the nucleic the guide region comprises the nucleic acid sequence 5'-UGGCCGU-CCAUCUUGGACCCG-3' (SEQ ID NO:1), or a nucleic acid sequence having more than 90% identity to SEQ ID NO: 1; and the non-guide region comprises the sequence 5'-CGGGUCCAAGAUGGACGGCCA-3' (SEQ ID NO:2), or a nucleic acid sequence having more than 90% identity to SEQ ID NO: 2.

3. The RNAi of claim 1, wherein the nucleic the guide region comprises the nucleic acid sequence 5'-AGUCGGU-GUGGUUGACAAGCA-3' (SEQ ID NO:7), or a nucleic acid sequence having more than 90% identity to SEQ ID NO: 7; and the non-guide region comprises the sequence 5'-UGCUUGUCAACCACACCGACU-3' (SEQ ID NO:8), or a nucleic acid sequence having more than 90% identity to SEQ ID NO: 8.

4. The RNAi of claim 1, wherein the first strand and the second strand are linked by means of a RNA linker capable of forming a loop structure, and wherein the RNA linker comprises from 4 to 50 nucleotides or 4 to 20 nucleotides.

5. The RNAi of claim 1, wherein the RNAi comprises the nucleic acid sequence of SEQ ID NO:4 or SEQ ID NO:10, or a nucleotide sequence more than 90% identical to the nucleotide sequence of SEQ ID NO:4 or SEQ ID NO:10.

6. The RNAi of claim 1, wherein the RNAi is a small inhibitory RNA (siRNA), a microRNA (miRNA), or a small hairpin RNA (shRNA).

7. The RNAi of claim 1, wherein the RNAi targets RNA encoding a polypeptide associated with Huntington's disease.

8. The RNAi of claim 7, wherein the polypeptide is huntingtin.

9. The RNAi of claim 8, wherein the huntingtin comprises a mutation associated with Huntington's disease.

10. An expression construct comprising nucleic acid encoding the RNAi of claim 1.

11. The expression construct of claim 10 wherein the nucleic acid encoding the RNAi comprises a miRNA scaffold.

12. The expression construct of claim 10, wherein the nucleic acid encoding the RNAi is operably linked to a promoter, and wherein the promoter is selected from a cytomegalovirus (CMV) immediate early promoter, an RSV LTR, a MoMLV LTR, a phosphoglycerate kinase-1 (PGK) promoter, a simian virus 40 (SV40) promoter, a CK6 promoter, a transthyretin promoter (TTR), a TK promoter, a tetracycline responsive promoter (TRE), an HBV promoter, an hAAT promoter, a LSP promoter, a chimeric liver-specific promoter (LSP), an E2F promoter, a telomerase (hTERT) promoter; a cytomegalovirus enhancer/chicken beta-actin/Rabbit β-globin promoter (CAG) promoter, an elongation factor 1-alpha promoter (EF1-alpha) promoter, a human β-glucuronidase promoter, a chicken β-actin (CBA) promoter, a retroviral Rous sarcoma virus (RSV) LTR promoter, a dihydrofolate reductase promoter, and a 13-actin promoter.

13. The expression construct of claim 10, wherein the expression construct further comprises an intron.

14. The expression construct of claim 13, wherein the expression vector is a self-complementary vector and the intron is a delta chimeric intron.

15. The expression construct of claim 10, wherein the expression construct further comprises a polyadenylation signal, and wherein the polyadenylation signal is a bovine growth hormone polyadenylation signal, an SV40 polyadenylation signal, or a HSV TK pA.

16. A vector comprising the expression construct of claim 10.

17. The vector of claim 16, wherein the vector is a recombinant adeno-associated virus (rAAV) vector, a recombinant adenoviral vector, a recombinant lentiviral vector or a recombinant herpes simplex virus (HSV) vector.

18. The vector of claim 17, wherein the vector is a rAAV vector.

19. The rAAV vector of claim 18, wherein the expression construct is flanked by one or more AAV inverted terminal repeat (ITR) sequences.

20. The rAAV vector of claim 19, wherein the AAV ITRs are AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITRs.

21. The rAAV vector of claim 19, wherein the vector is a self-complementary rAAV vector.

22. The rAAV vector of claim 21, wherein the vector comprises first nucleic acid sequence encoding the RNAi and a second nucleic acid sequence encoding a complement of the RNAi, wherein the first nucleic acid sequence can form intrastrand base pairs with the second nucleic acid sequence along most or all of its length.

23. The rAAV vector of claim 22, wherein the first nucleic acid sequence and the second nucleic acid sequence are linked by a mutated AAV ITR, wherein the mutated AAV ITR comprises a deletion of the D region and comprises a mutation of the terminal resolution sequence.

24. An isolated cell comprising the vector of claim 16.

25. A recombinant AAV particle comprising the rAAV vector of claim 19.

26. The rAAV particle of claim 25, wherein the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, AAV2-HBKO, AAVDJ8, AAVPHP.B, AAVPHP.eB, AAVBR1, AAVHSC15, AAVHSC17, a goat AAV, AAV1/AAV2 chimeric, bovine AAV, or mouse AAV capsid rAAV2/HBoV1 serotype capsid.

27. The rAAV particle of claim 25, wherein the ITR is derived from AAV2 and the capsid of the rAAV particle is derived from AAV1.

28. A composition comprising the rAAV particle of claim 25.

29. A kit comprising the RNAi of claim 1, further comprising instructions for use.

30. A method for treating Huntington's disease in a mammal comprising administering to the mammal the RNAi of claim 1.

31. A method for inhibiting the expression or the accumulation of htt in a cell of a mammal with Huntington's disease comprising administering to the mammal the RNAi of claim 1.

32. The RNAi of claim 1, wherein the guide region comprises the nucleic acid sequence of SEQ ID NO:1.

33. The RNAi of claim 1, wherein the guide region comprises a nucleic acid sequence of more than 90% identity to the nucleic acid sequence of SEQ ID NO:1 and maintains at least one CpG motif.

34. The RNAi of claim 1, wherein the guide region comprises a nucleic acid sequence of more than 95% identity to the nucleic acid sequence of SEQ ID NO:1 and maintains at least one CpG motif.

35. The RNAi of claim 1, wherein the guide region comprises the nucleic acid sequence of SEQ ID NO:7.

36. The RNAi of claim 1, wherein the guide region comprises a nucleic acid sequence of more than 90% identity to the nucleic acid sequence of SEQ ID NO:7 and maintains at least one CpG motif.

37. The RNAi of claim 1, wherein the guide region comprises a nucleic acid sequence of more than 95% identity to the nucleic acid sequence of SEQ ID NO:7 and maintains at least one CpG motif.

38. The RNAi of claim 2, wherein the guide region comprises the nucleic acid sequence of SEQ ID NO:1, and the non-guide region comprises the sequence of SEQ ID NO:2.

39. The RNAi of claim 2, wherein the guide region comprises a nucleic acid sequence of more than 90% identity to the nucleic acid sequence of SEQ ID NO:1 and maintains at least one CpG motif, and the non-guide region comprises a nucleic acid sequence of more than 90% identity to the nucleic acid sequence of SEQ ID NO:2 and maintains at least one CpG motif.

40. The RNAi of claim 2, wherein the guide region comprises a nucleic acid sequence of more than 95% identity to the nucleic acid sequence of SEQ ID NO:1 and maintains at least one CpG motif, and the non-guide region comprises a nucleic acid sequence of more than 95% identity to the nucleic acid sequence of SEQ ID NO:2 and maintains at least one CpG motif.

41. The RNAi of claim 3, wherein the guide region comprises the nucleic acid sequence of SEQ ID NO:7, and the non-guide region comprises the sequence of SEQ ID NO:8.

42. The RNAi of claim 3, wherein the guide region comprises a nucleic acid sequence of more than 90% identity to the nucleic acid sequence of SEQ ID NO:7 and maintains at least one CpG motif, and the non-guide region comprises a nucleic acid sequence of more than 90% identity to the nucleic acid sequence of SEQ ID NO:8 and maintains at least one CpG motif.

43. The RNAi of claim 3, wherein the guide region comprises a nucleic acid sequence of more than 95% identity to the nucleic acid sequence of SEQ ID NO:7 and maintains at least one CpG motif, and the non-guide region comprises a nucleic acid sequence of more than 95% identity to the nucleic acid sequence of SEQ ID NO:8 and maintains at least one CpG motif.

* * * * *

SEQUENCE LISTING

<160> NUMBER OF SEQ ID NOS: 22

<210> SEQ ID NO 1
<211> LENGTH: 21
<212> TYPE: RNA
<213> ORGANISM: Artificial Sequence
<220> FEATURE:
<223> OTHER INFORMATION: Synthetic Construct

<400> SEQUENCE: 1
uggccgucca ucuuggaccc g                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic Construct

<400> SEQUENCE: 2
cggguccaag auggacggcc a            21

<210> SEQ ID NO 3
<211> LENGTH: 60
<212> TYPE: DNA
<213> ORGANISM: Artificial Sequence
<220> FEATURE:
<223> OTHER INFORMATION: Synthetic Construct

<400> SEQUENCE: 3
gtggccgtcc atcttggacc cggttttggc cactgactga ccgggtccaa tggacggcca            60

<210> SEQ ID NO 4
<211> LENGTH: 60
<212> TYPE: RNA
<213> ORGANISM: Artificial Sequence
<220> FEATURE:
<223> OTHER INFORMATION: Synthetic Construct

<400> SEQUENCE: 4
guggccgucc aucuuggacc cgguuuuggc cacugacuga ccgguccaa uggacggcca            60

<210> SEQ ID NO 5
<211> LENGTH: 64
<212> TYPE: DNA
<213> ORGANISM: Artificial Sequence
<220> FEATURE:
<223> OTHER INFORMATION: Synthetic Construct

<400> SEQUENCE: 5
tgctgtggcc gtccatcttg gacccggttt tggccactga ctgaccgggt ccaatggacg            60
gcca            64

<210> SEQ ID NO 6
<211> LENGTH: 64
<212> TYPE: DNA
<213> ORGANISM: Artificial Sequence
<220> FEATURE:
<223> OTHER INFORMATION: Synthetic Construct

<400> SEQUENCE: 6
cctgtggccg tccattggac ccggtcagtc agtggccaaa accgggtcca agatggacgg            60
ccac            64

<210> SEQ ID NO 7
<211> LENGTH: 21
<212> TYPE: RNA
<213> ORGANISM: Artificial Sequence
<220> FEATURE:
<223> OTHER INFORMATION: Synthetic Construct

<400> SEQUENCE: 7
agucggugug guugacaagc a            21

<210> SEQ ID NO 8
<211> LENGTH: 21
<212> TYPE: RNA
<213> ORGANISM: Artificial Sequence
<220> FEATURE:
<223> OTHER INFORMATION: Synthetic Construct

<400> SEQUENCE: 8
ugcuugucaa ccacaccgac u            21

<210> SEQ ID NO 9
<211> LENGTH: 59
<212> TYPE: DNA
<213> ORGANISM: Artificial Sequence
<220> FEATURE:
<223> OTHER INFORMATION: Synthetic Construct

<400> SEQUENCE: 9
agtcggtgtg gttgacaagc agttttggcc actgactgac tgcttgtccc acaccgact    59

<210> SEQ ID NO 10
<211> LENGTH: 59
<212> TYPE: RNA
<213> ORGANISM: Artificial Sequence
<220> FEATURE:
<223> OTHER INFORMATION: Synthetic Construct

<400> SEQUENCE: 10
agucggugug guugacaagc aguuuuggcc acugacugac ugcuuguccc acaccgacu    59

<210> SEQ ID NO 11
<211> LENGTH: 64
<212> TYPE: DNA
<213> ORGANISM: Artificial Sequence
<220> FEATURE:
<223> OTHER INFORMATION: Synthetic Construct

<400> SEQUENCE: 11
tgctgagtcg gtgtggttga caagcagttt tggccactga ctgactgctt gtcccacacc    60
gact    64

<210> SEQ ID NO 12
<211> LENGTH: 64
<212> TYPE: DNA
<213> ORGANISM: Artificial Sequence
<220> FEATURE:
<223> OTHER INFORMATION: Synthetic Construct

<400> SEQUENCE: 12
cctgagtcgg tgtgggacaa gcagtcagtc agtggccaaa actgcttgtc aaccacaccg    60
actc    64

<210> SEQ ID NO 13
<211> LENGTH: 19
<212> TYPE: RNA
<213> ORGANISM: Artificial Sequence
<220> FEATURE:
<223> OTHER INFORMATION: Synthetic Construct

<400> SEQUENCE: 13
guuuuggcca cugacugac    19

<210> SEQ ID NO 14
<211> LENGTH: 132
<212> TYPE: DNA
<213> ORGANISM: Artificial Sequence
<220> FEATURE:
<223> OTHER INFORMATION: Synthetic Construct -continued

<400> SEQUENCE: 14
ctggaggctt gctgaaggct gtatgctgtt agacaatgat tcacacggtg ttttggccac    60
tgactgacac cgtgtgtcat tgtctaacag gacacaaggc ctgttactag cactcacatg   120
gaacaaatgg cc                                                        132

<210> SEQ ID NO 15
<211> LENGTH: 113
<212> TYPE: DNA
<213> ORGANISM: Artificial Sequence
<220> FEATURE:
<223> OTHER INFORMATION: Synthetic Construct

<400> SEQUENCE: 15
ccactccctc tctgcgcgct cgctcgctca ctgaggccgg cgaccaaag gtcgcccgac     60 gcccgggctt tgcccgggcg gcctcagtga gcgagcgagc gcgcagagag gga           113

<210> SEQ ID NO 16
<211> LENGTH: 3510
<212> TYPE: DNA
<213> ORGANISM: Artificial Sequence
<220> FEATURE:
<223> OTHER INFORMATION: Synthetic Construct

<400> SEQUENCE: 16
ttggccactc cctctctgcg cgctcgctcg ctcactgagg ccgcccgggc aaagcccggg    60
cgtcgggcga cctttggtcg cccggcctca gtgagcgagc gagcgcgcag agagggagtg   120
gccaactcca tcactagggg ttcctctata ttaccctgct aggcaattgg atcccggacc   180
gtcgacattg attattgact agttattaat agtaatcaat tacggggtca ttagttcata   240
gcccatatat ggagttccgc gttacataac ttacggtaaa tggcccgcct ggctgaccgc   300
ccaacgaccc ccgcccattg acgtcaataa tgacgtatgt tcccatagta acgccaatag   360
ggactttcca ttgacgtcaa tgggtggagt atttacggta aactgcccac ttggcagtac   420
atcaagtgta tcatatgcca agtacgcccc ctattgacgt caatgacggt aaatggcccg   480
cctggcatta tgcccagtac atgaccttat gggactttcc tacttggcag tacatctacg   540
tattagtcat cgctattacc atggtcgagg tgagccccac gttctgcttc actctcccca   600
tctccccccc ctccccaccc ccaatttgt atttatttat tttttaatta ttttgtgcag    660 cgatggggc ggggggggg ggggggcgcg cgccaggcgg ggcggggcgg ggcgagggc      720 ggggcgggc gaggcggaga ggtgcggcgg cagccaatca gagcggcgcg ctccgaaagt   780
ttccttttat ggcgaggcgg cggcggcggc ggccctataa aaagcgaagc gcgcggcggg   840
cgggagtcgc tgcgcgctgc cttcgccccg tgccccgctc cgccgccgcc tcgcgccgcc   900
cgccccggct ctgactgacc gcgttactcc cacaggtgag cgggcgggac ggcccttctc   960
ctccgggctg taattagcgc ttggtttaat gacggcttgt ttcttttctg tggctgcgtg  1020
aaagccttga ggggctccgg gagggccctt tgtgcggggg gagcggctcg ggggtgcgt   1080 gcgtgtgtgt gtgcgtgggg agcgccgcgt gcggctccgc gctgcccggc ggctgtgagc  1140
gctgcgggcg cggcgcgggg ctttgtgcgc tccgcagtgt gcgcgagggg agcgcggccg  1200
ggggcggtgc cccgcggtgc gggggggcgct gcgagggaa caaaggctgc gtgcggggtg  1260
tgtgcgtggg ggggtgagca gggggtgtgg gcgcgtcggt cgggctgcaa cccccctgc   1320 acccccctcc ccgagttgct gagcacggcc cggcttcggg tgcggggctc cgtacggggc  1380

```
gtggcgcggg gctcgccgtg ccgggcgggg ggtggcggca ggtgggggtg ccgggcgggg      1440
cggggccgcc tcgggccggg gagggctcgg gggagggggcg cggcggcccc cggagcgccg      1500
gcggctgtcg aggcgcggcg agccgcagcc attgccttt  atggtaatcg tgcgagaggg      1560
cgcagggact tcctttgtcc caaatctgtg cggagccgaa atctgggagg cgccgccgca      1620 cccctctag cgggcgcggg gcgaagcggt gcggcgccgg caggaaggaa atgggcgggg      1680
agggccttcg tgcgtcgccg cgccgccgtc cccttctccc tctccagcct cggggctgtc      1740
cgcgggggga cggctgcctt cggggggggac ggggcagggc ggggttcggc ttctggcgtg      1800
tgaccggcgg ctctagagcc tctgctaacc atgttcatgc cttcttcttt ttcctacagc      1860
tcctgggcaa cgtgctggtt attgtgctgt ctcatcattt tggcaaagaa ttcttcgaaa      1920
gatctgctag cctggaggct tgctgaaggc tgtatgctga gtcggtgtgg ttgacaagca      1980
gttttggcca ctgactgact gcttgtccca caccgactca ggacacaagg cctgttacta      2040
gcactcacat ggaacaaatg ccatgcatc  tagagggccc tattctatag tgtcacctaa      2100
atgctagagc tcgctgatca gcctcgactg tgccttctag ttgccagcca tctgttgttt      2160
gcccctcccc cgtgccttcc ttgaccctgg aaggtgccac tcccactgtc ctttcctaat      2220
aaaatgagga aattgcatcg cattgtctga gtaggtgtca ttctattctg gggggtgggg      2280
tggggcagga cagcaagggg gaggattggg aagacaatag caggcatgct ggggagctag      2340
agtcgaccga accggtggaa gtcctcttcc tcggtgtcct tgacttcaaa gggtctctcc      2400
catttgcctg gagagagggg aaggtgggca tcaccagggg tgagtgaagg tttggaagag      2460
tgtagcagaa taagaaacca tgagtcccct ccctgagaag ccctgagccc ccttgacgac      2520
acacatccct cgaggctcag cttcatcatc tgtaaaaggt gctgaaactg accatccaag      2580
ctgccgaaaa agattgtgtg gggataattc aaaactagag gaagatgcag aatttctaca      2640
tcgtggcgat gtcaggctaa gagatgccat cgtggctgtg cattttttatt ggaatcatat      2700 gtttatttga gggtgtcttg gatattacaa ataaaatgtt ggagcatcag gcatatttgg      2760
taccttctgt ctaaggctcc ctgcccctttg ttaattggca gctcagttat tcatccaggg      2820
caaacattct gcttactatt cctgagagct ttcctcatcc tctagattgg caggggaaat      2880
gcagatgcct gagcagcctc ccctctgcca taccaacaga gcttcaccat cgaggcatgc      2940
agagtggaca ggggcctcag ggaccccctga tcccagcttt tcattggac  agaaggagga      3000 gactggggct ggagagggac ctgggccccc actaaggcca cagcagagcc aggactttag      3060
ctgtgctgac tgcagcctgg cttgcctcca ctgccctcct ttgcctcaag agcaagggag      3120
cctcagagtg gaggaagcag cccctggcct tgcctcccac ctccctccc  ctatgctgtt      3180 ttcctgggac agtgggagct ggcttagaat gccctgggc  ccccaggacc ctggcatttt      3240 aaccccctcag gggcaggaag gcagcctgag atacagaaga gtccatcacc tgctgtatgc      3300
cacacaccat ccccacagtt acgtactagt tcgaagccac gcggaccgtt atagttacga      3360 ggaacccccta gtgatggagt tggccactcc ctctctgcgc gctcgctcgc tcactgaggc      3420
cgggcgacca aggtcgcccc gacgcccggg cttgcccgg  gcggcctcag tgagcgagcg      3480
agcgcgcaga gagggagtgg ccaaagatct                                       3510
```

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
agtcggtgtg gttgacaagc a                                                21

<210> SEQ ID NO 18
<211> LENGTH: 989
<212> TYPE: DNA
<213> ORGANISM: Artificial Sequence
<220> FEATURE:
<223> OTHER INFORMATION: Synthetic Construct

<400> SEQUENCE: 18
gtggaagtcc tcttcctcgg tgtccttgac ttcaaagggt ctctcccatt tgcctggaga      60
gaggggaagg tgggcatcac caggggtgag tgaaggtttg gaagagtgta gcagaataag    120
aaaccatgag tcccctccct gagaagccct gagcccccctt gacgcacac atccctcgag    180 gctcagcttc atcatctgta aaggtgctg aaactgacca tccaagctgc cgaaaaagat    240
tgtgtgggga taattcaaaa ctagaggaag atgcagaatt tctacatcgt ggcgatgtca    300
ggctaagaga tgccatcgtg gctgtgcatt tttattggaa tcatatgttt atttgagggt    360
gtcttggata ttacaaataa aatgttggag catcaggcat atttggtacc ttctgtctaa    420
ggctccctgc cccttgttaa ttggcagctc agttattcat ccagggcaaa cattctgctt    480
actattcctg agagctttcc tcatcctcta gattggcagg ggaaatgcag atgcctgagc    540
agcctcccct ctgccatacc aacagagctt caccatcgag gcatgcagag tggacagggg    600
cctcagggac ccctgatccc agctttctca ttggacagaa ggaggagact ggggctggag    660
agggacctgg gcccccacta aggccacagc agagccagga ctttagctgt gctgactgca    720
gcctggcttg cctccactgc cctcctttgc ctcaagagca agggagcctc agagtggagg    780
aagcagcccc tggccttgcc tcccacctcc cctcccctat gctgttttcc tgggacagtg    840
ggagctggct tagaatgccc tggggccccc aggaccctgg cattttaacc cctcaggggc    900
aggaaggcag cctgagatac agaagagtcc atcacctgct gtatgccaca caccatcccc    960
acagttacgt actagttcga agccacgcg                                       989

<210> SEQ ID NO 19
<211> LENGTH: 3510
<212> TYPE: DNA
<213> ORGANISM: Artificial Sequence
<220> FEATURE:
<223> OTHER INFORMATION: Synthetic Construct

<400> SEQUENCE: 19
aaccggtgag ggagagacgc gcgagcgagc gagtgactcc ggcgggcccg tttcgggccc      60
gcagcccgct ggaaaccagc gggccggagt cactcgctcg ctcgcgcgtc tctccctcac    120
cggttgaggt agtgatcccc aaggagatat aatgggacga tccgttaacc tagggcctgg    180
cagctgtaac taataactga tcaataatta tcattagtta atgccccagt aatcaagtat    240
cgggtatata cctcaaggcg caatgtattg aatgccattt accggcgga ccgactggcg    300 ggttgctggg gcgggtaac tgcagttatt actgcataca agggtatcat tgcggttatc    360
cctgaaaggt aactgcagtt acccacctca taaatgccat ttgacgggtg aaccgtcatg    420
tagttcacat agtatacggt tcatgcgggg gataactgca gttactgcca tttaccgggc    480
ggaccgtaat acgggtcatg tactggaata ccctgaaagg atgaaccgtc atgtagatgc    540
ataatcagta gcgataatgg taccagctcc actcggggtg caagacgaag tgagagggt     600

```
agaggggggg gagggggtggg ggttaaaaca taaataaata aaaaattaat aaaacacgtc    660 gctaccccg cccccccccc ccccccgcgc gcggtccgcc ccgccccgcc ccgctccccg      720
ccccgccccg ctccgcctct ccacgccgcc gtcggttagt ctcgccgcgc gaggctttca    780
aaggaaaata ccgctccgcc gccgccgccg ccgggatatt tttcgcttcg cgcgccgccc    840
gccctcagcg acgcgcgacg gaagcggggc acggggcgag gcggcggcgg agcgcggcgg    900
gcggggccga gactgactgg cgcaatgagg gtgtccactc gcccgccctg ccgggaagag    960
gaggcccgac attaatcgcg aaccaaatta ctgccgaaca aagaaaagac accgacgcac    1020
tttcggaact ccccgaggcc ctcccgggaa acacgccccc ctcgccgagc ccccacgca    1080 cgcacacaca cacgcacccc tcgcggcgca cgccgaggcg cgacgggccg ccgacactcg    1140
cgacgcccgc gccgcgcccc gaaacacgcg aggcgtcaca cgcgctcccc tcgcgccggc    1200
ccccgccacg gggcgccacg cccccccccga cgctcccctt gtttccgacg cacgcccac    1260 acacgcaccc cccactcgt cccccacacc cgcgcagcca gccgacgtt gggggggacg     1320 tgggggagg ggctcaacga ctcgtgccgg gccgaagccc acgccccgag gcatgccccg     1380
caccgcgccc cgagcggcac ggcccgcccc ccaccgccgt ccaccccac ggcccgcccc     1440 gccccggcgg agcccggccc ctcccgagcc ccctccccgc gccgccgggg gcctcgcggc    1500
cgccgacagc tccgcgccgc tcggcgtcgg taacgaaaaa taccattagc acgctctccc    1560
gcgtccctga aggaaacagg gtttagacac gcctcggctt tagaccctcc gcggcggcgt    1620
gggggagatc gcccgcgccc cgcttcgcca cgccgcggcc gtccttcctt tacccgcccc    1680
tcccggaagc acgcagcggc gcggcggcag gggaagaggg agaggtcgga gccccgacag    1740 gcgccccct gccgacggaa gccccccctg cccccgtcccg ccccaagccg aagaccgcac    1800
actggccgcc gagatctcgg agacgattgg tacaagtacg gaagaagaaa aaggatgtcg    1860
aggacccgtt gcacgaccaa taacacgaca gagtagtaaa accgtttctt aagaagcttt    1920
ctagacgatc ggaccctccga acgacttccg acatacgact cagccacacc aactgttcgt    1980
caaaaccggt gactgactga cgaacagggt gtggctgagt cctgtgttcc ggacaatgat    2040
cgtgagtgta ccttgtttac cggtacgtag atctcccggg ataagatatc acagtggatt    2100
tacgatctcg agcgactagt cggagctgac acggaagatc aacggtcggt agacaacaaa    2160
cggggagggg gcacggaagg aactgggacc ttccacggtg agggtgacag gaaaggatta    2220
ttttactcct ttaacgtagc gtaacagact catccacagt aagataagac cccccacccc    2280
accccgtcct gtcgttcccc ctcctaaccc ttctgttatc gtccgtacga cccctcgatc    2340
tcagctggcc tggccaccct caggagaagg agccacagga actgaagttt cccagagagg    2400
gtaaacggac ctctctcccc ttccacccgt agtggtcccc actcacttcc aaaccttctc    2460
acatcgtctt attctttggt actcagggga gggactcttc gggactcggg ggaactgctg    2520
tgtgtaggga gctccgagtc gaagtagtag acatttttcca cgactttgac tggtaggttc    2580
gacggctttt tctaacacac ccctattaag ttttgatctc cttctacgtc ttaaagatgt    2640
agcaccgcta cagtccgatt ctctacggta gcaccgacac gtaaaaataa ccttagtata    2700
caaataaact cccacagaac ctataatgtt tattttacaa cctcgtagtc cgtataaacc    2760
atggaagaca gattccgagg gacggggaac aattaaccgt cgagtcaata agtaggtccc    2820
gtttgtaaga cgaatgataa ggactctcga aaggagtagg agatctaacc gtccccttta    2880
cgtctacgga ctcgtcggag gggagacggt atggttgtct cgaagtggta gctccgtacg    2940
tctcacctgt ccccggagtc cctggggact agggtcgaaa gagtaacctg tcttcctcct    3000
```

| | |
|---|---|
| ctgaccccga cctctccctg gacccggggg tgattccggt gtcgtctcgg tcctgaaatc | 3060 |
| gacacgactg acgtcggacc gaacggaggt gacgggagga acggagttc tcgttccctc | 3120 |
| ggagtctcac ctccttcgtc ggggaccgga acggagggtg gaggggaggg gatacgacaa | 3180 |
| aaggaccctg tcaccctcga ccgaatctta cgggaccccg ggggtcctgg gaccgtaaaa | 3240 |
| ttggggagtc cccgtccttc cgtcggactc tatgtcttct caggtagtgg acgacatacg | 3300 |
| gtgtgtggta ggggtgtcaa tgcatgatca agcttcggtg cgcctggcaa tatcaatgct | 3360 |
| ccttggggat cactacctca accggtgagg gagagacgcg cgagcgagcg agtgactccg | 3420 |
| gcccgctggt ttccagcggg ctgcgggccc gaaacgggcc cgccggagtc actcgctcgc | 3480 |
| tcgcgcgtct ctccctcacc ggtttctaga | 3510 |

<210> SEQ ID NO 20
<211> LENGTH: 3798
<212> TYPE: DNA
<213> ORGANISM: Artificial Sequence
<220> FEATURE:
<223> OTHER INFORMATION: Synthetic Construct

<400> SEQUENCE: 20

| | |
|---|---|
| aattcgccct tgggcctagg caattggatc cgccggcaga gaaaacatcc cagggattta | 60 |
| cagatcacat gcaggcaggg accagctcaa cccttcttta atgtcatcca ggagggggc | 120 |
| cagggatgga ggggaggggt tgaggagcga gaggcagtta ttttggggtg ggattcacca | 180 |
| cttttcccat gaagagggga gacttggtat tttgttcaat cattaagaag acaaagggtt | 240 |
| tgttgaactt gacctcgggg gggatagaca tgggtatggc ctctaaaaac atggccccag | 300 |
| cagcttcagt ccctttctcg tcgatggtca gcacagcctt atgcacggcc tggaggggag | 360 |
| agaagcagag acacgttgta aggctgatcc caggcctcga gcaaggctca cgtggacacc | 420 |
| tcccaggaag cgctcactcc ccctggacgg ccctggccct gcacatcctc tccctccctg | 480 |
| tcacataggc cttgctcctc ctcaaggctt tggctgatgg ggctggctcc cctctgtcca | 540 |
| tcttcctgac aagcgcctct cccctgctc aggtgcaccc acaactcaga acagggaaga | 600 |
| gcatcgtcac tccacgtctg cctccagggc tctctccttt ctagtacacg gcttgaagct | 660 |
| ccttgaggac acggaccctg gcagtgacct tcacagtgcc cagacccaa gataatgcag | 720 |
| ccattcatgg aactgcaggt tgttcattgg tcgcctttag ttttccaaaa taagtgtcac | 780 |
| tttagctgaa atcattcatt aattcagaca ccaaatctca cagatcgaag gagtcagaaa | 840 |
| ttcctttgaa acaacttagc ccaaacccttt ctgtgtcagt atggataaat caaggcccaa | 900 |
| tgtctagaag gtcttgggca aagttgaaat tcagggtcag tgacacaacc tcaagggagg | 960 |
| ccccgaaagt gccagctgca cagcagcccc tgcctggctt tgctgtttgc ccaccgtccc | 1020 |
| gtgtcagtga atcacgggca tcttcaggag ctcagcctgg gtcttcattt gtttccctcg | 1080 |
| gccccttcct cagcctcagg acagtgctgc agccccaca cattcttccc tacagatacc | 1140 |
| atggtgcaac aaggtcgtca gggtgatctc accttggaga gcttcagggg tgcctcctct | 1200 |
| gtgaccccgg agaggtcagc cccattgctg aagaccttag tgatgcccag ttgacccagg | 1260 |
| acgctcttca gatcataggt tccagtaatg gacagtttgg gtaaatgtaa gctggcagac | 1320 |
| ctgtcgtgca gaaaagaaat tcaaggcatg gcacagcatt cctcttgttc ttctgggacc | 1380 |
| caccacagtg caagtgtttt cttttctgat tatttctgcc acttactcct gtgtcctcca | 1440 |
| cccacactaa gatgggaact cggctttggt tgttctact tttagctctt ctacattgag | 1500 |

```
tcaaagaatg ttaacatcga atgaatcaca aaagcttgaa atgccacctc ctctgatatt   1560
ctaggtgtcc tggaagcctg tctcatcttg ccctgtagtg ttgggtcacc tggcccccag   1620
cctgtaacat ccccagggcc ctacacccag agaaacacgg ggctggtggc agtgcccagt   1680
gacaaccgtt tagtggataa agaagagtg accacaccag gctgagtgct cctctctggt   1740
tttccatggg gagacaatgc caccctgagc agggtctggt gtgagcggca gctggctctg   1800
ggctctctga tccgttaccc tctcagcctc tttgttcttt ctcaacccct ggagcagaga   1860
cctcaggagg tgctggcatg aacagagaa attccagcct cgattcctat tatgaacccg   1920
acaccttttg tattttcatc ttggttttac agtgtacaaa acgaactaga tcagcagggc   1980
atgggcataa tcacgaatgc acacacatac actaatgtgt ggctcatgtt taagtatcac   2040
ttactacagg acacccaatc taacagcacc gataaagtga cagagaaacg caagccttct   2100
gcgaacatgg cctggctgtt ccaattccga accttgcttt tctgggcctt gccacacagg   2160
ctcttccccc gtcccccag ggacattcta cccttgaact ccacactcca ctgctgcctt   2220
tgccaggaag cccatctgtt cctttttggt tctgccagaa cgtgtggtgg tgctgctgtc   2280
cctgccttgg gcactggata ttgggaaggg acagtgtcca cactggagtg ggaagttccc   2340
agggacgaga ccttacctc ctcacctgg gtactgttct cctcatggag catggacggc   2400
gctgcctgaa ctcagtggtg gcctcattct ggaagccaag tttatacaga gtagcagtga   2460
cccagggatg tggggttcac cctcctcagc cctctggcca gtcctgatgg gcctcagtcc   2520
caacatggct aagaggtgtg ggcagcttct tggtcaccct caggttgggg aatcaccttc   2580
tgtcttcatt ttccaggaac ttggtgatga tatcgtgggt gagttcattt accaggtgct   2640
gtagtttccc ctcatcaggc aggaagaaga tggcggtggc attgcccagg tatttcatca   2700
gcagcaccca gctggacagc ttcttacagt gctggatgtt aaacatgcct aaacgcttca   2760
tcataggcac cttcacggtg gtcacctggt ccacgtggaa gtcctcttcc tcggtgtcct   2820
tgacttcaaa gggtctctcc catttgcctg gagagagggg aaggtgggca tcaccagggg   2880
tgagtgaagg tttggaagag tgtagcagaa taagaaacca tgagtcccct ccctgagaag   2940
ccctgagccc ccttgacgac acacatccct cgaggctcag cttcatcatc tgtaaaaggt   3000
gctgaaactg accatccaag ctgccgaaaa agattgtgtg gggataattc aaaactagag   3060
gaagatgcag aatttctaca tcgtggcgat gtcaggctaa gagatgccat cgtggctgtg   3120
cattttttatt ggaatcatat gtttatttga gggtgtcttg gatattacaa ataaaatgtt   3180
ggagcatcag gcatatttgg taccttctgt ctaaggctcc ctgccccttg ttaattggca   3240
gctcagttat tcatccaggg caaacattct gcttactatt cctgagagct ttcctcatcc   3300
tctagattgg caggggaaat gcagatgcct gagcagcctc ccctctgcca taccaacaga   3360
gcttcaccat cgaggcatgc agagtggaca ggggcctcag ggaccctga tcccagcttt   3420
ctcattggac agaaggagga gactggggct ggagagggac ctgggccccc actaaggcca   3480
cagcagagcc aggactttag ctgtgctgac tgcagcctgg cttgcctcca ctgccctcct   3540
ttgcctcaag agcaagggag cctcagagtg gaggaagcag cccctggcct tgcctcccac   3600
ctcccctccc ctatgctgtt ttcctgggac agtgggagct ggcttagaat gccctggggc   3660
ccccaggacc ctggcatttt aacccctcag gggcaggaag gcagcctgag atacagaaga   3720
gtccatcacc tgctgtatgc cacacaccat ccccacagtt acgtactagt tcgaagccac   3780
gcgtccgaag ggcgaatt                                                 3798
```

```
<210> SEQ ID NO 21
<211> LENGTH: 350
<212> TYPE: DNA
<213> ORGANISM: Artificial Sequence
<220> FEATURE:
<223> OTHER INFORMATION: Synthetic Construct

<400> SEQUENCE: 21
ggagtcgctg cgcgctgcct tcgccccgtg ccccgctccg ccgccgcctc gcgccgcccg      60
ccccggctct gactgaccgc gttactccca caggtgagcg ggcgggacgg cccttctcct     120
ccgggctgta attagcgctt ggtttaatga cggcttgttt cttttctgtg gctgcgtgaa     180
agccttgagg ggctccggga gctagagcct ctgctaacca tgttcatgcc ttcttctttt     240
tcctacagct cctgggcaac gtgctggtta ttgtgctgtc tcatcatttt ggcaaagaat     300
tcctcgaaga tccggtaccc aattccgggg ccccacgctg cgcatccgcg                350

<210> SEQ ID NO 22
<211> LENGTH: 59
<212> TYPE: DNA
<213> ORGANISM: Artificial Sequence
<220> FEATURE:
<223> OTHER INFORMATION: Synthetic Construct

<400> SEQUENCE: 22
tggccgtcca tcttggaccc ggttttggcc actgactgac cgggtccaat ggacggcca      59
```